US011510928B2

(12) United States Patent
Swain et al.

(10) Patent No.: US 11,510,928 B2
(45) Date of Patent: Nov. 29, 2022

(54) USE OF MIRTAZAPINE IN THE TREATMENT OF INFLAMMATORY DISORDERS, AUTOIMMUNE DISEASE AND PBC

(71) Applicant: UTI Limited Partnership, Calgary (CA)

(72) Inventors: Mark G. Swain, Calgary (CA); Abdel Aziz Shaheen, Calgary (CA); Wagdi Almishri, Calgary (CA); Gilaad G. Kaplan, Calgary (CA)

(73) Assignee: UTI Limited Partnership, Calgary (CA)

( * ) Notice: Subject to any disclaimer, the term of this patent is extended or adjusted under 35 U.S.C. 154(b) by 29 days.

(21) Appl. No.: 16/644,740

(22) PCT Filed: Sep. 7, 2018

(86) PCT No.: PCT/CA2018/051098
§ 371 (c)(1),
(2) Date: Mar. 5, 2020

(87) PCT Pub. No.: WO2019/046959
PCT Pub. Date: Mar. 14, 2019

(65) Prior Publication Data
US 2020/0188409 A1 Jun. 18, 2020

Related U.S. Application Data

(60) Provisional application No. 62/555,397, filed on Sep. 7, 2017.

(51) Int. Cl.
| | |
|---|---|
| *A61K 31/55* | (2006.01) |
| *A61P 1/16* | (2006.01) |
| *A61P 37/06* | (2006.01) |
| *A61K 31/575* | (2006.01) |
| *A61K 45/06* | (2006.01) |

(52) U.S. Cl.
CPC ............ *A61K 31/55* (2013.01); *A61K 31/575* (2013.01); *A61K 45/06* (2013.01); *A61P 1/16* (2018.01); *A61P 37/06* (2018.01)

(58) Field of Classification Search
CPC .................................. A61K 31/55; A61P 1/16
See application file for complete search history.

(56) References Cited

U.S. PATENT DOCUMENTS

2005/0187200 A1* 8/2005 Auspitz ................... A61P 21/04
514/159
2014/0271727 A1 9/2014 Hwang et al.

FOREIGN PATENT DOCUMENTS

WO WO-2018/05695 A1 1/2018

OTHER PUBLICATIONS

Adams et al., "Increased Expression of Intercellular Adhesion Molecule 1 on Bile Ducts in Primary Biliary Cirrhosis and Primary Sclerosing Cholangitis," Hepatology. 14(3):426-431 (1991).
Ajuebor et al., "Lack of Chemokine Receptor Ccr5 Promotes Murine Fulminant Liver Failure by Preventing the Apoptosis of Activated Cd1d-restricted Nkt Cells," J Immunol. 174(12):8027-8037 (2005).
Al-Harthy et al., "The Specificity of Fatigue in Primary Biliary Cirrhosis: Evaluation of a Large Clinic Practice," Hepatology. 52(2):562-570 (2010).
Alam et al., "A Review of Therapeutic Uses of Mirtazapine in Psychiatric and Medical Conditions," Prim Care Companion CNS Disord. 15(5):PCC.13r01525:1-19 (2013).
Almishri et al., "Rapid Activation and Hepatic Recruitment of Innate-Like Regulatory B Cells After Invariant NKT Cell Stimulation in Mice," J Hepatol. 63(4):943-951 (2015).
Auffray et al., "Monitoring of Blood Vessels and Tissues by a Population of Monocytes With Patrolling Behavior," Science. 317(5838):666-760 (2017).
Benezech et al., "Inflammation-induced Formation of Fat-associated Lymphoid Clusters," Nat Immunol. 16(8):819-828 (2015).
Bhayat and Das-Gupta., "The Incidence of and Mortality From Leukaemias in the UK: A General Population-based Study," BMC Cancer. 9:252 (2009).
Bittolo et al., "Pharmacological Treatment With Mirtazapine Rescues Cortical Atrophy and Respiratory Deficits in Mecp2 Null Mice," Sci Rep. 6:19796 (2016).
Borchers et al., "Lymphocyte Recruitment and Homing to the Liver in Primary Biliary Cirrhosis and Primary Sclerosing Cholangitis," Semin Immunopathol. 31(3):309-322 (2009).
Chauhan et al., "Levels of Foxp3 in Regulatory T Cells Reflect Their Functional Status in Transplantation," J Immunol. 182(1):148-153 (2009).
Chuang el al., "Increased Levels of Chemokine Receptor CXCR3 and Chemokines IP-10 and MIG in Patients With Primary Biliary Cirrhosis and Their First Degree Relatives," J Autoimmun. 25(2):126-132 (2005).
Crispe et al., "Migration of Lymphocytes Into Hepatic Sinusoids," J Hepatol. 57:218-220 (2012).
Croom et al., "Mirtazapine: A Review of Its Use in Major Depression and Other Psychiatric Disorders," CNS Drugs. 23(5):427-452 (2009).
Dal-Secco et al., "A Dynamic Spectrum of Monocytes Arising From the in Situ Reprogramming of CCR2+ Monocytes at a Site of Sterile Injury," J Exp Med. 212(4):447-456 (2015).
Erhardt et al., "CXCR3 Deficiency Exacerbates Liver Disease and Abrogates Tolerance in a Mouse Model of Immune-mediated Hepatitis," J Immunol. 186(9):5284-5293 (2011).
Eyre et al., "Modulatory Effects of Antidepressant Classes on the Innate and Adaptive Immune System in Depression," Pharmacopsychiatry. 49(3):85-96 (2016).
Frick and Rapanelli, "Antidepressants: Influence on Cancer and Immunity?," Life Sciences. 92(10): 525-532 (2013).
Geissmann et al., "Blood Monocytes Consist of Two Principal Subsets With Distinct Migratory Properties," Immunity. 19(1):71-82 (2003).

(Continued)

*Primary Examiner* — Kevin E Weddington
(74) *Attorney, Agent, or Firm* — Clark & Elbing LLP

(57) ABSTRACT

There is described herein the use of mirtazapine in methods for the treatment of inflammatory disorders, autoimmune disease, and PBC.

3 Claims, 31 Drawing Sheets

(56) References Cited

OTHER PUBLICATIONS

Gittlen et al., "Raised Histamine Concentrations in Chronic Cholestatic Liver Disease," Gut. 31(1):96-99(1990).
Harada et al., "In Situ Nucleic Acid Hybridization of Cytokines in Primary Biliary Cirrhosis: Predominance of the Th1 Subset," Hepatology. 25(4):791-796 (1997).
Harrington et al., "Interleukin 17-producing CD4+ Effector T Cells Develop via a Lineage Distinct From the T Helper Type 1 and 2 Lineages," Nat Immunol. 6(11):1123-1132 (2005).
Heymann and Tacke., "Immunology in the Liver—from Homeostasis to Disease," Nat Rev Gastroenterol Hepatol. 13(2):88-110 (2016).
Hohenester et al., "Primary Biliary Cirrhosis," Semin Immunopathol. 31(3):283-307 (2009).
Hui Hsu et al., "A B-1a Cell Subset Induces Foxp3(-) T Cells With Regulatory Activity Through an IL-10-independent Pathway," Cell Mol Immunol. 12(3):354-365 (2015).
International Preliminary Report on Patentability for International Application No. PCT/CA2018/051098, dated Mar. 10, 2020 (1 page).
International Search Report and Written Opinion for International Application No. PCT/CA2018/051098, dated Apr. 12, 2018 (15 pages).
Jenne and Kubes.,"Immune Surveillance by the Liver," Nat Immunol. 14(10): 996-1006 (2013).
Jin et al., "Comparative Analysis of Portal Cell Infiltrates in Antimitochondrial Autoantibody-positive Versus Antimitochondrial Autoantibody-negative Primary Biliary Cirrhosis," Hepatology. 55(5):1495-1506 (2012).
Jones et al., "Inhibition of Mast Cell-secreted Histamine Decreases Biliary Proliferation and Fibrosis in Primary Sclerosing Cholangitis Mdr2(−/−) Mice," Hepatology. vol. 64(4): 1202-1216 (2016).
Fang et al., "Mirtazapine Inhibits Tumor Growth via Immune Response and Serotonergic System," PLoS One. 7(7):e38886 (2012).
Kaku et al., "A Novel Mechanism of B Cell-mediated Immune Suppression Through CdD3 Expression and Adenosine Production," J Immunol. 193(12):5904-5913 (2014).
Kawasuji et al., "L-selectin and Intercellular Adhesion Molecule-1 Regulate the Development of Concanavalin a-induced Liver Injury," J Leukoc Biol. 79(4):696-705 (2006).
Kouroumalis and Notas, "Primary Biliary Cirrhosis: From Bench to Bedside," World J Gastrointest Pharmacol Ther. 6(3):32-58 (2015).
Kraus et al., "Body Weight, the Tumor Necrosis Factor System, and Leptin Production During Treatment With Mirtazapine or Venlafaxine," Pharmacopsychiatry. 35(6):220-225 (2002).
Kronman et al., "Antibiotic Exposure and IBD Development Among Children: a Population-based Cohort Study," Pediatrics. 130(4):e794-803 (2012).
Lalor et al., "Hepatic Sinusoidal Endothelium Avidly Binds Platelets in an Integrin-dependent Manner, Leading to Platelet and Endothelial Activation and Leukocyte Recruitment," American Journal of Physiology Gastrointestinal and Liver Physiology. 304(5):G469-G478 (2013).
Lammers et al., "Levels of Alkaline Phosphatase and Bilirubin are Surrogate End Points of Outcomes of Patients With Primary Biliary Cirrhosis: an International Follow-up Study," Gastroenterology. 147(6):1338-1349 (2014).
Lawrance et al., "A Murine Model of Chronic Inflammation-induced Intestinal Fibrosis Down-regulated by Antisense NF-Kappa B," Gastroenterology. 125(6):1750-1761 (2003).
Mehal et al., "Selective Retention of Activated CD8+ T Cells by the Normal Liver," J Immunol. 163(6): 3202-3210 (1999).
Mells et al., "Impact of Primary Biliary Cirrhosis on Perceived Quality of Life: The UK-PBC National Study," Hepatology. 58(1): 273-283 (2013).
Miyagaki et al., "Regulatory B Cells in Human Inflammatory and Autoimmune Diseases: From Mouse Models to Clinical Research," International Immunology. 27(10): 495-504 (2015).

Morikawa et al., "Sublobular Veins as the Main Site of Lymphocyte Adhesion/transmigration and Adhesion Molecule Expression in the Porto-sinusoidal-hepatic Venous System During Concanavalin a-induced Hepatitis in Mice," Hepatology. 31(1):83-94 (2000).
Mossner and Lesch., "Role of Serotonin in the Immune System and in Neuroimmune Interactions," Brain, Behavior, and Immunity. vol. 12: 249-271 (1998).
Munzer et al., "Impact of antidepressants on cytokine production of depressed patients in vitro," Toxins (Basel). 5(11):2227-2240 (2013).
Myers et al., "B-cell Depletion With Rituximab in Patients With Primary Biliary Cirrhosis Refractory to Ursodeoxycholic Acid," Am J Gastroenterol. 108(6):933-941 (2013).
Myers et al., "Epidemiology and Natural History of Primary Biliary Cirrhosis in a Canadian Health Region: A Population-based Study," Hepatology. vol. 50(6):1884-1892 (2009).
Nakayama et al., "Mirtazapine Increases Dopamine Release in Prefrontal Cortex by 5-HT1A Receptor Activation," Brain Research Bulletin. 63(3):237-241 (2004).
Njoku., "Suppressive and Pro-inflammatory Roles for II-4 in the Pathogenesis of Experimental Drug-induced Liver Injury: A Review," Expert Opin Drug Metab Toxicol. 6(5): 519-531 (2010).
O'Connell et al., "A Novel Form of Immune Signaling Revealed by Transmission of the Inflammatory Mediator Serotonin Between Dendritic Cells and T Cells," Blood. 107(3):1010-1017 (2006).
O'Garra et al., "Ly-1 B (B-1) Cells are the Main Source of B Cell-derived Interleukin 10," Eur J Immunol. 22(3): 711-717 (1992).
Okada et al., "Liver Resident Macrophages (Kupffer Cells) Share Several Functional Antigens in Common with Endothelial Cells," Scandinavian Journal of Immunology. 83:139-150 (2015).
Oo and Sakaguchi., "Regulatory T-cell Directed Therapies in Liver Diseases," J Hepatol. 59(5):1127-1134 (2013).
Pares et al., "Excellent Long-term Survival in Patients With Primary Biliary Cirrhosis and Biochemical Response to Ursodeoxycholic Acid," Gastroenterology. 130(3):715-720 (2006).
Park et al., "Liver Injury Associated with Antidepressants," Curr Drug Saf. 8(3):207-223 (2013).
Rosser and Mauri et al., "Regulatory B Cells: Origin, Phenotype, and Function," Immunity. 42(4):607-612(2015).
Ruddell et al., "The Function of Serotonin Within the Liver," J Hepatol. 48(4):666-675 (2008).
Samuelson et al., "Blk Haploinsufficiency Impairs the Development, but Enhances the Functional Responses, of Mz B Cells," Immunol Cell Biol. 90(6):620-629 (2012).
Saze et al., "Adenosine Production by Human B Cells and B Cell-mediated Suppression of Activated T Cells," Blood. 122(1):9-18 (2013).
Shaheen et al., "The impact of depression and antidepressant usage on primary biliary cholangitis clinical outcomes," PLoS One. 13(4):1-13 (2018).
Shetty et al., "Recruitment Mechanisms of Primary and Malignant B Cells to the Human Liver," Hepatology. 56(4):1521-1531 (2012).
Tato et al., "Helper T Cell Differentiation Enters a New Era: Le Roi Est Mort; Vive Le Roi," J Exp Med. 203(4):809-812(2006).
Thin., "Thin Data Guide for Researchers version 2.4," CSD Medical Research UK. pp. 1-117 (2012).
Vadasz et al., "B-Regulatory Cells in Autoimmunity and Immune Mediated Inflammation," FEBS Lett. 587(13):2074-2078 (2013).
Wallace et al., "Age-Specific Incidence and Prevalence Rates of Treated Epilepsy in an Unselected Population of 2,052,922 and Age-specific Fertility Rates of Women With Epilepsy," Lancet. 352(9145):1970-1973 (1998).
Wang et al., "New Insights Into Heterogeneity of Peritoneal B-1a Cells," Annals of the New York Academy of Sciences. 1362(1): 68-76 (2015).
Wasmuth et al., "Antifibrotic Effects of CXCL9 and Its Receptor CXCR3 in Livers of Mice and Humans," Gastroenterology. 137(1):309-319 (2009).
Wolf et al., "TNF-alpha-induced Expression of Adhesion Molecules in the Liver is Under the Control of TNFR1—relevance for Concanavalin A-induced Hepatitis," J Immunol. 166(2):1300-1307 (2001).
Yanaba et al., "B-lymphocyte Contributions to Human Autoimmune Disease," Immunol Rev. 223:284-299 (2008).

(56) References Cited

OTHER PUBLICATIONS

Yang et al., "IL-12/Th1 and IL-23/Th17 Biliary Microenvironment in Primary Biliary Cirrhosis: Implications for Therapy," Hepatology. 59(5):1944-1953 (2014).

Yasoshima et al., "Immunohistochemical Analysis of Adhesion Molecules in the Microenvironment of Portal Tracts in Relation to Aberrant Expression of PDC-E2 and HLA-DR on the Bile Ducts in Primary Biliary Cirrhosis," The Journal of Pathology. 175(3):319-325 (1995).

* cited by examiner

C

D  E

F

G

Flow diagram of identified PBC patients in The Health Improvement Network between April 1974 and May 2007.

A

B

USE OF MIRTAZAPINE IN THE TREATMENT OF INFLAMMATORY DISORDERS, AUTOIMMUNE DISEASE AND PBC

CROSS REFERENCE TO RELATED APPLICATION

This application claims the benefit of priority to U.S. Provisional Patent Application No. 62/555,397, filed Sep. 7, 2017 the contents of which is hereby incorporated by reference.

FIELD

The present disclosure relates generally to treatment of inflammatory disorders, autoimmune disease, and PBC.

BACKGROUND

Primary biliary cholangitis (PBC) is a prototypic autoimmune disease, characterized by immune-mediated destruction of small bile ducts within the liver[1]. This immune attack, mainly mediated by activated T cells, contributes to hepatocyte injury and the slowly progressive development of liver fibrosis[1]. The bile acid ursodeoxycholic acid (UDCA) has been the only available therapy for PBC for over two decades. Unfortunately, 30% to 40% of patients with PBC do not fully respond to UDCA and are at risk of progressing to cirrhosis, liver failure, and death[2].

SUMMARY

In one aspect there is described a method of treating a subject having primary biliary cirrhosis, suspected of having primary biliary cirrhosis, or at risk of developing biliary cirrhosis, comprising: administering a therapeutically effective amount of mirtazapine or a functional derivative thereof.

In one example, further comprising administering ursodeoxycholic acid (UDCA).

In one example, further comprising administering one or more of obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, or tetrathiomolybdate.

In one example, wherein the subject is a human.

In one aspect there is described a method of treating a subject having an inflammatory disorder, a subject suspected of having an inflammatory disorder, or a subject at risk of having an inflammatory disorder, comprising: administering a therapeutically effective amount of mirtazapine or a functional derivative thereof.

In one example, wherein the inflammatory disorder is one or more of chronic inflammation, acute inflammation, Celiac Disease, rheumatoid arthritis (RA), Inflammatory Bowel Disease (IBD), asthma, encephalitis, chronic obstructive pulmonary disease (COPD), inflammatory osteolysis, Crohn's disease, ulcerative colitis, allergic disorders, septic shock, pulmonary fibrosis (e.g. idiopathic pulmonary fibrosis), inflammatory vaculitides (e.g., polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, chronic inflammation resulting from chronic viral or bacterial infections, and acute inflammation, such as sepsis. In a particular embodiment, the immune-mediated inflammatory disease is selected from the group consisting of rheumatoid arthritis (RA), Inflammatory Bowel Disease (IBD), or Crohn's disease.

In one example, further comprising administering ursodeoxycholic acid (UDCA).

In one example, wherein the subject is a human.

In one aspect there is described a method of treating a subject having an autoimmune disease, a subject suspected of having an autoimmune disease, or a subject at risk of having autoimmune disease, comprising: administering a therapeutically effective amount of mirtazapine or a functional derivative thereof.

In one example, wherein the autoimmune disease is Addison's disease, alopecia areata, ankylosing spondylitis, autoimmune hepatitis, autoimmune parotitis, autoimmune thyroiditis, autoimmune gastritis, autoimmune adrenalitis, autoimmune hypoparathyriodism, autoimmune diabetes, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjögren's syndrome, spondyloarthropathies, thyroiditis, vasculitis, vitiligo, myxedema, pernicious anemia, ulcerative colitis, paraneoplastic neurological disorders such as Lambert-Eaton Myasthenic Syndrome, inflammatory bowel disease, sarcoidosis, Achalasia, Adult Still's disease, Agammaglobulinemia, Achalasia, Addison's disease, Adult Still's disease, Agammaglobulinemia, Amyloidosis, Anti-GBM/Anti-TBM nephritis, Antiphospholipid syndrome, Autoimmune angioedema, Autoimmune dysautonomia, Autoimmune encephalomyelitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Goodpasture's syndrome, Granulomatosis with Polyangiitis, Hashimoto's thyroiditis, Henoch-Schonlein purpura (HSP), Herpes gestationis or pemphigoid gestationis (PG), Hidradenitis Suppurativa (HS) (Acne Inverse), Hypogammalglobulinemia, IgA Nephropathy, IgG4-related sclerosing disease, Inflammatory bowel disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Schmidt syndrome, Scleritis, Systemic sclerosis, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Undifferentiated connective tissue disease (UCTD), Uveitis, Vogt-Koyanagi-Harada Disease or Wegener's granulomatosis (or Granulomatosis with Polyangiitis (GPA)).

In one example, further comprising administering ursodeoxycholic acid (UDCA).

In one example, wherein said subject is a human.

In one aspect there is described a method of increasing the number of Treg cells in a subject, comprising: administering a therapeutically effective amount of mirtazapine or a functional derivative thereof.

In one aspect there is described a method of increasing the number of Breg cells in a subject, comprising: administering a therapeutically effective amount of mirtazapine or a functional derivative thereof.

In one example, wherein the subject is a human.

In one aspect there is described a method of treating a subject with a disease, disorder, or condition, that would benefit from an increase in the number of Tregs, comprising administering a therapeutically effective amount of mirtazapine or a functional derivative thereof.

In one aspect there is described a method of treating a subject with a disease, disorder, or condition, that would benefit from an increase in the number of Bregs, comprising administering a therapeutically effective amount of mirtazapine or a functional derivative thereof.

In one example, wherein disease, disorder, or condition, is an inflammatory disorder, or autoimmune disease, or PBC.

In one example, wherein the inflammatory disorder is chronic inflammation, acute inflammation, Celiac Disease, rheumatoid arthritis (RA), Inflammatory Bowel Disease (IBD), asthma, encephalitis, chronic obstructive pulmonary disease (COPD), inflammatory osteolysis, Crohn's disease, ulcerative colitis, allergic disorders, septic shock, pulmonary fibrosis (e.g. idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, chronic inflammation resulting from chronic viral or bacterial infections, and acute inflammation, such as sepsis. In a particular embodiment, the immune-mediated inflammatory disease is selected from the group consisting of rheumatoid arthritis (RA), Inflammatory Bowel Disease (IBD), or Crohn's disease.

In one example, wherein the autoimmune disease is Addison's disease, alopecia areata, ankylosing spondylitis, autoimmune hepatitis, autoimmune parotitis, autoimmune thyroiditis, autoimmune gastritis, autoimmune adrenalitis, autoimmune hypoparathyriodism, autoimmune diabetes, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjögren's syndrome, spondyloarthropathies, thyroiditis, vasculitis, vitiligo, myxedema, pernicious anemia, ulcerative colitis, paraneoplastic neurological disorders such as Lambert-Eaton Myasthenic Syndrome, inflammatory bowel disease, sarcoidosis, Achalasia, Adult Still's disease, Agammaglobulinemia, Achalasia, Addison's disease, Adult Still's disease, Agammaglobulinemia, Amyloidosis, Anti-GBM/Anti-TBM nephritis, Antiphospholipid syndrome, Autoimmune angioedema, Autoimmune dysautonomia, Autoimmune encephalomyelitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Goodpasture's syndrome, Granulomatosis with Polyangiitis, Hashimoto's thyroiditis, Henoch-Schonlein purpura (HSP), Herpes gestationis or pemphigoid gestationis (PG), Hidradenitis Suppurativa (HS) (Acne Inverse), Hypogammalglobulinemia, IgA Nephropathy, IgG4-related sclerosing disease, Inflammatory bowel disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Schmidt syndrome, Scleritis, Systemic sclerosis, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Undifferentiated connective tissue disease (UCTD), Uveitis, Vogt-Koyanagi-Harada Disease or Wegener's granulomatosis (or Granulomatosis with Polyangiitis (GPA)).

In one example, further comprising administering ursodeoxycholic acid (UDCA).

In one example, wherein said subject is a human.

In one aspect there is described use of a therapeutically effective amount of mirtazapine or a functional derivative thereof, for treating a subject having primary biliary cirrhosis, suspected of having primary biliary cirrhosis, or at risk of developing biliary cirrhosis.

In one aspect there is described a use of a therapeutically effective amount of mirtazapine or a functional derivative thereof, in the manufacture of a medicament for treating a subject having primary biliary cirrhosis, suspected of having primary biliary cirrhosis, or at risk of developing biliary cirrhosis.

In one example, further comprising use of ursodeoxycholic acid (UDCA).

In one example, further comprising use of one or more or obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, or tetrathiomolybdate.

In one example, wherein the subject is a human.

In one aspect there is described a use of a therapeutically effective amount of mirtazapine or a functional derivative thereof for treating a subject having an inflammatory disorder, a subject suspected of having an inflammatory disorder, or a subject at risk of having an inflammatory disorder.

In one aspect there is described a use of a therapeutically effective amount of mirtazapine or a functional derivative thereof in the manufacture of a medicament for treating a subject having an inflammatory disorder, a subject suspected of having an inflammatory disorder, or a subject at risk of having an inflammatory disorder.

In one example, wherein the inflammatory disorder is chronic inflammation, acute inflammation, Celiac Disease, rheumatoid arthritis (RA), Inflammatory Bowel Disease (IBD), asthma, encephalitis, chronic obstructive pulmonary disease (COPD), inflammatory osteolysis, Crohn's disease, ulcerative colitis, allergic disorders, septic shock, pulmonary fibrosis (e.g. idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, chronic inflammation resulting from chronic viral or bacterial infections, and acute inflammation, such as sepsis. In a particular embodiment, the immune-mediated inflammatory disease is selected from the group consisting of rheumatoid arthritis (RA), Inflammatory Bowel Disease (IBD), or Crohn's disease.

In one example, further comprising use of ursodeoxycholic acid (UDCA).

In one example, wherein the subject is a human.

In one aspect there is described a use of a therapeutically effective amount of mirtazapine or a functional derivative thereof for treating a subject having an autoimmune disease, a subject suspected of having an autoimmune disease, or a subject at risk of having autoimmune disease.

In one aspect there is described a use of a therapeutically effective amount of mirtazapine or a functional derivative thereof in the manufacture of a medicament for treating a subject having an autoimmune disease, a subject suspected of having an autoimmune disease, or a subject at risk of having autoimmune disease.

In one example, wherein the autoimmune disease is Addison's disease, alopecia areata, ankylosing spondylitis, autoimmune hepatitis, autoimmune parotitis, autoimmune thyroiditis, autoimmune gastritis, autoimmune adrenalitis, autoimmune hypoparathyriodism, autoimmune diabetes, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjögren's syndrome, spondyloarthropathies, thyroiditis, vasculitis, vitiligo, myxedema, pernicious anemia, ulcerative colitis, paraneoplastic neurological disorders such as Lambert-Eaton Myasthenic Syndrome, inflammatory bowel disease, sarcoidosis, Achalasia, Adult Still's disease, Agammaglobulinemia, Achalasia, Addison's disease, Adult Still's disease, Agammaglobulinemia, Amyloidosis, Anti-GBM/Anti-TBM nephritis, Antiphospholipid syndrome, Autoimmune angioedema, Autoimmune dysautonomia, Autoimmune encephalomyelitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Goodpasture's syndrome, Granulomatosis with Polyangiitis, Hashimoto's thyroiditis, Henoch-Schonlein purpura (HSP), Herpes gestationis or pemphigoid gestationis (PG), Hidradenitis Suppurativa (HS) (Acne Inverse), Hypogammalglobulinemia, IgA Nephropathy, IgG4-related sclerosing disease, Inflammatory bowel disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Schmidt syndrome, Scleritis, Systemic sclerosis, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Undifferentiated connective tissue disease (UCTD), Uveitis, Vogt-Koyanagi-Harada Disease or Wegener's granulomatosis (or Granulomatosis with Polyangiitis (GPA)).

In one example, further comprising use of ursodeoxycholic acid (UDCA).

In one example, wherein said subject is a human.

In one aspect there is described a use of a therapeutically effective amount of mirtazapine or a functional derivative thereof for increasing the number of Treg cells in a subject.

In one aspect there is described a use of a therapeutically effective amount of mirtazapine or a functional derivative thereof in the manufacture of a medicament for increasing the number of Treg cells in a subject.

In one aspect there is described use of a therapeutically effective amount of mirtazapine or a functional derivative thereof for increasing the number of Breg cells in a subject.

In one aspect there is described use of a therapeutically effective amount of mirtazapine or a functional derivative thereof in the manufacture of a medicament for increasing the number of Breg cells in a subject.

In one example, wherein the subject is a human.

In one aspect there is described use of a therapeutically effective amount of mirtazapine or a functional derivative thereof for treating a subject with a disease, disorder, or condition, that would benefit from an increase in the number of Tregs.

In one aspect there is described use of a therapeutically effective amount of mirtazapine or a functional derivative thereof in the manufacture of a medicament for treating a subject with a disease, disorder, or condition, that would benefit from an increase in the number of Tregs.

In one aspect there is described use of a therapeutically effective amount of mirtazapine or a functional derivative thereof for treating a subject with a disease, disorder, or condition, that would benefit from an increase in the number of Bregs.

In one aspect there is described use of a therapeutically effective amount of mirtazapine or a functional derivative thereof in the manufacture of a medicament for treating a subject with a disease, disorder, or condition, that would benefit from an increase in the number of Bregs.

In one example, wherein disease, disorder, or condition, is an inflammatory disorder, or autoimmune disease, or PBC.

In one example, wherein the inflammatory disorder is chronic inflammation, acute inflammation, Celiac Disease, rheumatoid arthritis (RA), Inflammatory Bowel Disease (IBD), asthma, encephalitis, chronic obstructive pulmonary disease (COPD), inflammatory osteolysis, Crohn's disease, ulcerative colitis, allergic disorders, septic shock, pulmonary fibrosis (e.g. idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, chronic inflammation resulting from chronic viral or bacterial infections, and acute inflammation, such as sepsis. In a particular embodiment, the immune-mediated inflammatory disease is selected from the group consisting of rheumatoid arthritis (RA), Inflammatory Bowel Disease (IBD), or Crohn's disease.

In one example, wherein the autoimmune disease is Addison's disease, alopecia areata, ankylosing spondylitis, autoimmune hepatitis, autoimmune parotitis, autoimmune thyroiditis, autoimmune gastritis, autoimmune adrenalitis, autoimmune hypoparathyriodism, autoimmune diabetes, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjögren's syndrome, spondyloarthropathies, thyroiditis, vasculitis, vitiligo, myxedema, pernicious anemia, ulcerative colitis, paraneoplastic neurological disorders such as Lambert-Eaton Myasthenic Syndrome, inflammatory bowel disease, sarcoidosis, Achalasia, Adult Still's disease, Agammaglobulinemia, Achalasia, Addison's disease, Adult Still's disease, Agammaglobulinemia, Amyloidosis, Anti-GBM/Anti-TBM nephritis, Antiphospholipid syndrome, Autoimmune angioedema, Autoimmune dysautonomia, Autoimmune encephalomyelitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Goodpasture's syndrome, Granulomatosis with Polyangiitis, Hashimoto's thyroiditis, Henoch-Schonlein purpura (HSP), Herpes gestationis or pemphigoid gestationis (PG), Hidradenitis Suppurativa (HS) (Acne Inverse), Hypogammalglobulinemia, IgA Nephropathy, IgG4-related sclerosing disease, Inflammatory bowel disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Schmidt syndrome, Scleritis, Systemic sclerosis, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Undifferentiated connective tissue disease (UCTD), Uveitis, Vogt-Koyanagi-Harada Disease or Wegener's granulomatosis (or Granulomatosis with Polyangiitis (GPA)).

In one example, further comprising use of ursodeoxycholic acid (UDCA).

In one example, wherein said subject is a human.

In one aspect there is described a method for treating graft-versus-host disease (GVHD) in a subject, comprising administering a therapeutically effective amount of mirtazapine or a functional derivative thereof.

In one example, further comprising administering one or more or obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, or tetrathiomolybdate.

In one example, wherein said subject is a human.

In one aspect there is described a method of treating a subject to prevent or reduce rejection of transplantation of an organ in a subject, comprising administering a therapeutically effective amount of mirtazapine or a functional derivative thereof.

In one example, further comprising administering one or more or obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, or tetrathiomolybdate.

In one example, wherein said organ is a kidney, a liver, a heart, a lung, or a pancreas.

In one example, wherein said subject is a human.

In one aspect there is described use of a therapeutically effective amount of mirtazapine or a functional derivative thereof for treating graft-versus-host disease (GVHD) in a subject.

In one aspect there is described use of a therapeutically effective amount of mirtazapine or a functional derivative thereof in the manufacture of a medicament for treating graft-versus-host disease (GVHD) in a subject.

In one example, further comprising administering one or more or obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, or tetrathiomolybdate.

In one example, wherein said subject is a human.

In one aspect there is described use a therapeutically effective amount of mirtazapine or a functional derivative thereof for treating a subject to prevent or reduce rejection of transplantation of an organ in a subject.

In one aspect there is described use of administering a therapeutically effective amount of mirtazapine or a functional derivative thereof in the manufacture of a medicament for treating a subject to prevent or reduce rejection of transplantation of an organ in a subject.

In one example, further comprising use of one or more or obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, or tetrathiomolybdate.

In one example, wherein said organ is a kidney, a liver, a heart, a lung, or a pancreas.

In one example, wherein said subject is a human.

In one aspect there is described a kit, comprising: mirtazapine or a functional derivative thereof, a container, and optionally instructions for the use thereof.

In one example, further comprising ursodeoxycholic acid (UDCA).

In one example, further comprising one or more or obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, or tetrathiomolybdate.

BRIEF DESCRIPTION OF THE FIGURES

Embodiments of the present disclosure will now be described, by way of example only, with reference to the attached Figures.

DETAILED DESCRIPTION

Figure 1:
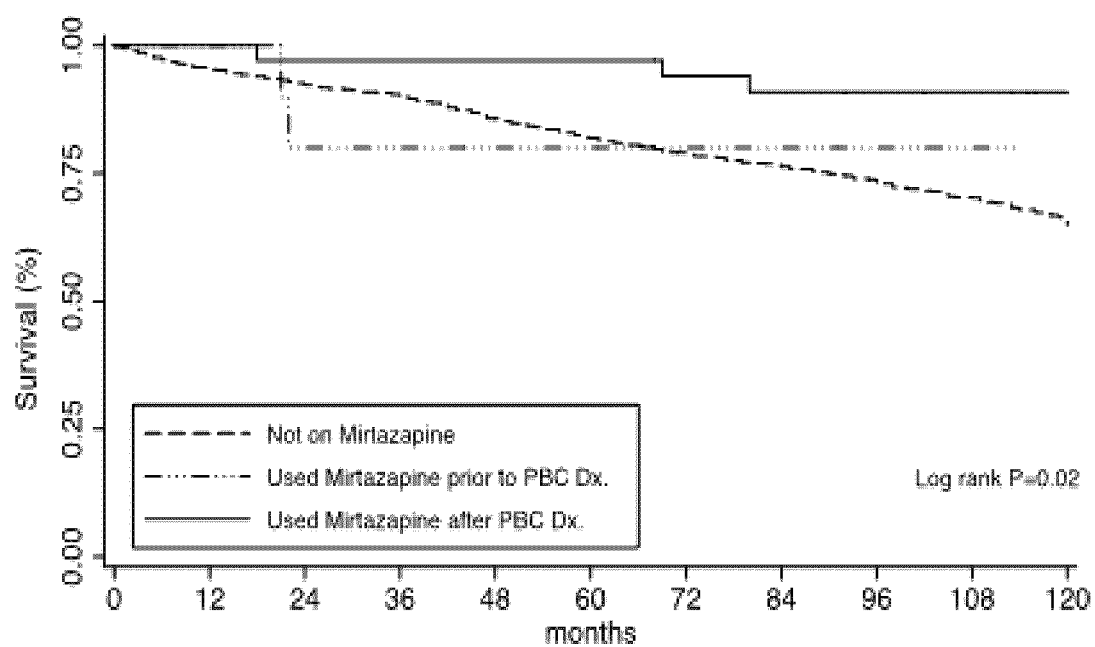
FIG. 1. Kaplan-Meier curves indicating 10-year decompensation, liver transplant and mortality free survival among PBC patients according to Mirtazapine usage.

In one aspect, there is described compounds, compositions, methods, and uses, for the treatment of a subject having an inflammatory disorder, a subject suspected of having an inflammatory disorder, or a subject at risk of having an inflammatory disorder.

In one aspect, there is described compounds, compositions, methods, and uses, for the treatment of a subject having an autoimmune disease, a subject suspected of having an autoimmune disease, or a subject at risk of having an autoimmune disease. mirtazapine is used in a method of treatment of use In one aspect, there is described compounds, compositions, methods, and uses, for the treatment of a subject having primary biliary cholangitis, a subject suspected of having primary biliary cholangitis, or a subject at risk of having primary biliary cholangitis.

The term "subject", as used herein, refers to an animal, and can include, for example, domesticated animals, such as cats, dogs, etc., livestock (e.g., cattle, horses, pigs, sheep, goats, etc.), laboratory animals (e.g., mouse, rabbit, rat, guinea pig, etc.), mammals, non-human mammals, primates, non-human primates, rodents, birds, reptiles, amphibians, fish, and any other animal. The subject may be an infant, a child, an adult, or elderly. In a specific example, the subject is a human.

The term "treatment" or "treat" as used herein, refers to obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable.

"Treating" and "Treatment" can also mean prolonging survival as compared to expected survival if not receiving treatment.

"Treating" and "treatment" as used herein also includes prophylactic treatment. For example, a subject in the early stage of disease can be treated to prevent progression or alternatively a subject in remission can be treated with a compound or composition described herein to prevent progression. Alternately, a subject at risk of developing disease may be treated with a compound or composition described herein to prevent or reduce progression.

In some examples, treatment methods comprise administering to a subject a therapeutically effective amount of a compound or composition described herein and optionally consists of a single administration or application, or alternatively comprises a series of administrations or applications.

In one example treatment is in vitro treatment. In one example the treatment is in vivo treatment. In one example, treatment is ex vivo.

The term "pharmaceutically effective amount" as used herein refers to the amount of a compound, composition, drug or pharmaceutical agent that will elicit the biological or medical response of a tissue, system, animal or human that is being sought by a researcher or clinician, for example, the treatment of progressive multiple sclerosis. This amount can be a therapeutically effective amount.

The compounds and compositions may be provided in a pharmaceutically acceptable form.

The term "pharmaceutically acceptable" as used herein includes compounds, materials, compositions, and/or dosage forms (such as unit dosages) which are suitable for use in contact with the tissues of a subject without excessive toxicity, irritation, allergic response, or other problem or complication, commensurate with a reasonable benefit/risk ratio. Each carrier, excipient, etc. is also "acceptable" in the sense of being compatible with the other ingredients of the formulation.

In some examples, treatment methods comprise administering to a subject a therapeutically effective amount of a compound or composition described herein and optionally consists of a single administration or application, or alternatively comprises a series of administrations or applications.

Treatments may be administered either simultaneously (or substantially simultaneously) or sequentially.

The compounds and compositions may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot/for example, subcutaneously or intramuscularly.

The actual amount(s) administered, and rate and time-course of administration, will depend on the nature and severity of the disease or condition being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

The term "inflammatory disease" also referred to as "inflammatory disorder", refers to a condition in a subject characterized by inflammation. Accordingly, the term "inflammatory disorder" refers, for example, to a disease characterized by inflammation which is a fundamental pathologic process, for example consisting of a dynamic complex of histologically apparent cytological changes, cellular infiltration, and mediator release that occurs in the affected tissue vessels and/or adjacent tissues in response, to non-limiting examples of, an injury or abnormal stimulation caused by a physical, chemical, or biologic agent, including the local reactions and resulting morphologic changes; the destruction or removal of the injurious material; and the responses that lead to repair and healing.

Examples of inflammatory disorder, include, but are not limited to chronic inflammation and acute inflammation. Additional, non-limiting examples of inflammatory disorders include, but are not limited to, Celiac Disease, rheumatoid arthritis (RA), Inflammatory Bowel Disease (IBD), asthma, encephalitis, chronic obstructive pulmonary disease (COPD), inflammatory osteolysis, Crohn's disease, ulcerative colitis, allergic disorders, septic shock, pulmonary fibrosis (e.g. idiopathic pulmonary fibrosis), inflammatory vacultides (e.g. , polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, chronic inflammation resulting from chronic viral or bacterial infections, and acute inflammation, such as sepsis. In a particular embodiment, the immune-mediated inflammatory disease is selected from the group consisting of rheumatoid arthritis (RA), Inflammatory Bowel Disease (IBD), and Crohn's disease.

Risk factors of inflammatory disorders include, but are not limited to, disease symptoms, pathological characteristics, family history, diet, environmental factors or lifestyle factors.

The term "autoimmune disease" as used herein refers to any group of disorders in which tissue injury is associated with humoral or cell-mediated responses to the body's own constituents. Thus, the term autoimmune disease encompasses disorders that result from an autoimmune response.

In a specific example, the autoimmune disease is primary biliary cirrhosis (PBC). In a specific example, mirtazapine is used in a method of treatment or use in treatment of primary biliary cirrhosis of a subject. In a specific example, the subject is a human.

Additional examples of autoimmune diseases include, but are not limited to, Addison's disease, alopecia areata, ankylosing spondylitis, autoimmune hepatitis, autoimmune parotitis, autoimmune thyroiditis, autoimmune gastritis, autoimmune adrenalitis, autoimmune hypoparathyriodism, autoimmune diabetes, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjögren's syndrome, spondyloarthropathies, thyroiditis, vasculitis, vitiligo, myxedema, pernicious anemia, ulcerative colitis, paraneoplastic neurological disorders such as Lambert-Eaton Myasthenic Syndrome, inflammatory bowel disease, sarcoidosis, Achalasia, Adult Still's disease, Agammaglobulinemia, Achalasia, Addison's disease, Adult Still's disease, Agammaglobulinemia, Amyloidosis, Anti-GBM/Anti-TBM nephritis, Antiphospholipid syndrome, Autoimmune angioedema, Autoimmune dysautonomia, Autoimmune encephalomyelitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Goodpasture's syndrome, Granulomatosis with Polyangiitis, Hashimoto's thyroiditis, Henoch-Schonlein purpura (HSP), Herpes gestationis or pemphigoid gestationis (PG), Hidradenitis Suppurativa (HS) (Acne Inverse), Hypogammalglobulinemia, IgA Nephropathy, IgG4-related sclerosing disease, Inflammatory bowel disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Schmidt syndrome, Scleritis, Systemic sclerosis, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Undifferentiated connective tissue disease (UCTD), Uveitis, Vogt-Koyanagi-Harada Disease or Wegener's granulomatosis (or Granulomatosis with Polyangiitis (GPA)).

Risk factors of autoimmune disease include, but are not limited to, disease symptoms, pathological characteristics, family history, diet, environmental factors or lifestyle factors.

The term "primary biliary cholangitis", also referred to as "primary biliary cirrhosis", and abbreviated PBC, is an autoimmune disease of the liver marked by the slow progressive destruction of the small bile ducts of the liver, with the intralobular ducts (Canals of Hering) affected early in the disease. When these ducts are damaged, bile builds up in the liver (cholestasis) and over time damages the tissue. This can lead to scarring, fibrosis and cirrhosis. Primary biliary cirrhosis is characterized by interlobular bile duct destruction. Histopathologic findings of primary biliary cirrhosis include: inflammation of the bile ducts, characterized by intraepithelial lymphocytes, and periductal epithelioid granulomata. There are 4 stage of PBC.

Stage 1—Portal Stage: Normal sized triads; portal inflammation, subtle bile duct damage. Granulomas are often detected in this stage.

Stage 2—Periportal Stage: Enlarged triads; periportal fibrosis and/or inflammation. Typically this stage is characterized by the finding of a proliferation of small bile ducts.

Stage 3—Septal Stage: Active and/or passive fibrous septa.

Stage 4—Biliary Cirrhosis: Nodules present; garland

PBC is commonly associated with extrahepatic symptoms that can be debilitating and can include altered mood (e.g. depression, anxiety) and social withdrawal. Risk factors for PBC include, but are not limited to, environmental factors, and exogenous factors.

Other examples of immune mediated diseases of the liver include, but are not limited to primary sclerosing cholangitis (PSC), autoimmune hepatitis, alcoholic hepatitis, and non-alcoholic fatty liver disease.

In some examples, the compounds and compositions described herein may be useful in transplantation, including but not limited to, kidney, liver, heart, pancreas and/or lung transplantation, or hematopoietic stem cell transplantation.

In some examples, the compounds and compositions described herein may be useful in the treatment of immune-mediated graft vs host disease.

In one example, mirtazapine or a functional derivative thereof is used in the treatment of a subject having an inflammatory disorder, a subject suspected of having an inflammatory disorder, or a subject at risk of having an inflammatory disorder.

In one example, mirtazapine or a functional derivative thereof is used in the treatment of a subject having an autoimmune disease, a subject suspected of having an autoimmune disease, or a subject at risk of having an autoimmune disease.

In one example, mirtazapine or a functional derivative thereof is used in the treatment of a subject having primary biliary cholangitis, a subject suspected of having primary biliary cholangitis, or a subject at risk of having primary biliary cholangitis.

In one example, there is described the use of mirtazapine or a functional derivative thereof in the treatment of a subject having an inflammatory disorder, a subject suspected of having an inflammatory disorder, or a subject at risk of having an inflammatory disorder.

In one example, there is described the use of mirtazapine or a functional derivative thereof in the treatment of a subject having an autoimmune disease, a subject suspected of having an autoimmune disease, or a subject at risk of having an autoimmune disease.

In one example, there is described the use of mirtazapine or a functional derivative thereof in the treatment of a subject having primary biliary cholangitis, a subject suspected of having primary biliary cholangitis, or a subject at risk of having primary biliary cholangitis.

The term "functional derivative" and "physiologically functional derivative" as used herein means an active compound with equivalent or near equivalent physiological functionality to the named active compound when used and/or administered as described herein. As used herein, the term "physiologically functional derivative" includes any pharmaceutically acceptable salts, solvates, esters, prodrugs derivatives, enantiomers, or polymorphs.

In some examples the compounds are prodrugs.

The term "prodrug" used herein refers to compounds which are not pharmaceutically active themselves but which are transformed into their pharmaceutical active form in vivo, for example in the subject to which the compound is administered.

Regulatory T cells (Tregs) play an important role in preventing autoimmunity, limiting immunopathology and maintaining immune homeostasis.

In one example, there is described the use mirtazapine or a functional derivative thereof in increasing the number of Tregs in a subject.

In one aspect, there is described the use of mirtazapine or a functional derivative thereof in treating a subject with a disease, disorder, or condition, that would benefit from an increase in the number of Tregs.

In one example, disease, disorder, or condition, includes chronic inflammatory, allergic and autoimmune diseases, and for patients post-transplantation.

In other examples, the disease, disorder, or conditions includes, but is not limited to, an inflammatory disorder, an autoimmune disease, or PBC.

In a specific example, the disease, disorder, or condition, includes autoimmune diseases, Type 1 diabetes [T1DM], inflammatory bowel disease [IBD], rheumatoid arthritis [RA], psoriasis, and multiple sclerosis, and beneficially suppress inflammation and tissue damage in solid organ transplantation, graft vs host disease and allergic responses Regulatory B cells (Bregs), such as B1a B cells, play a role in, for example, autoimmune disorders.

In one example, there is described the use mirtazapine or a functional derivative thereof in increasing the number of Bregs in a subject.

In one aspect, there is described the use of mirtazapine or a functional derivative thereof in treating a subject with a disease, disorder, or condition, that would benefit from an increase in the number of Bregs, and in one example B1a B cells.

In one example, disease, disorder, or condition, includes chronic inflammatory, allergic and autoimmune diseases, and for patients post-transplantation.

In other examples, the disease, disorder, or condition includes, but is not limited to, an inflammatory disorder, an autoimmune disease, or PBC.

The compounds and/or compositions described herein may be administered in combination with other treatment(s).

The other treatment(s), may be administered either simultaneously (or substantially simultaneously) or sequentially.

For example, a therapeutic agent may be administered in combination with the compound herein. In one example, mirtazapine or a functional derivative thereof is used in combination with a therapeutic agent.

The term "therapeutic agent", as used herein, refers to an agent useful in the treatment of a disease. In a particular embodiment, the additional therapeutic agent is a known drug for the treatment of, for example, an inflammatory disorder, an autoimmune disease, or PBC.

In one example, the therapeutic agent comprises ursodeoxycholic acid (UDCA).

In another example, the therapeutic agent comprises obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, or tetrathiomolybdate.

In one example, mirtazapine or a functional derivative thereof, and UDCA, are used in the treatment of a subject having an inflammatory disorder, a subject suspected of having an inflammatory disorder, or a subject at risk of having an inflammatory disorder.

In another example, mirtazapine or a functional derivative thereof, and UDCA, and one or more of obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, ortetrathiomolybdate, is used in the treatment of a subject having an inflammatory disorder, a subject suspected of having an inflammatory disorder, or a subject at risk of having an inflammatory disorder.

In another example, mirtazapine or a functional derivative thereof, and UDCA are used in the treatment of a subject having an autoimmune disease, a subject suspected of having an autoimmune disease, or a subject at risk of having an autoimmune disease.

In another example, mirtazapine or a functional derivative thereof, UDCA, and one or more of obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, or tetrathiomolybdate, are used in the treatment of a subject having an autoimmune disease, a subject suspected of having an autoimmune disease, or a subject at risk of having an autoimmune disease.

In another example, mirtazapine or a functional derivative thereof, and UDCA, are used in the treatment of a subject having primary biliary cholangitis, a subject suspected of having primary biliary cholangitis, or a subject at risk of having primary biliary cholangitis.

In another example, mirtazapine or a functional derivative thereof, and UDCA, and one or more of obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, or tetrathiomolybdate, are used in the treatment of a subject having primary biliary cholangitis, a subject suspected of having primary biliary cholangitis, or a subject at risk of having primary biliary cholangitis.

Method of the invention are conveniently practiced by providing the compounds and/or compositions used in such method in the form of a kit. Such kit preferably contains the composition. Such a kit preferably contains instructions for the use thereof.

To gain a better understanding of the invention described herein, the following examples are set forth. It should be understood that these examples are for illustrative purposes only. Therefore, they should not limit the scope of this invention in anyway.

EXAMPLES

Example 1

Primary biliary cholangitis (PBC) is a prototypic autoimmune disease, characterized by immune-mediated destruction of small bile ducts within the liver[1]. This immune attack, mainly mediated by activated T cells, contributes to hepatocyte injury and the slowly progressive development of liver fibrosis[1]. The bile acid ursodeoxycholic acid (UDCA) has been the only available therapy for PBC for over two decades. Unfortunately, 30% to 40% of patients with PBC do not fully respond to UDCA and are at risk of progressing to cirrhosis, liver failure, and death[2].

PBC is commonly associated with extrahepatic symptoms that can be debilitating and can include altered mood (e.g. depression, anxiety) and social withdrawal[1,3] In fact, depressive symptoms occur in up to 40% of PBC patients, and in one study 15% of PBC patients were prescribed anti-depressants[3,4]. However, the effect of depressive symptoms, or related therapeutic interventions, on disease outcomes in PBC patients is unknown. Despite being typically used to treat alterations in mood, anti-depressants can also affect the immune system and modulate inflammatory responses[5-7]. A potential protective effect of anti-depressants during inflammation may involve the differential regulation of cytokines or chemokine signaling networks, or immune cell recruitment, which are important for initiating, sustaining, or resolving tissue injury.

In our current study, we used data extracted from a large clinical database to examine the effect of depression and anti-depressant medications on the hepatic outcomes of PBC patients, including hepatic decompensation, transplantation, and death. Following this clinical analysis, we used a mouse experimental model to mechanistically define the role of the atypical anti-depressant mirtazapine in regulating a variety of immune regulatory networks within the liver and the associated impact of changes in these networks on liver injury in a model of immune-mediated liver disease.

Methods

Part I: Population-Based Epidemiological Studies

Study Design and Patient Data Source.

We conducted a cohort study using The Health Improvement Network (THIN). THIN is one of the largest medical databases in the UK[8], consisting of prospectively gathered electronic medical records from over 11.1 million patients[8]. Patients registered in THIN have demographic and mortality distribution comparable to the general the UK population[9,10]. Data from participant general practitioners across the UK is exported to the THIN administrators and database, which is updated every 3 months[11]. The THIN database records demographic data and clinical events using Read codes, prescription medications, and laboratory values[12].

Study Population and Outcomes

Figure 10:
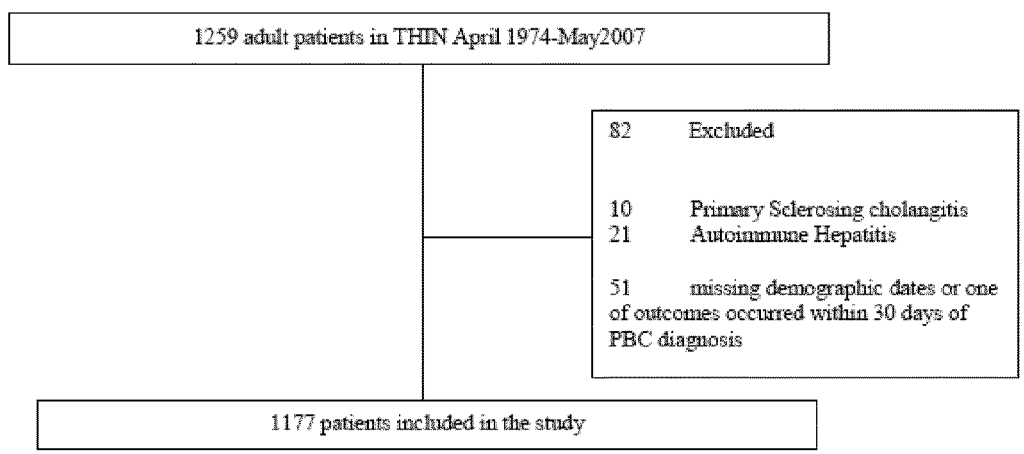
FIG. 10 depicts a flow diagram of identified PBC patients in The Health Improvement Network between April 1974 and May 2007.

We identified patients with PBC Read code "J6160" from April 1974 until May 2007. This cohort was followed until May 2012. We excluded patients having overlap syndrome with autoimmune hepatitis or primary sclerosing cholangitis. The first code of PBC identified in the THIN database was considered the index (ie. diagnosis) date. FIG. 10 provides a flow diagram illustrating the selection of the study population. The primary outcome was the first occurrence of one of the three events following the diagnosis of PBC: (1) decompensation of cirrhosis (ascites, spontaneous bacterial peritonitis, hepatic encephalopathy, hepatorenal syndrome, variceal bleeding, jaundice, or hepatocellular carcinoma); (2) liver transplantation; or (3) death.

Exposure Variables of Interest

Read codes were used to identify patients with chronic depression disorder. Chronic depression was defined as follows: (1) never diagnosed with chronic depression; (2) past depression diagnosis prior to 90 days from PBC diagnosis; and (3) current depression diagnosis if a diagnosis was made within 90 days before or after a PBC diagnosis. Using THIN database therapy files, we assessed the impact of anti-depressant medications on outcomes of PBC patients (mortality, decompensation, and liver transplant). For each anti-depressant medication, use was defined as follows: (1) never used the medication; (2) past use as defined as a previous code for medication use prior to 90 days of PBC diagnosis; and (3) current medication user if the medication code was identified within 90 days before or after a PBC diagnosis. We assessed the effect of each anti-depressant medication on study outcomes separately. Antidepressants were classified as typical or atypical and stratified accordingly. Atypical antidepressants include: Agomelatine, Bupropion and Mirtazapine. While typical antidepressants include the following groups: (a) Selective Serotonin Reuptake Inhibitors (SSRI): Citalopram, Escitalopram, Fluoxetine, Fluvoxamine, Paroxetine and Sertraline; (b) Selective-Norepinephrine Reuptake Inhibitors (SNRI): Desvenlafaxine, Duloxetine, Minacipran and Venlafaxine; (c) Serotonin modulators: Nefazodone, Trazodone and Vilazodone; (d) Tricyclics and tetracyclics: Amitriptyline, Amoxapine, Clomipramine, Desipramine, Doxepin, Imipramine, Maprotiline, Nortriptyline and Protriptyline, Trimiprramine; (e) Monamine oxidase inhibitors: Isocarboxazid, Phenelzine, Selegiline and Tranylcypromine.

Study Covariates

We assessed age at diagnosis of PBC, sex, and the presence of coexisting liver disease (ie. chronic hepatitis either viral, alcoholic, or fatty liver disease; yes/no). Smoking status was classified (current, former, never smoked, or unknown status) at the time of PBC diagnosis, alcohol consumption was classified (current, former, never consumed alcohol, or unknown status) at PBC diagnosis. Ursodeoxycholic acid (UDCA) usage (ever/never recorded) was also determined.

Data Analysis

In our primary analysis, we assessed demographic, clinical, and medication variables in the PBC cohort according to depression status. Where appropriate, we used the Fisher Exact test or Chi-Square test for categorical data, and the Kruskal-Wallis or Student's t-test for continuous data. Univariate analysis using Log Rank test and multivariate Cox Proportional Regression models were used to assess the impact of depression or anti-depressant medications on PBC outcomes as defined by death, decompensated cirrhosis, or liver transplant. Each outcome was studied separately in sensitivity analyses. In all our models, we adjusted for age, sex, UDCA usage, and depression status. Estimates were reported as hazard ratios (HR) and accompanying 95% confidence intervals (CIs). The proportional hazard model assumption was tested and not violated in any models.

Sensitivity Analysis

To assess the validity of our findings, we restricted the study population to PBC patients who were only using UDCA. We did different survival analyses to identify survival predictors in each of our study outcomes separately (cirrhosis decompensation, liver transplant, mortality). All analyses were performed using Stata 14.1 (StateCorp, College Station, Tex.) using alpha of 0.05. Both the Conjoint Health Research Ethics Board at the University of Calgary and The Scientific Review Committee of THIN approved the study protocol.

Part II: Animal Studies

Animals and Hepatic Effects of Mirtazapine Treatment

Male 8-10 week old C57BL/6 mice (Jackson Labs, Bar Harbor, Me.) were used. All procedures were approved by the University of Calgary Animal Care Committee (protocol numbers AC14-0129 and AC14-0128) and were performed in accordance with the guidelines of the Canadian Council on Animal Care. To delineate the impact of mirtazapine treatment upon liver immune cell numbers and phenotype, and upon cytokine/chemokine networks within the liver, mice were treated with mirtazapine 1-20 mg/kg intraperitoneally[13-15]. Mirtazapine was suspended in 1% aqueous solution of Tween 80, whereas the control group received 1% aqueous solution of Tween 80. Blood and liver samples were collected 5 hours post-mirtazapine treatment (or 16 hours post-Con A treatment). The detailed experimental protocols, lists of antibodies and reagents used, flow cytometry gating, and immune cell phenotyping strategies, are described herein.

Impact of Mirtazapine Treatment in a Mouse Model of Immune-Mediated Liver Disease To determine whether mirtazapine treatment alters subsequent immune-mediated liver injury, we used the mouse model of concanavalin (Con A) hepatitis. The Con A model is a widely used and well characterized model of immune-mediated T cell-driven liver injury[16, 17]. Mice were treated with mirtazapine 20 mg/kg ip and 1 hour later Con A (Sigma, St. Louis, Mo.) or PBS vehicle was injected intravenously at a dose of 13.5 mg/kg[17]. Mice were sacrificed 16 hours following Con A administration and hepatitis determined biochemically (ALT) and histologically (H & E staining)[17, 18]. In addition, to further characterize the effects of mirtazapine in the Con A model, we performed a mirtazapine dose response study with mirtazapine doses of 1, 10, and 20 mg/kg ip given 1 hour prior to Con A treatment.

Statistical Analyses for Mouse Studies.

All data are shown as mean±standard error of the mean (SEM). For comparisons between two groups, an unpaired Student's t-test was used. For comparisons between more than two groups, an analysis of variance followed by the Student-Newman-Keuls post-hoc test was performed. When data were not normally distributed, the Mann-Whitney test was used for comparisons between two groups, and the Kruskal-Wallis test followed by Dunn's post-hoc test for comparisons between more than 2 groups (Graph-Pad V5, San Diego, Calif.).

Antibodies and Other Reagents

The following reagents, antibodies and their appropriate isotype controls were obtained from indicated sources: Percoll® (GE HealthCare Biosciences, Quebec, Canada), protease inhibitor cocktail (Sigma-Aldrich, St. Louis, Mo.); RPMI 1640 medium, HEPES, fetal bovine serum (FBS), UltraPure™ DNase/RNase-Free Distilled Water and phosphate-buffered saline (Thermo Fisher Scientific, MA, USA); Mouse CXCL10/IP-10/CRG-2 Antibody, Polyclonal Goat IgG (R&D Systems. Minneapolis, Minn., USA). LEGENDplex™ Mouse Capture Beads (CXCL9 (MIG) and CXCL10 (IP-10), anti-mouse CD11b (M1/70), anti-mouse CD11c (N418), anti-mouse CD73 (TY/11.8) (BioLegend, CA, U.S.A). Fixation buffer, Fixation/Permeabilization concentrate, anti-mouse CD16/CD32 (93), anti-mouse CD5 (53-7.3), anti-mouse IgM, (eB121-15F9), anti-mouse CD3e (145-2C11), anti-mouse CD4 (RM4-4), ani-mouse CD45 (30-F11), anti-mouse LY6C (HK1.4), anti-mouse Foxp3 (FJK-16s), anti-mouse CXCR3 (CXCR3-173), anti-mouse CD25 (PC61.5) (eBioscience. San Diego, Calif., USA). CXCL10/IP-10/CRG-2 Antibody (Clone 6D4) (Novus Biologicals, Littleton, USA). Mirtazapine (CAS No: 85650-52-8; Tocris Bioscience, Bristol, United Kingdom). TWEEN® 80 (Proteomics grade CAS Number: 9005-65-6; Amresco LLC, OH, USA). Anti-mouse VCAM1 antibody (EPR5047), anti-mouse rabbit polyclonal CXCL9/MIG antibody, anti-mouse ICAM1 antibody (YN1/1.7.4), antigen retrieval buffer (EDTA Buffer, pH 8.0), antigen retrieval buffer (Citrate Buffer pH 6.0) (Abcam, Cambridge, UK). Avidin/Biotin Blocking Kit, ImmPACT NovaRED Peroxidase (HRP) substrate, Vecstain Elite ABC HRP Kit (Peroxidase, Standard), biotinylated goat anti-Rat IgG Antibody, biotinylated goat anti-Rabbit IgG Antibody, biotinylated rabbit anti-Goat IgG Antibody, permanent non-aqueous mounting medium, normal goat serum, normal rabbit serum (Vector Laboratories Inc., CA, USA).

Sample Collection/Preparation and Experimental Methods.

(i) Blood Samples:

Whole blood was drawn directly from the heart into EDTA-treated tubes. Blood samples were kept on ice until processed and plasma was isolated and stored at −20° C. until analyzed.

(ii) Isolation of Hepatic Immune Cells:

5 hrs post-mirtazapine/vehicle treatment livers were perfused with 20 ml ice cold PBS before removal and processing for intrahepatic immune cell isolation (methods as previously described)[18, 66].

(iii) Clinical Chemistry and Histology/Immunohistochemistry (IHC) Evaluation of Liver Sections:

To assess liver injury, plasma alanine aminotransferase (ALT) activity was measured (Roche-Hitachi Modular-P800 apparatus; Roche, Mannheim, Germany). Additionally, formalin-fixed liver tissue slices were stained with Hematoxylin and Eosin (H&E) for microscopic examination. Extent of liver parenchymal necrosis was quantitated as previously described [18], using an Olympus XC10 camera (acquired using the Olympus VS-ASW software package; original magnification ×400). Images were later processed and selected images obtained at 25 or 50% magnification (corresponding to magnifications of 100x and 200X, respectively).

Hepatic CXCL10/IP-10, CXCL9/MIG, ICAM-1 and VCAM-1 expression were determined using immunohistochemistry, as previously described [66]. Briefly, following initial deparaffinization and rehydration of tissue sections, antigen retrieval was performed in 1x Citrate buffer, PH 6.0 (Abcam) for IP-10/CXCL9 and MIG/CXCL9, or in 1X EDTA buffer pH 8.0 for ICAM1 and VCAM-1. In all cases slides were incubated in antigen retrieval buffer at 95-100° C. for 20 minutes. Endogenous peroxidase and endogenous biotin were blocked using 3% $H_2O_2$ and an avidin/biotin blocking kit (Vector Laboratories, Burlingame, Calif.) respectively, and then incubated with primary antibodies (Rabbit IgG polyclonal against MIG at 1:200; polyclonal goat IgG against IP-10/CXCL10 at 1:40; rat monoclonal against ICAM-1 clone YN1/1.7.4 at 1:200; and rabbit monoclonal against VCAM1 clone EPR5047 at 1:1000) overnight at 4° C. This was followed by incubation with biotinylated rabbit anti-goat, goat-anti rat or goat anti-rabbit secondary antibodies (at 1:150) for 1 hour at room temperature (Vector Labs). Negative staining controls were performed by omission of primary antibody, or by omission of both primary and secondary antibodies. In all cases, negative controls showed insignificant staining. This was followed by incubation with Vectastain Elite ABC kit (Vector Laboratories) for 30 min at room temperature. Color was developed with Nova Red Chromogen (ImmPACT NovaRED Peroxidase Substrate, Vector Lab, Burlingame, Calif.), after which sections were counterstained with hematoxylin (EMD Millipore). Mounted slides were converted to virtual slides with a BX61 VS virtual microscopy system equipped with an XC10 camera and VS ASW software (Olympus) (original magnification ×400). For ICAM-1, VCAM1, CXCL9/Mig, and CXCL10/IP10 expression, all scanned virtual slides of the sections were examined in a blinded fashion, and expression patterns evaluated and described.

(iv) Hepatic Cytokine/Chemokine Measurement:

To delineate the effect of mirtazapine treatment on hepatic cytokine/chemokine expression a Luminex® assay was used using methods as previously described [18]. Livers were collected 5 hours after mirtazapine or vehicle treatment. A panel of mouse cytokines/chemokines were simultaneously measured in liver homogenate samples using a mouse MILLIPLEX kit (Millipore, USA) according to the manufacturer's protocol. The multiplexing analysis was performed using the Luminex 100 system (Luminex®, USA; Eve Technologies Corporation, Calgary, Canada). Total protein concentrations in liver homogenates were quantified using a BCA Protein Assay kit (Pierce, USA) according to manufacturers instructions. Results were expressed as pg of analyte per mg of protein. Additional plasma and hepatic measurements were made using a bead-based LEGENDplex immunoassay. Plasma and hepatic levels of CXCL10/IP-10 and CXCL9/Mig were measured using BioLegend's LEGENDplex™ bead-based immunoassays in a 96-well v-bottom microplate, according to the manufacturer's protocol. At the end of the assay, all samples were transferred from the plate to FACS tubes and read on a flow cytometer (Attune® Acoustic Focusing Cytometer). After data acquisition, flow cytometry standard (FCS) files were analyzed using Biolegend's LEGENDplex data analysis software to calculate the concentrations of individual chemokines, and results were expressed as pg of analyte per mg of protein. Alternatively, the flow cytometry standard (FCS) files were analyzed using FlowJo software (Treestar, San Carlos, Calif.).

(v) Hepatic Immune Cell Phenotyping Flow Cytometry and Gating Strategies:

Isolated hepatic leukocytes were subjected to direct immunofluorescence analyses using multicolor flow cytometry staining as previously described [18, 66, 67]. Samples were acquired either using a FACScan flow cytometer (Becton Dickinson, Mountain View, Calif.) or Attune™ Acoustic Focusing flow cytometer (Applied Biosytems, Mainway, Burlington, ON). Data were analyzed using FlowJo® software (Treestar, Ashland, Oreg.). Gating proceeded as follows: gating of live cells and exclusion of duplet cells followed by gating on forward scatter (FSC) and side scatter (SSC) areas to identify regions appropriate to define live leukocytes. Within the leukocyte gate, the following cell subsets were identified: Regulatory T cells ($CD4^+CD25^+Foxp3^+$), monocytes ($CD11b^+Ly6C^+$), dendritic cells ($CD11b^+CD11c^+$), B Cells ($CD3^-IgM^+$), B1a B cells ($IgM^+CD5^+CD^{11}b^+$), B1b B cells ($IgM^+CD5^-CD11b^+$), and B2 B cells as ($IgM^+CD5^-CD11b^-$) [23, 24].

Fluorescence-minus-one (FMO) controls were used for the accurate designation of cells with fluorescence above background levels [18]. Appropriate isotype controls were used to determine the specificity of all antibodies used. Cell numbers were calculated based on the percentage of cells found in the gate of interest, and total cell numbers isolated from each liver.

Results
Part I: Patient-Based Epidemiological Studies

Cohort Characteristics. We identified 1,177 patients with a diagnosis of PBC from April 1974 to May 2007. In this cohort, 86 patients (7.3%) were diagnosed with chronic depression prior to the diagnosis of PBC, while 79 patients (6.7%) had a depression diagnosis after their diagnosis with PBC. The demographic and clinical characteristics of PBC patients according to depression status are shown in Table 1. PBC patients with prior or current depression were younger (median age 59 and 58 versus 63 years, P=0.009) and more commonly female (93% and 96% versus 87%, P=0.02). Prevalence of coexisting liver disease was similar among the three groups (P=0.19), Table 1.

TABLE 1

Patients characteristics according to depression status

| Characteristic | PBC-No depression cohort n = 1,012 (86.0%) | PBC-Previous depression cohort n = 86 (7.3%) | PBC-Current depression cohort n = 79 (6.7%) | P-value |
|---|---|---|---|---|
| Age at diagnosis | 63 (53-72) | 59 (50-71) | 58 (47-69) | 0.009 |
| Female Gender | 87.1% (881) | 93.0% (80) | 96.2% (76) | 0.02 |
| *Smoking* | | | | |
| Current | 16.9% (171) | 19.8% (17) | 20.3% (16) | |
| Ex-smoker | 36.0% (364) | 45.4% (39) | 32.9% (26) | 0.32 |
| No smoking | 41.1% (416) | 32.6% (28) | 43.0% (34) | |
| Unknown | 6.0% (61) | 2.3% (2) | 3.8% (3) | |
| *Alcohol* | | | | |
| Current | 50.1% (507) | 54.7% (47) | 48.1% (38) | |
| Ex-usage | 25.6% (259) | 29.1% (25) | 29.1% (23) | 0.48 |
| Never | 10.0% (101) | 9.3% (8) | 6.3% (5) | |
| Unknown | 14.3% (145) | 7.0% (6) | 16.5% (13) | |
| Coexisting Liver disease | 4.6% (46) | 8.1% (7) | 7.6% (6) | 0.19 |
| URSO usage | 67.9% (687) | 60.5% (52) | 68.4% (54) | 0.36 |
| Ascites | 3.7% (37) | 1.2% (1) | 1.3% (1) | 0.27 |
| SBP | 0.3% (3) | 0 | 0 | 0.76 |
| HE | 0.6% (7) | 0 | 0 | 0.61 |
| Varices | 8.8% (89) | 4.7% (4) | 7.6% (6) | 0.40 |
| HRS | 0.2% (2) | 0 | 0 | 0.85 |
| HCC | 1.0% (10) | 0 | 0 | 0.44 |
| Jaundice | 0.4% (4) | 0 | 1.3% (1) | 0.43 |
| Follow up period, in months | 91 (56-141) | 75 (47-113) | 133 (85-172) | <0.001 |
| Decompensated Cirrhosis | 12.6% (127) | 5.8% (5) | 8.9% (7) | 0.13 |
| Liver transplant | 3.9% (39) | 1.2% (1) | 2.5% (2) | 0.24 |
| Death | 27.1% (274) | 19.8% (17) | 26.6% (21) | 0.34 |
| *Antidepressants* | | | | |
| Current usage | 24.6% (249) | 26.7% (23) | 82.3% (65) | <0.001 |
| Previous usage | 11.1% (112) | 45.4% (39) | 7.6% (6) | |
| *Antidepressants subgroups: SSRI* | | | | |
| Current usage | 11.8% (119) | 14.0% (12) | 65.8% (52) | <0.001 |
| Previous usage | 7.5% (76) | 50.0% (43) | 17.7% (14) | |
| *SNRI* | | | | |
| Current usage | 1.6% (16) | 2.3% (2) | 12.7% (10) | <0.001 |
| Previous usage | 0.7% (7) | 4.7% (4) | 1.3% (1) | |
| *Atypical* | | | | |
| Current usage | 2.8% (28) | 4.7% (4) | 7.6% (6) | <0.001 |
| Previous usage | 0.9% (9) | 9.3% (8) | 1.3% (1) | |
| *Serotonin Modulators* | | | | |
| Current usage | 1.0% (10) | 2.3% (2) | 2.5% (2) | <0.001 |
| Previous usage | 0.8% (8) | 2.3% (2) | 1.3% (1) | |
| *Tricyclic/Tetracyclic* | | | | |
| Current usage | 14.5% (147) | 10.5% (9) | 21.5% (17) | <0.001 |
| Previous usage | 8.8% (89) | 33.7% (29) | 13.9% (11) | |
| *MOI* | | | | |
| Current usage | 0 | 0 | 0 | |
| Previous usage | 0 | 0 | 0 | |
| *Mirtazapine* | | | | |
| Current usage | 2.7% (27) | 3.5% (3) | 6.3% (5) | <0.001 |
| Previous usage | 0.4% (4) | 8.1% (7) | 0 | |

Data is presented as percentage and numbers for categorical data or median and interquartile range for continuous data.

Clinical Outcomes.

Approximately 70% of PBC patients were prescribed UDCA, and this use did not differ by depression status (see Table 1). In our cohort, the cumulative incidence of mortality at 3, 5, and 10 years was 6.5%, 13.4%, and 25.4%, respectively. The cumulative incidence of decompensated cirrhosis and liver transplant at 3, 5, and 10 years were 4.1%, 6.6%, 13.0% and 0.1%, 2.0%, 4.0%, respectively. During a median follow-up of 92 months (range: 58-143 months), overall decompensated cirrhosis, liver transplant, and mortality rates were similar among our study groups (overall mortality: 27.1% for non-depression cohort, 19.8% for previously diagnosed with depression, and 26.6% for currently depressed patients, P=0.34).

Anti-Depressant Medication Usage.

Usage of anti-depressant medications was variable among our study groups (see Table 1). Interestingly, 24.6% of patients who had never had a diagnosis of depression were using anti-depressants after their PBC diagnosis, while 11.1% used anti-depressants prior to their PBC diagnosis. Mirtazapine was prescribed at a lower rate for patients with no history of depression (2.7%) or with previous depression diagnosis (3.5%), compared to current depression diagnosis (6.3%), P<0.001. Details on anti-depressant usage are shown in Table 1.

Impact of Depression and Anti-Depressants on PBC Patient Survival.

After adjusting for age, gender, UDCA usage, alcohol intake, depression status, and assessing for each of the aforementioned anti-depressant classes and drugs separately, mirtazapine was associated with a decreased risk of decompensated cirrhosis, transplantation, or death (Table 2). In our adjusted models, using mirtazapine after PBC diagnosis was significantly protective (Adjusted HR 0.23: 95% CI 0.07-0.72) against poor outcomes (decompensation, liver transplant, mortality). See Table 2 and FIG. 1.

TABLE 2

Predictors of 10-year decompensation, liver, transplant and mortality free survival in PBC cohort

| Variable | Univariate HR | Multivariate model-1 (include age, gender, alcohol, URSO, depression, antidepressants) | Multivariate model-2$ (include age, gender, alcohol, URSO, depression, mirtazapine) |
|---|---|---|---|
| Age at diagnosis | 1.05 (1.04-1.06) | 1.05 (1.04-1.06) | 1.05 (1.04-1.06) |
| Female Gender | 0.83 (0.60-1.14) | 0.93 (0.67-1.29) | 0.92 (0.67-1.28) |
| Smoking | | | |
| Current vs other categories | 1.03 (0.77-1.38) | — | — |
| Alcohol | | | |
| Current vs other categories | 0.77 (0.61-0.96) | 0.82 (0.66-1.03) | 0.82 (0.66-1.03) |
| Coexisting Liver disease | 1.30 (0.82-2.08) | — | — |
| Depression diagnosis | | | |
| None | Ref | Ref | Ref |
| Prior to PBC diagnosis | 0.82 (0.51-1.30) | 0.81 (0.50-1.31) | 0.84 (0.52-1.35) |
| Current | 0.52 (0.31-0.87) | 0.65 (0.38-1.12) | 0.60 (0.35-1.00) |
| URSO usage | 0.80 (0.64-1.00) | 1.00 (0.79-1.26) | 1.00 (0.79-1.27) |
| Antidepressants | | | |
| None | Ref | Ref | |
| Prior to PBC diagnosis | 1.04 (0.74-1.46) | 1.10 (0.78-1.57) | — |
| Current | 0.68 (0.52-0.87) | 0.79 (0.60-1.04) | |
| SSRI | | | |
| None | Ref | | |
| Prior to PBC diagnosis | 0.73 (0.49-1.09) | | |
| Current | 0.76 (0.56-1.03) | | |
| SNRI | | | |
| None | Ref | | |
| Prior to PBC diagnosis | 1.55 (0.58-4.17) | | |
| Current | 0.74 (0.35-1.57) | | |
| Atypical | | | |
| None | Ref | | |
| Prior to PBC diagnosis | 0.71 (0.23-2.23) | | |
| Current | 0.27 (0.10-0.73) | | |
| Serotonin Modulators | | | |
| None | Ref | | |
| Prior to PBC diagnosis | 0.31 (0.04-2.17) | | |
| Current | 0.46 (0.11-1.85) | | |
| Tricyclic/Tetracyclic | | | |
| None | Ref | | |
| Prior to PBC diagnosis | 1.20 (0.85-1.69) | | |
| Current | 0.74 (0.53-1.02) | | |

TABLE 2-continued

Predictors of 10-year decompensation, liver, transplant and mortality free survival in PBC cohort

| Variable | Univariate HR | Multivariate model-1 (include age, gender, alcohol, URSO, depression, antidepressants) | Multivariate model-2$ (include age, gender, alcohol, URSO, depression, mirtazapine) |
|---|---|---|---|
| Mirtazapine* | | | |
| None | Ref | | Ref |
| Prior to PBC diagnosis | 0.84 (0.21-3.39) | | 0.94 (0.23-3.94) |
| Current | 0.22 (0.07-0.69) | | 0.23 (0.07-0.72) |
| Fluoxetine* | | | |
| None | Ref | | |
| Prior to PBC diagnosis | 0.83 (0.50-1.37) | | |
| Current | 0.58 (0.36-0.92) | | |

*After adjusting for age at diagnosis, female gender, using of URSO, depression status, and alcohol intake. Fluoxetine was not significant while Mirtazapine remained significant in multivariate model
$There was no interaction between Mirtazapine and depression status.

Sensitivity Analysis.

First, we limited our cohort to only patients who were using UDCA (n=793, 67.4%). In adjusted Cox Regression models, current usage of mirtazapine was protective against decompensated cirrhosis, liver transplant, and mortality (Adjusted HR 0.21: 95% CI 0.05-0.83).

We assessed mirtazapine as an independent predictor for each of our outcomes separately (cirrhosis decompensation, liver transplant, and mortality). Current usage of mirtazapine was a significant predictor of mortality (Adjusted HR 0.22: 95% CI 0.05-0.89), but not liver decompensation (Adjusted HR 0.22: 95% CI 0.03-1.60). None of the PBC patients who had ever used mirtazapine required liver transplant in our cohort.

Part II: Animal Studies

Mirtazapine Treatment Profoundly Alters the Hepatic Cytokine and Chemokine Milieu.

Figure 2:
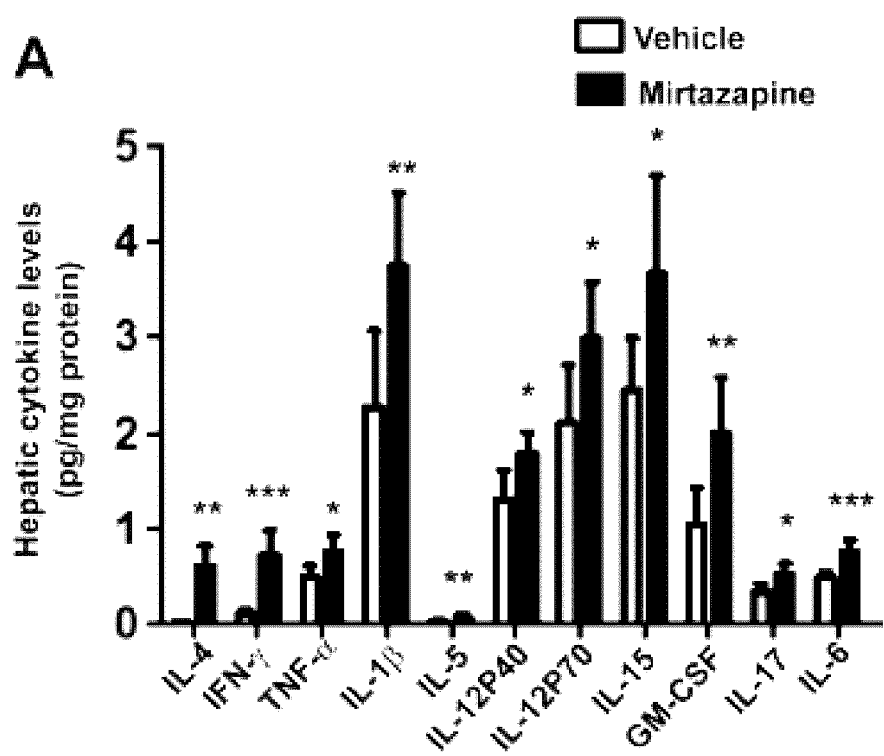
FIG. 2. Mirtazapine administration significantly alters the hepatic cytokine and chemokine milieu. (A) Mirtazapine treatment significantly increased hepatic levels of a number of cytokines, compared to vehicle treated animals, including IL-4, IFN-γ, TNF-α, IL-1β, IL-5, IL-12p40, IL-12p70, IL-15, GM-CSF, IL-17 and IL-6; *p≤0.0001, p≤0.01, * p≤0.05; n=6-7 mice/group. (B) Plasma and hepatic levels of the chemokines CXCL10 and CXCL9 are significantly elevated post-mirtazapine treatment, relative to vehicle treated controls. *p≤0.0001, p≤0.01; n=6-7 mice/group. (C and D) Immunohistochemical (IHC) analysis of liver sections demonstrating cellular sources of CXCL10 and CXCL9 in livers of mice treated with mirtazapine vs vehicle. Panels show representative images from n=5 mice/group. (C, left panel) Negative staining control slide. (C, middle) CXCL10 expression was detected in vehicle treated mice primarily within hepatocytes (double head arrow) and immune cells (single head arrow). (C, right panel) Hepatic CXCL10 expression is clearly upregulated in both hepatocytes (double head arrow) and along hepatic sinusoids (arrow head) in mirtazapine-treated mice. (D, left panel) Negative staining control slides. (D, middle panel) IHC analysis shows hepatic CXCL9 expression primarily within hepatocytes (double head arrow) and immune cells (single head arrow) in vehicle treated mice, and (D, right panel) clear upregulation of hepatic CXCL9 expression, mainly within hepatocytes (double head arrow) in mirtazapine-treated mice (All images in FIG. 2C, D were acquired at original magnification of 400X, and representative images extracted at 50 percent view corresponding to 200X). Flow cytometry analyses of isolated hepatic immune cells demonstrate that mirtazapine treatment enhances (E) dendritic cell and (F) monocyte per cell CXCL10 production (as MFI), vs vehicle treated controls. *p≤0.05; n 4 and 5 mice/group).
Figure 2:
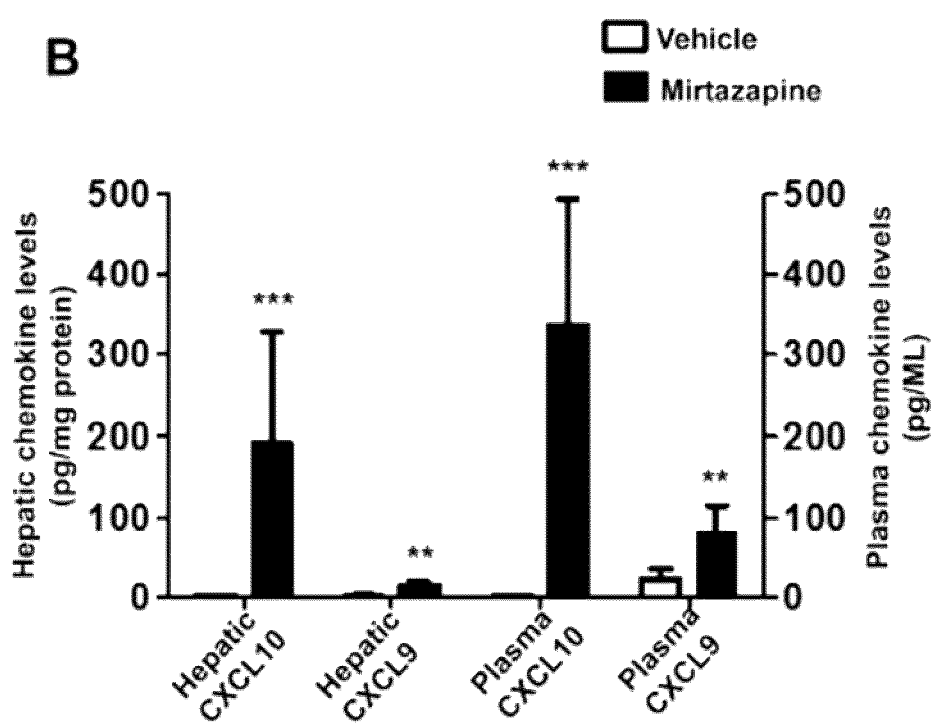
Figure 2:
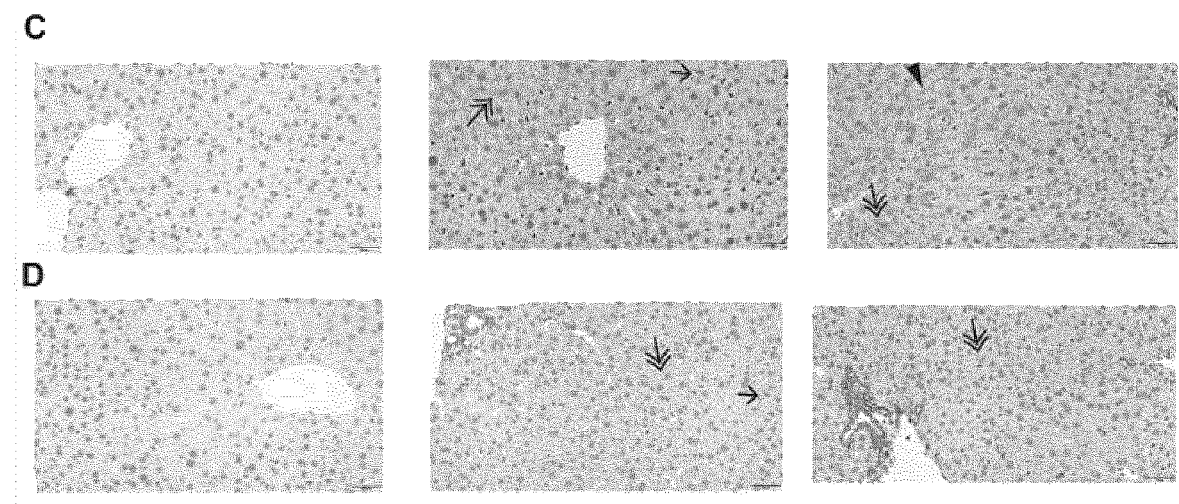
Figure 2:
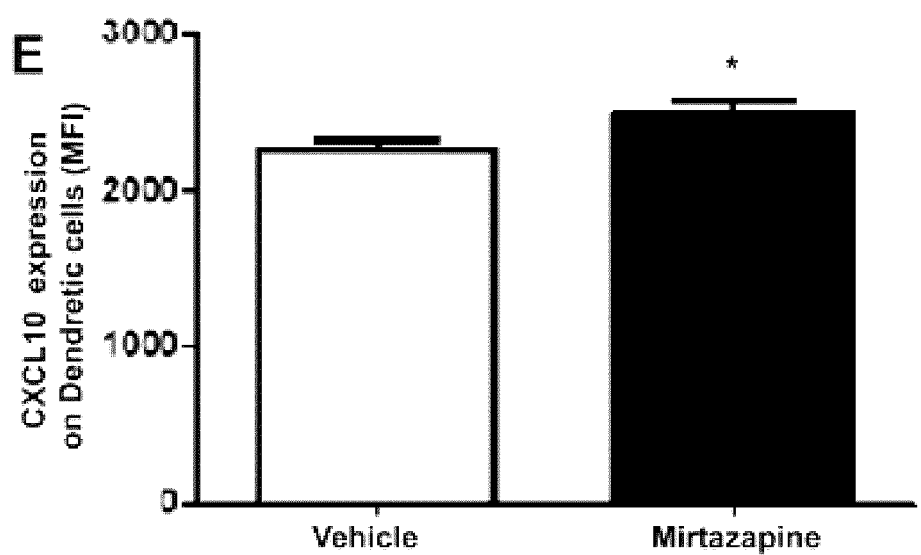
Figure 2:
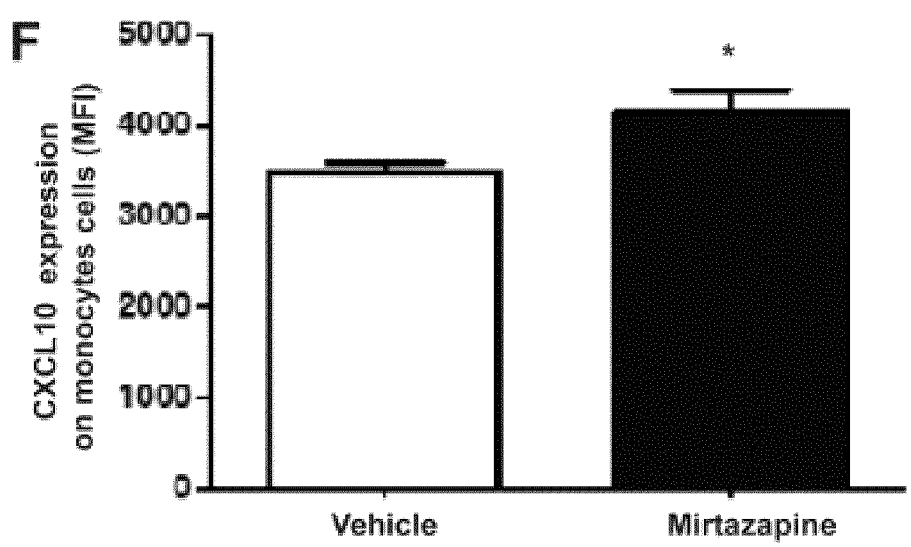

Treatment of mice with mirtazapine resulted in significant increases in hepatic levels of numerous cytokines and chemokines. Specifically, mirtazapine-treated mice had significant increases in hepatic levels of IL-4 (~30-fold), IFNγ (~8-fold), IL-5 (~2-fold), (TNFα/IL-1β/I/IL-12p40/IL-12p70/IL-15/IL-6/GM-CSF, and IL-17 (all ~1.5-fold) vs. hepatic levels in vehicle treated mice (FIG. 2A). Moreover, mirtazapine treatment caused striking increases in hepatic levels of the chemokines CXCL10/IP-10 and CXCL9/MIG vs. vehicle treated controls (FIG. 2B). In contrast, hepatic levels of cytokines IL-2, IL-10, IL-13, IL-7, IL-9, M-CSF, G-CSF, LIF, or IL-3, and chemokines CCL3/MIP-1α, CCL4/MIP-1β, CXCL2/MIP-2, CCL11/Eotaxin-1, or CCL5/RANTES were unaltered by mirtazapine treatment (data not shown). Plasma levels of CXCL10/IP-10 and CXCL9/MIG were also significantly increased after mirtazapine treatment (FIG. 2B). We characterized hepatic expression patterns of CXCL10/CXCL9 using immunohistochemistry and immune cell types producing CXCL10 by flow cytometry.

Hepatic CXCL10 and CXCL9 expression was readily identified in livers of vehicle treated mice (mainly hepatocytes but also immune cells located in hepatic sinusoids) (FIG. 2C,D, middle panels). Mirtazapine treatment increased CXCL9 staining mainly within hepatocytes (FIG. 2D, right panel). Mirtazapine treatment strikingly increased CXCL10 expression in both hepatocytes and sinusoidal endothelium (FIG. 2C, right panel). Using flow cytometry, we found increased CXCL10 expression in hepatic monocytes and dendritic cells after mirtazapine treatment (as mean fluorescence intensity: MFI) (FIG. 2E,F). Mirtazapine treatment did not induce liver injury as reflected by serum ALT levels or histology (data not shown).

Mirtazapine Treatment Alters the Expression Patterns of Key Endothelial Adhesion Molecules ICAM-1 and VCAM-1 in Normal Liver.

Figure 3:
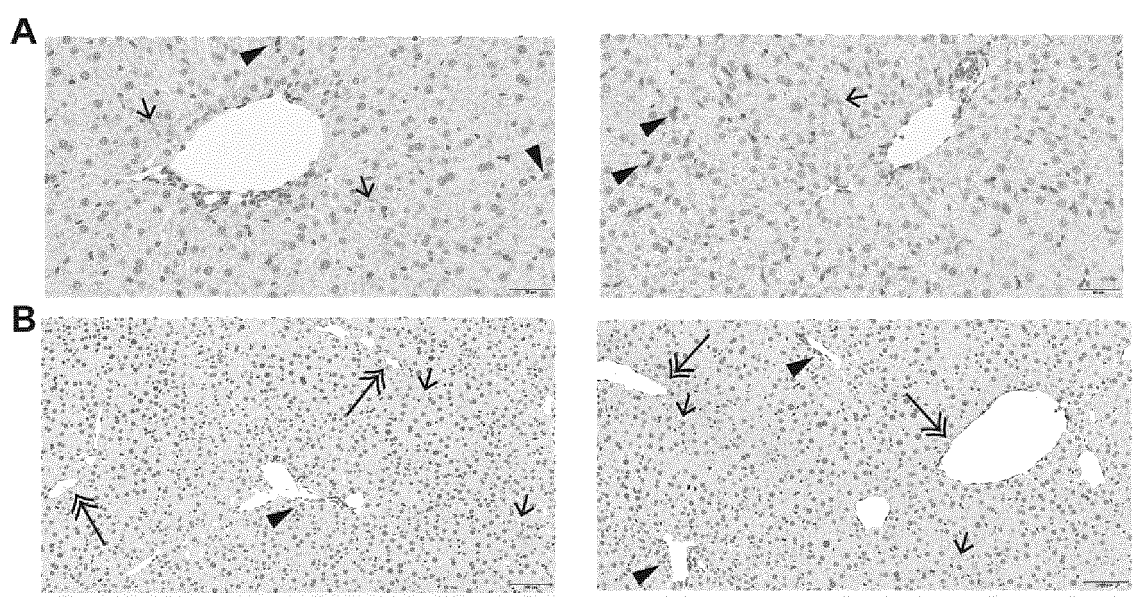
FIG. 3. Hepatic expression of the important immune cell homing adhesion molecules VCAM-1 and ICAM-1 are enhanced in mirtazapine treated mice. (A, left panel) Weak VCAM-1 expression (by IHC) detected on hepatic immune cells and sinusoidal endothelium in vehicle treated mice. (A, right panel) Mirtazapine treatment enhanced VCAM-1 expression in sinusoidal endothelium, and more strikingly on immune cells located within the hepatic sinusoids (representative images from n=5 mice per group). Arrows indicate sinusoidal endothelium, and black arrowheads indicated immune cells located within hepatic sinusoids. (B, left panel) Weak patchy sinusoidal expression, and robust central vein endothelium expression of ICAM-1 was detected (by IHC) in the liver of vehicle treated mice, whereas no ICAM-1 expression was detected in portal vein endothelium (B, left panel). (B, right panel) Hepatic ICAM-1 expression was not altered by mirtazapine treatment (representative images from n=5 mice per group). Arrows indicate sinusoidal endothelium, double head arrow indicates central vein endothelium, and black arrowhead indicates portal vein endothelium.

Immune cell recruitment, retention, and positioning within the liver are orchestrated through the differential expression of endothelial adhesion molecules and chemokines[19]. In vehicle treated mice we found patchy sinusoidal endothelial VCAM-1 expression and expression within sinusoid located immune cells (FIG. 3A, left panel). Mirtazapine treatment resulted in enhanced VCAM-1 staining intensity in sinusoidal endothelium and a marked increase in VCAM-1 expression intensity in sinusoidal immune cells (likely Kupffer cells) (FIG. 3A, right panel). Kupffer cells also express adhesion molecules, including VCAM-1[20] and ICAM-1[21]. Importantly, VCAM-1 expression by Kupffer cells mediates lymphocyte binding and induces Kupffer cell activation[20]. In contrast, ICAM-1 expression was weak and patchy within the hepatic sinusoids but was clearly evident in endothelium lining the central, but not portal, veins (FIG. 3B, left panel). Mirtazapine did not notably alter ICAM-1 expression (FIG. 3B, right panel).

Mirtazapine Treatment Shifts the Predominant Immune Cell Populations within the Liver Towards a More Regulatory Phenotype.

Figure 4:
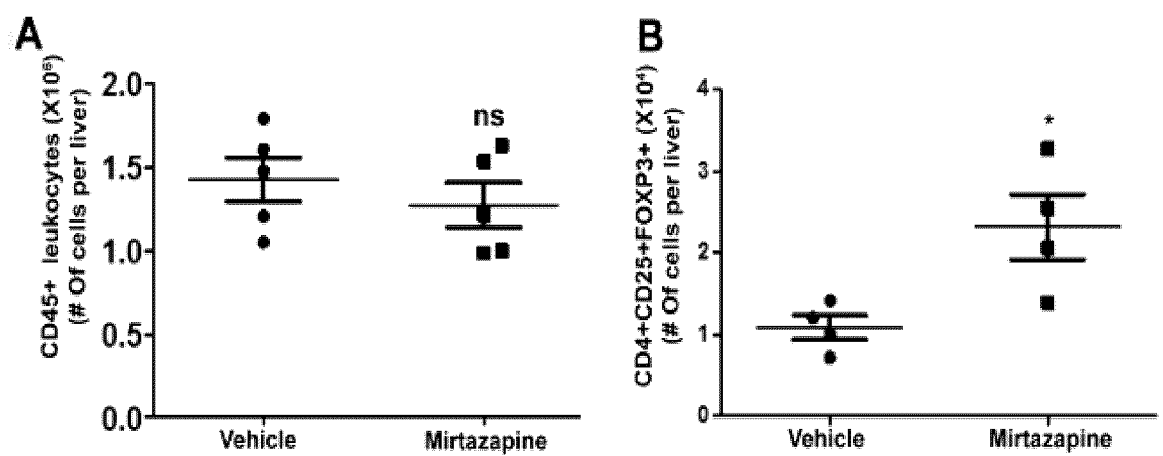
FIG. 4. Mirtazapine induces a shift in hepatic immune cells towards a more regulatory phenotype. (A) Mirtazapine treatment does not alter total hepatic immune cell numbers (as CD45+ leukocytes), compared to vehicle treated control mice, but results in a shift in immune cell subset populations. Data in panel (A) demonstrate that total hepatic leukocyte numbers were not altered 5 hrs post-Mirtazapine treatment, compared to vehicle treated controls (n=5 mice/group). (B) Increase in total hepatic numbers of CD4+CD25+Foxp3+ Tregs 5 hrs post-mirtazapine treatment, compared to vehicle treated controls (* p≤0.00272; n=4 mice/group). (C) Cellular expression levels of Foxp3 in hepatic CD4+ CD25+ cells (as MFI) are increased after mirtazapine treatment, compared to vehicle treated control mice (* p≤0.0478; n=4 mice/group). (D) Mirtazapine treatment alters hepatic B cell subpopulations as determined by flow cytometry. Mirtazapine treatment significantly increased hepatic B1a B cell (as IgM+CD5+CD11b+ cells) frequency, and reduced hepatic B2 B cell (as IgM+CD5−CD11b− cells) frequency, while B1b B cell (as IgM+CD5−CD11b+ cells) remain unchanged (* p≤0.0003,  p≤0.003; n=5 mice/group). (E) Mirtazapine treatment significantly increases hepatic numbers of B1a B cells that co-express the chemokine receptor CXCR3 and the ectoenzyme CD73, compared to vehicle treated controls (* p≤0.011; n=5 mice/group). (F) Mirtazapine treatment results in reduced total hepatic numbers of monocytes (as CD11b+LY6C+ mononuclear cells), compared to vehicle treated controls (* p≤0.0007; n=5 mice/group). (G) Mirtazapine treatment strikingly reduces hepatic numbers of classical inflammatory monocytes (as CD11b+Ly6Chi cells)(* p≤0.0003; n=5 mice/group), but also significantly reduces hepatic numbers of "repair" monocytes (as CD11b+Ly6Clow cells) (H), compared to vehicle treated mice (*p≤0.03; n=5 mice/group).
Figure 4:
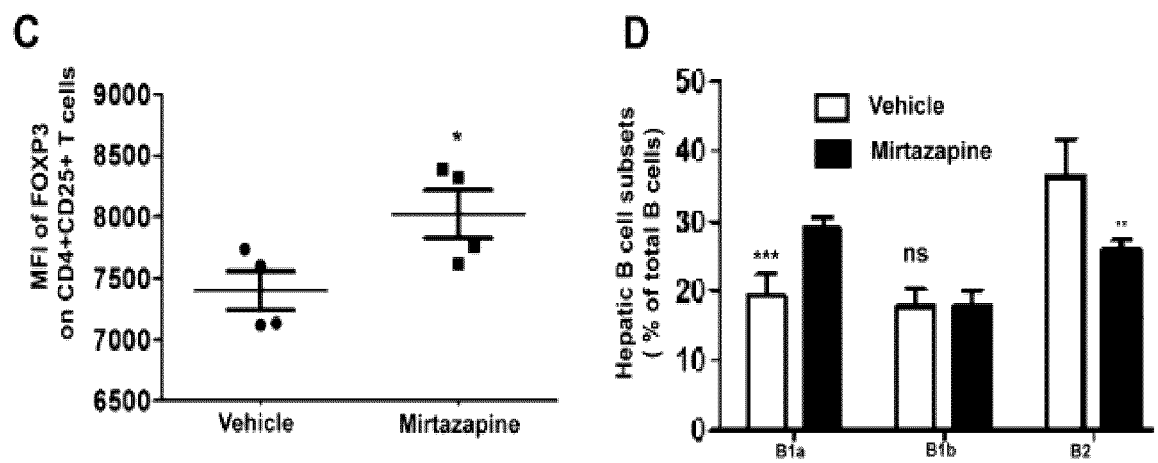
Figure 4:
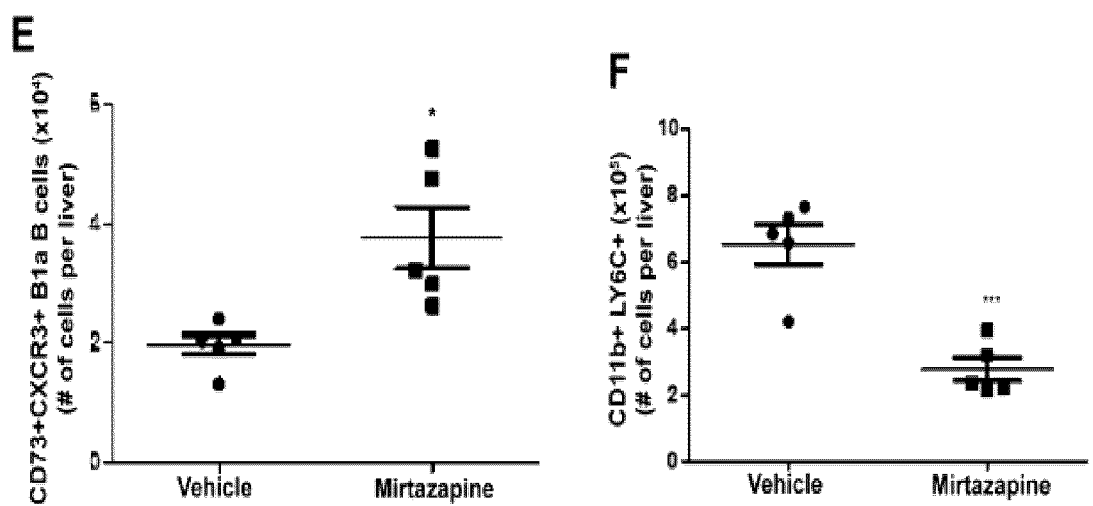
Figure 4:
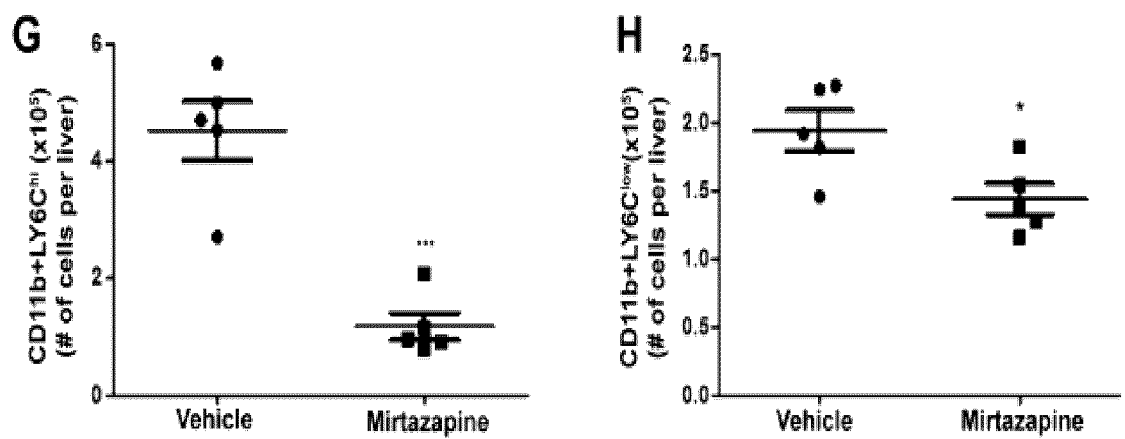

Mirtazapine treatment did not alter total overall hepatic leukocyte numbers vs. vehicle treated controls (FIG. 4A). Therefore, we performed a series of experiments to determine the potential impact of mirtazapine treatment on hepatic immune cell types with known immune-regulatory functions, including regulatory T cells (as FOXP3+ CD4+ CD25+ T cells)[22], B cell subtypes (B1 vs. B2)[23, 24] and inflammatory vs. repair monocytes (LY6Chi vs. LY6Clo)[26].

(i) Regulatory T Cells (Tregs):

Mirtazapine treatment significantly increased hepatic numbers (~2-fold) of CD4+CD25+FOXP3+ T cells (Tregs) (FIG. 4B) and also significantly increased expression intensity of FOXP3 per cell (as MFI) (FIG. 4C).

(ii) Hepatic B Cell Subtypes:

Murine B cells are typically divided into B2 cells, B1 cells (divided into B1a and B1b), and regulatory B cells (Bregs)[26]. B1a cells have received increasing attention for their immune-regulatory properties[27], including the production of the anti-inflammatory molecule adenosine via cell surface expression of the ectoenzyme CD73[18, 28, 29]. Mirtazapine treatment resulted in a significant increase in hepatic B1a cells and a decrease in hepatic B2 cells, whereas B1b cells remained unchanged (FIG. 4D). We have previously shown that B1a cells recruited to the liver express cell surface CD73 and the chemokine receptor CXCR3[18], and these B1a B cells potently suppress liver injury by producing adenosine[18]. Mirtazapine treatment significantly increased recruitment of CXCR3+CD73+B1a cells into the liver (FIG. 4E).

(iii) Inflammatory and Repair Monocytes within the Liver:

Monocytes can exhibit both pro-inflammatory and anti-inflammatory/repair properties[30]. Classical, pro-inflammatory monocytes are LY6Chi, circulate in the blood and are recruited into inflamed tissues[30]. In contrast, repair monocytes are $LY6C^{lo}$ and patrol along the endothelium of local blood vessels where they can participate in tissue repair[31]. However, within the liver, LY6Chi monocytes patrol the sinusoids, not LY6Clo monocytes[25]. Mirtazapine treatment resulted in a significant reduction in total numbers of hepatic monocytes (as CD11b+ LY6C+ cells) (FIG. 4F). However, mirtazapine treatment reduced the hepatic LY6Chi monocyte population to a greater extent (by ~2.5-fold) (FIG. 4G) than it did to the LY6Clo monocyte population (FIG. 4H).

Mirtazapine Treatment Markedly Attenuates Con A-Induced Hepatitis and Significantly Modulates Hepatic Cytokine, Chemokine and Adhesion Molecules Expression.

Figure 5:
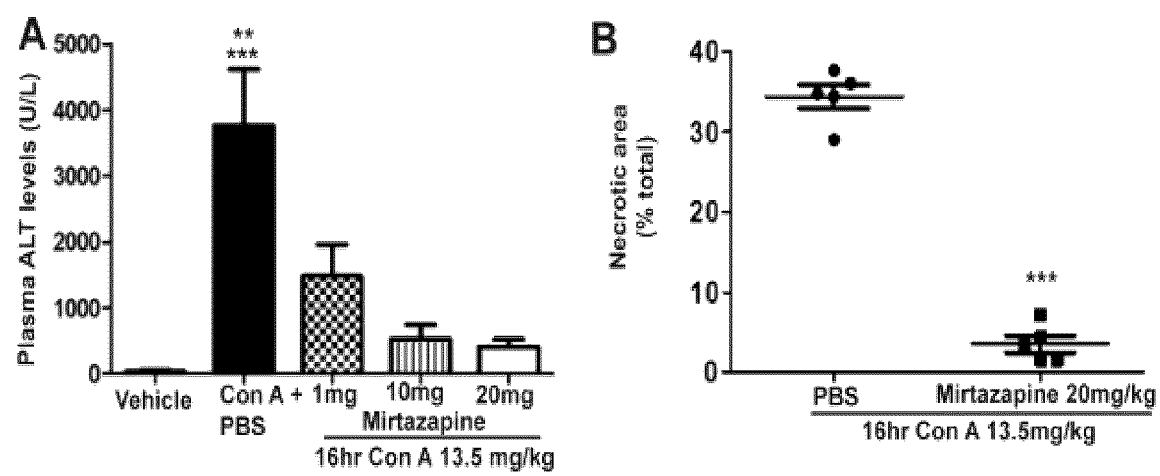
FIG. 5. Mirtazapine pretreatment profoundly attenuates ConA-induced immune-mediated hepatitis, and modulates hepatic cytokine/chemokine and adhesion molecule expression. (A) Administration of mirtazapine leads to a striking reduction in liver damage 16 hrs post-con A treatment, as reflected by plasma ALT levels (*p≤0.001 ConA+PBS group vs. vehicle, ConA+10 mg/kg Mirtazapine group, and ConA+20 mg/kg Mirtazapine groups; p≤0.01 ConA+PBS group vs ConA+1 mg/kg Mirtazapine group; n=4-5 mice/group), and (B) by quantification of histological damage in H&E stained liver sections (ie. as total area of liver cell necrosis). (C) Representative liver sections from con A treated mice (16 hrs post-con A) that received either PBS vehicle or mirtazapine (20 mg/kg). (C, left panel) ConA+PBS treated, and (C, right panel) ConA+20 mg/kg mirtazapine treated mice. Mice treated with ConA+PBS showed extensive liver cell necrosis (black arrowheads). In contrast, mice treated with ConA+mirtazapine showed only a minimal hepatocyte damage (images are 100 X). (D) Treatment with mirtazapine significantly attenuated con A-induced increases in hepatic levels of numerous cytokines compared to mice treated with con A alone; specifically, TNF-α, IFN-γ, IL-6, IL-9, and LIF. In contrast, mice treated with mirtazapine+con A have significantly higher hepatic levels of IL-10, compared to ConA+PBS treated mice. (*p≤0.0001, p≤0.01, * p≤0.05; n=6-7 mice/group). (E) In con A treated mice, mirtazapine treatment also significantly altered hepatic chemokine expression, enhancing con A-induced increases in hepatic CXCL-10 levels, and attenuating con A-induced increases in hepatic levels of CXCL9, CXCL2, CXCL1, CCL11, and CCL2, compared to con A+PBS treated mice (*p≤0.0001, p≤0.01, * p≤0.05; n=6-7 mice/group). (F) Con A treatment significantly enhanced hepatic VCAM1 expression (F, left panel); however, mirtazapine treatment did not appreciably alter hepatic VCAM-1 expression in the context of con A− mediated hepatitis (F, right panel). (G) Hepatic ICAM1 expression was strikingly increased after con A treatment (G, left panel), and mirtazapine administration profoundly attenuated this con A-induced increase in hepatic ICAM-1 expression (G, right panel). Portal veins are indicated by a single headed arrow, central veins by a double-headed arrow, immune cells by a black arrow head, and sinusoids by a black star.
Figure 5:
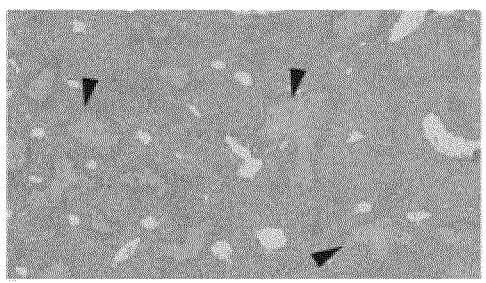
Figure 5:
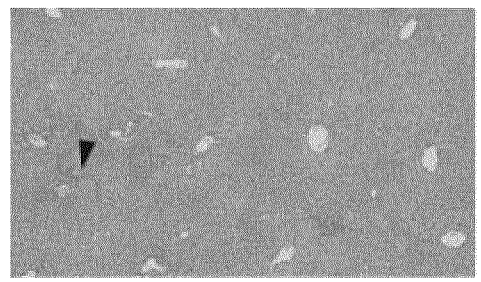
Figure 5:
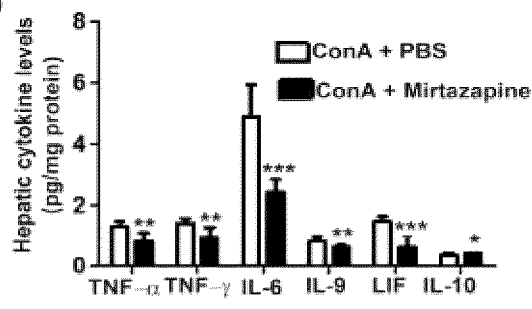
Figure 5:
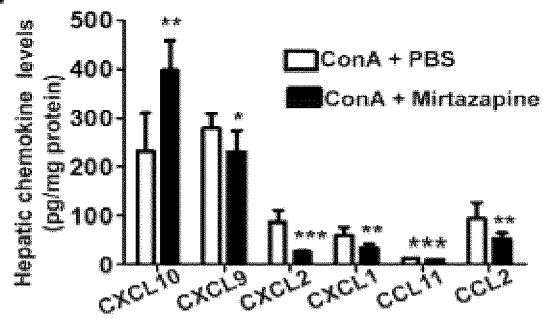
Figure 5:
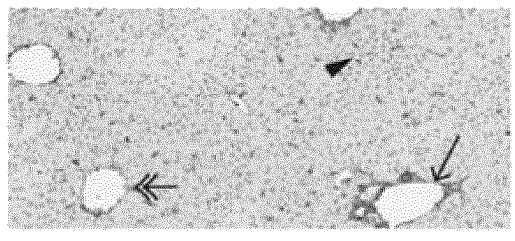
Figure 5:
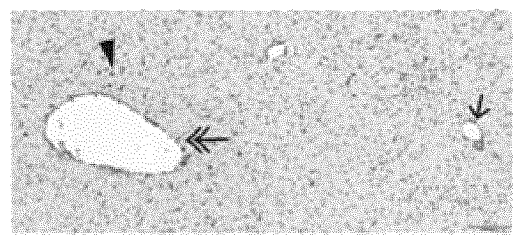
Figure 5:
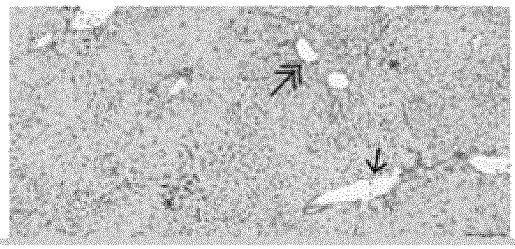
Figure 5:
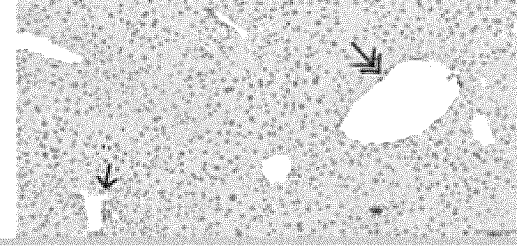
Figure 6:
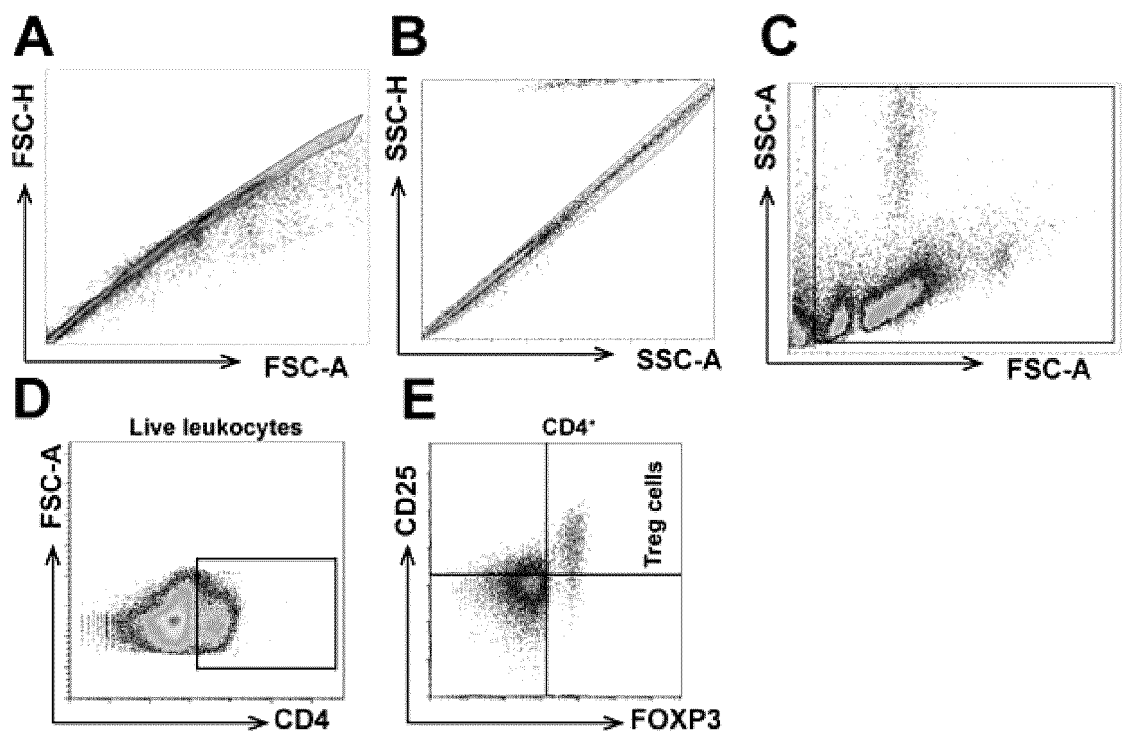
FIG. 6. Flow cytometry gating strategies for identifying hepatic regulatory T cells. To detect regulatory T cells gating proceeded as follows: Exclusion of duplet cells followed by gating on forward scatter (FSC) and side scatter (SSC) areas to identify regions appropriate to define all leukocytes, excluding cell debris (panels A-C). Within the leukocyte gate population CD4+ lymphocytes were identified (panel D). Regulatory T cells (Tregs) were then identified as CD4+CD25+FOXP3+ cells (panel E).
Figure 7:
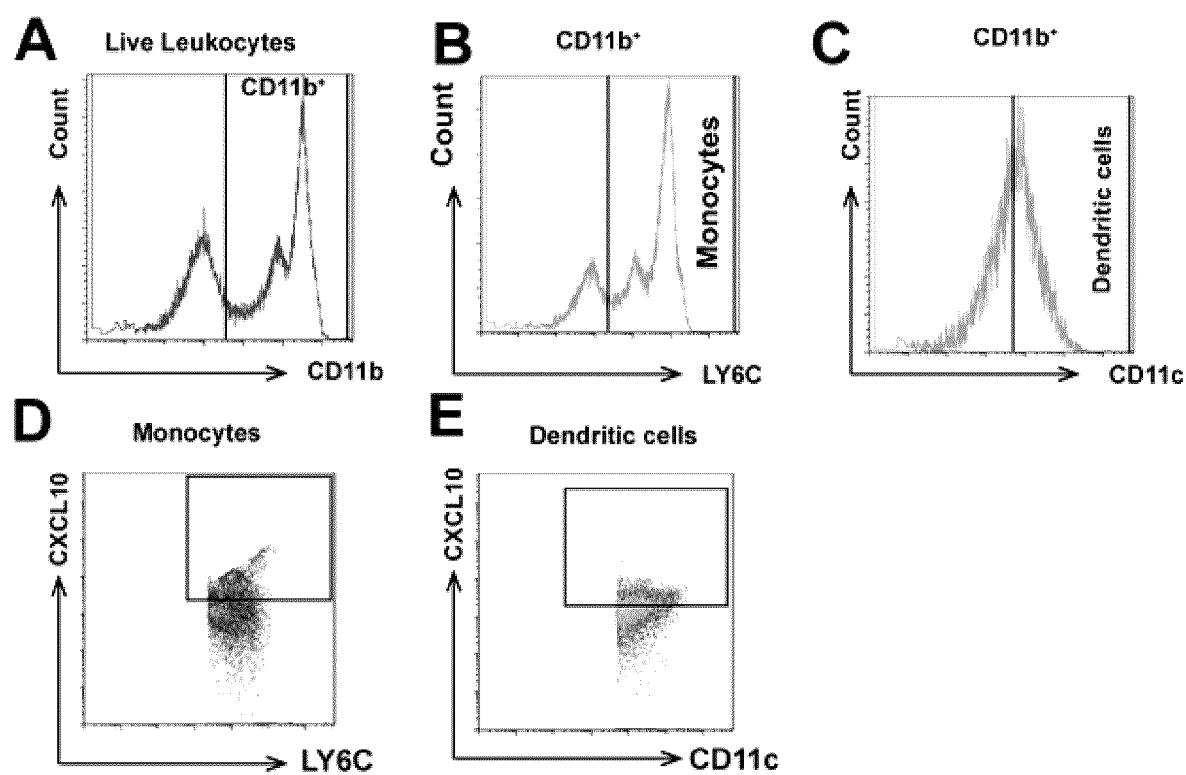
FIG. 7. Flow producing hepatic monocytes and dendritic cells. To detect CXCL10 producing monocytes and dendritic cells gating proceeded as follows: Exclusion of duplet cells followed by gating on forward scatter (FSC) and side scatter (SSC) areas to identify regions appropriate to define all leukocytes, excluding cell debris (as shown in supplementary FIG. 1). Within the leukocyte gate cell population, cells expressing the myeloid lineage marker CD11 b were identified (panel A). Within the CD11b+ subpopulation, monocytes and dendritic cells were identified as CD11b+Ly6C+ and CD11b+CD11c+, respectively (panels B, C). Subsequently, CXCL10 positivity for each cell subpopulation were identified based on the shift above the isotype FMO stained population (panels D and E). cytometry gating strategies for identifying CXCL10
Figure 8:
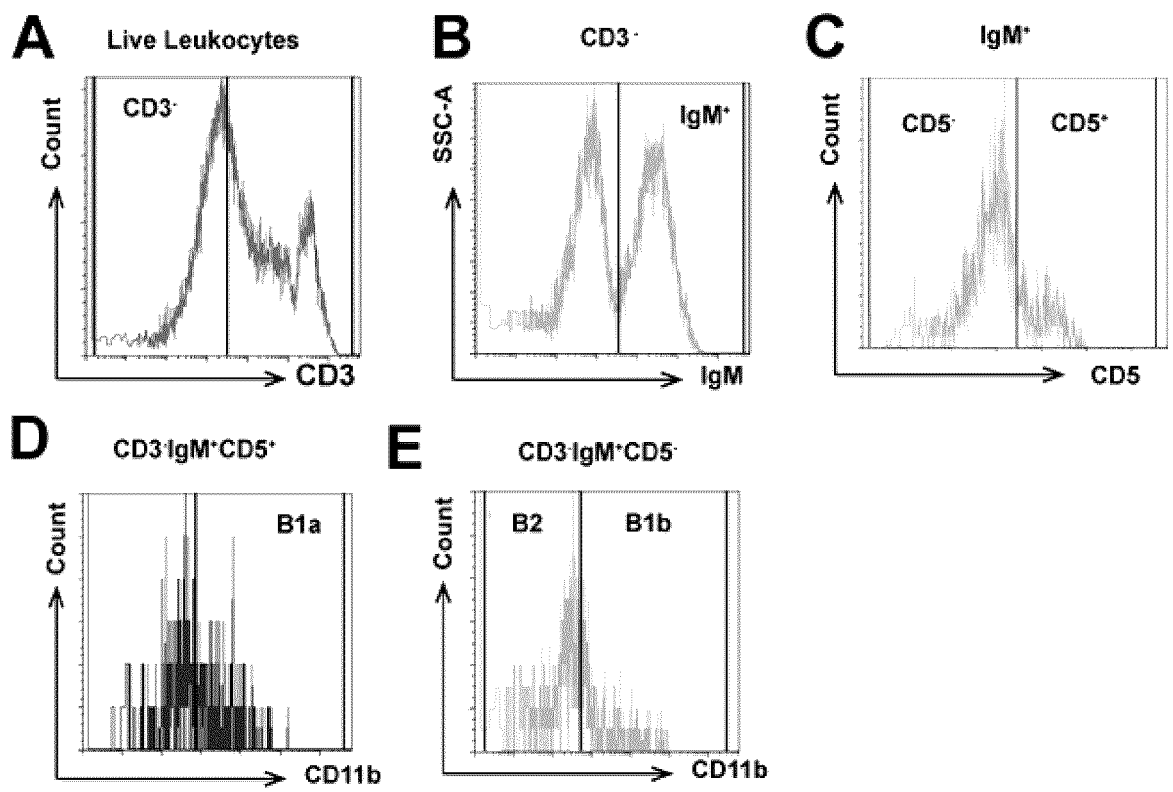
FIG. 8. Gating strategy used to identify hepatic B cell subsets by flow cytometry. To identify hepatic B cell subsets gating proceeded as follows: Exclusion of duplet cells followed by gating on forward scatter (FSC) and side scatter (SSC) areas to identify regions appropriate to define all leukocytes, excluding cell debris (as in supplementary FIG. 1). Within the leukocyte gate cell population, B lymphocytes were identified among total CD3− cells by their expression of immunoglobulin M (IgM) (panels A and B). B cells were further characterized as CD5+ or CD5− subsets (panel C). Within the CD5+ B cell subset, the B1a B cell subset was identified as being IgM+CD5+CD11 b+ (Panel D). B2 and B1b B cell subsets were identified within the CD5− population as being IgM+CD5− CD11b− and IgM+CD5−CD11b+, respectively (Panel E).
Figure 9:
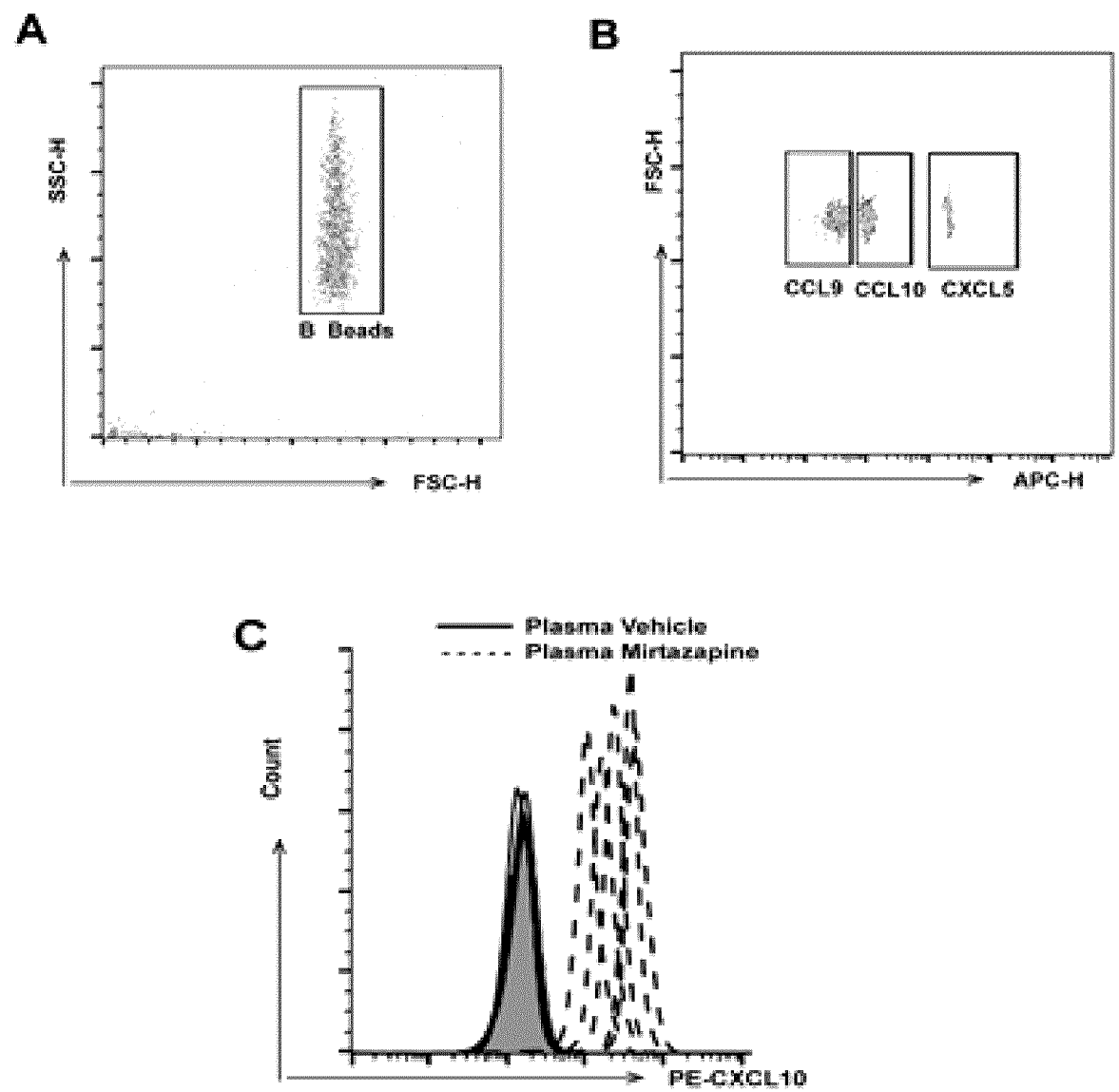
FIG. 9. Plasma and hepatic levels of the chemokines CXCL9 and CXCL10 are higher in mirtazapine-treated mice compared to vehicle treated mice, as assayed by bead-based LEGENDplex® assay. Changes in blood and hepatic levels of CCL9 and CCL10 post-mirtazapine treatment were measured using a flow cytometry bead-based immunoassay (LEGENDplex™ Mouse Chemokine Mix and Match System, BioLegend) according to the manufacturer's instructions, and samples were acquired on Attune™ Acoustic Focusing flow cytometer (Applied Biosytems, Mainway, Burlington, ON). Data were analyzed using LEGENDplex data analysis software (data presented in FIG. 2) or using FlowJo® software (Treestar, Ashland, Oreg.), as presented in this figure. Gating proceeded as follows: Analyte-specific beads were first differentiated by their size and internal fluorescence intensity (Panels A and B). PE fluorescent signal was used to quantify bead positivity for CXCL9 and CXCL10. Panels C, D, E and F are representative histograms depicting CXCL9 and CXCL10 expressing beads after incubation with plasma or liver samples from vehicle (black line) and mirtazapine (dotted line) treated mice. Filled histograms represent PE fluorescent signal of analyte negative beads.
Figure 9:
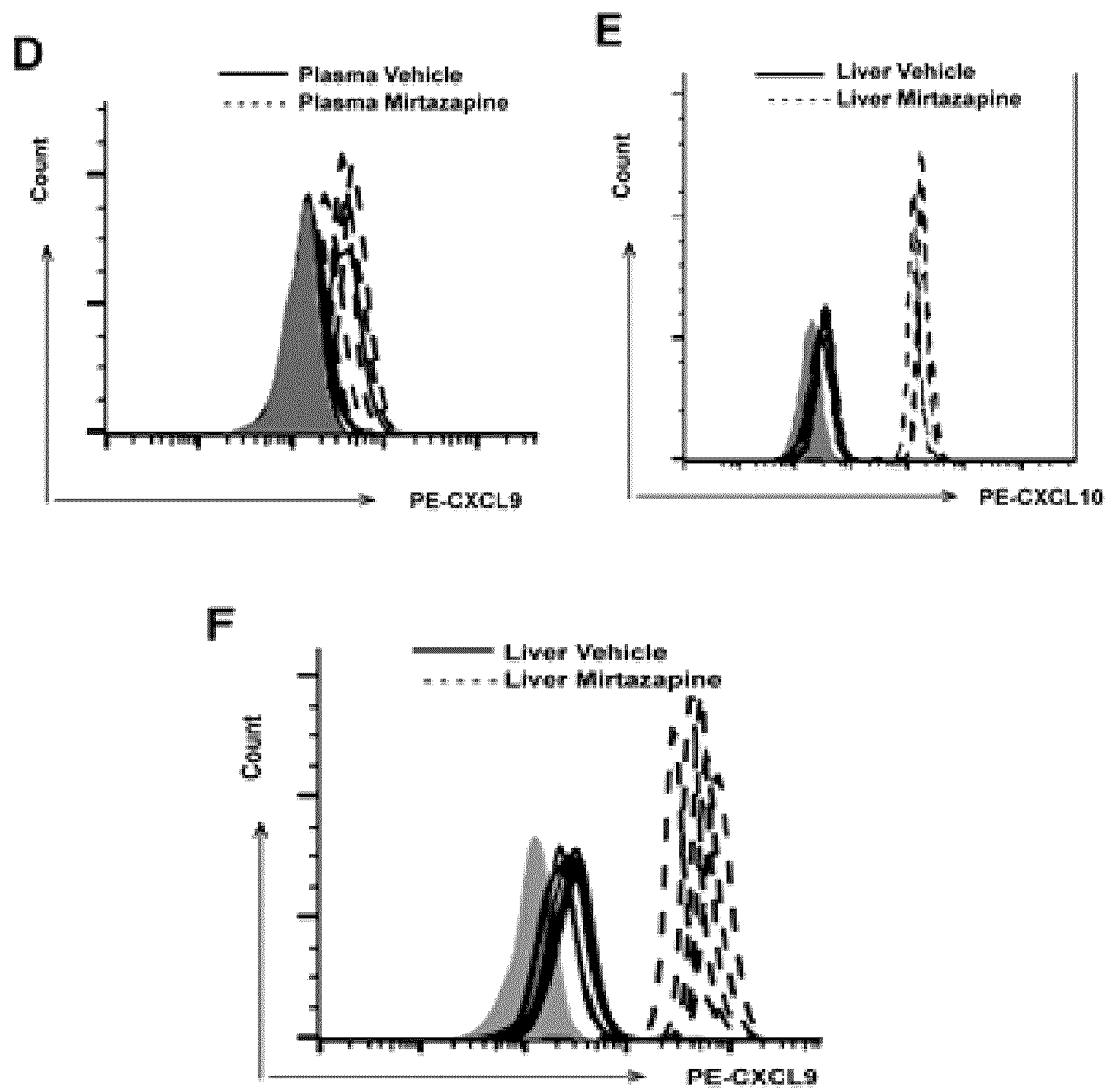

Given our findings of striking mirtazapine-induced alterations in hepatic immune regulatory networks, we next determined the impact of mirtazapine treatment in the Con A model of T cell-mediated liver injury[7]. Con A treatment resulted in marked liver injury as reflected biochemically (serum ALT levels) (FIG. 5A) and histologically at 16 hours post-Con A treatment (FIGS. 5B and C, left panels). Mirtazapine administration markedly attenuated Con A-induced liver damage (FIGS. 5A, B, and C, right panels). Based on dose response experiments (FIG. 5A) we selected the 20 mg/kg dose for further experiments in the Con A model. TNFα and IFNγ critically regulate Con A hepatitis[16, 17]. Mirtazapine treatment significantly reduced hepatic TNFα and IFNγ levels (FIG. 5D) and also significantly reduced hepatic levels of the cytokines IL-6, IL-9, and LIF (FIG. 5D). In contrast, hepatic IL-10 levels were significantly higher in Con A treated mice that received mirtazapine (FIG. 5D). Hepatic levels of the chemokines CXCL9, CXCL2, CXCL1, CCL11, and CCL2 were also reduced in mirtazapine treated Con A treated mice (FIG. 5E). In contrast, mirtazapine treatment significantly augmented hepatic CXCL10 levels after Con A treatment (FIG. 5E). Con A treatment strikingly upregulated expression of VCAM-1 and ICAM-1 within the liver[32]; markedly enhancing endothelial VCAM-1 expression in portal and central veins, as well as on sinusoidal endothelium, but also on sinusoidal immune cells (FIG. 5F, left panel). Con A treatment increased endothelial ICAM-1 expression in central veins and sinusoids, but not in portal veins (FIG. 5G, left panel). Mirtazapine treatment had minimal effect on Con A-induced increases in VCAM-1 expression intensity or patterns within the liver (FIG. 5F, right panel). However, mirtazapine treatment almost completely prevented Con A-induced increases in ICAM-1 expression in hepatic central veins and sinusoidal endothelium (FIG. 5G, right panel).

Discussion

Currently the mainstay of medical treatment for PBC is UDCA[1]. However, 30-40% of PBC patients fail to respond to UDCA treatment[1, 2]. These patients are at risk for disease progression to cirrhosis, liver failure, and transplantation or death[2]. We used a large clinical database to demonstrate, in a cohort of 1177 patients with PBC, that treatment with mirtazapine reduced the risk of liver decompensation, transplantation, or death. Next, we used a mouse model to delineate how mirtazapine may be protective in PBC. Mirtazapine alters hepatic cytokine and chemokine levels, as well as immune cell subtype distribution, leading to a striking attenuation of immune-mediated liver injury. By integrating an epidemiologic population-based study with mechanistic animal model experiments, we provide important data on a novel application of mirtazapine as a treatment for the autoimmune liver disease PBC.

In our patient cohort, the risk of death 10 years following PBC diagnosis was 25%. This high risk of death is consistent with previously published cohorts of PBC patients[1, 2, 33] and was secondary to the high occurrence of decompensated cirrhosis and transplantation. We explored the potential therapeutic effects of anti-depressants on the prognosis of PBC following our observation that PBC patients with depression were less likely to die, as compared to PBC patients without depression. Our analyses demonstrated that the protective effect was specific for mirtazapine. Mirtazapine was responsible for an over four-fold protective effect against liver decompensation, transplantation, or death. The protective association between mirtazapine and liver outcomes in patients with PBC was robust following adjustment for potential confounders including age, sex, and alcohol use. The effect of mirtazapine was independent of the use of UDCA, as the association was consistent following adjustment for the use of UDCA in the Cox proportional hazard model. Moreover, our sensitivity analysis that restricted the study population to patients with PBC taking UDCA showed that mirtazapine's protective effect occurred above and beyond the use of UDCA. Although mirtazapine was originally approved for the clinical treatment of depression, its unique pharmacological profile has facilitated its widespread clinical use to treat numerous other clinical disorders, including sleep disturbance, addiction, and anxiety[34, 35]. Likewise, the majority of patients with PBC in our cohort who were prescribed mirtazapine did not have a coexisting diagnosis of depression. Considering that the majority of PBC patients were not prescribed mirtazapine, the potential therapeutic potential of mirtazapine to prevent the progression of cirrhosis in patients with PBC is likely considerable.

The protective effect of mirtazapine in PBC was supported by the large patient sample size and magnitude of the risk estimate. In contrast, several limitations should be considered. We used a clinical database based on general practitioners' electronic medical records, which raises the potential for misclassification error of the codes used to define the study population and outcomes. Misclassification errors were evaluated with a sensitivity analyses that mandated multiple codes to define PBC[36] and a sensitivity analysis that restricted the population to those with a code for PBC and a prescription for UDCA. Moreover, an epidemiological association cannot prove causality or explain the biological mechanism of mirtazapine's effect in PBC. Therefore, we conducted animal studies to explore possible mechanisms whereby mirtazapine treatment could potentially be linked to improved liver related outcomes in PBC.

Mirtazapine exhibits a complex pharmacology, having both central and peripheral effects[34]. Mirtazapine acts as a 5HT2A/5HT2B receptor antagonist, 5HT2C receptor inverse agonist, and an antagonist for 5HT3 and histamine (H1) receptors[34]. Serotonin and histamine have significant effects in the regulation of immunity. Serotonin regulates numerous aspects of the immune response, from modulating immune cell activation, polarization, and cytokine/chemokine release, to regulating cell death and recruitment[37]. Within the liver, serotonin can enhance fibrosis, hepatocyte proliferation, and liver regeneration, and can suppress inflammation through activation of a variety of receptor subtypes38. In addition, histamine can enhance liver fibrosis[39]. Of specific relevance, hepatic levels of histamine and serotonin are both increased in the livers of PBC patients[40, 41] Therefore, our findings of a beneficial effect of mirtazapine on liver related clinical endpoints in PBC patients may be due, at least in part, to a modulatory effect of mirtazapine on serotonin or histamine-mediated effects on hepatic immunity, with an associated attenuation in liver disease progression.

We found that mirtazapine treatment in mice resulted in significant increases in hepatic levels of a number of cytokines previously implicated in regulating immune-mediated liver disease, including Th1 (e.g. IFNγ, TNFα), Th2 (e.g. IL-4, IL-5, IL-6) and Th17 (e.g. IL-17) subgroups. Consistent with our observations in mice, patients with major depressive disorder treated with mirtazapine have increased circulating TNFα levels[42]. Cytokines critically regulate tissue homeostasis and inflammatory responses[43]. PBC (like many autoimmune diseases) is associated mainly with increased expression of Th1 cytokines, including IFNγ and IL-12, with hepatic expression levels correlating closely with the degree of liver injury in PBC patients[44, 45]. In addition, Th17 expressing T cells are readily identifiable in PBC livers, with their frequency increasing in more advanced disease. Treatment of mice with mirtazapine strikingly altered the hepatic cytokine milieu, with a ~30-fold increase in hepatic IL-4 levels an ~8-fold increase in hepatic IFNγ, and a ~1.5-fold increases in hepatic IL-12 and TNFα levels. IL-4 has profound immunological effects, including inhibition of Th1 and Th17 responses[46], further enhancing Th2 responses[47], facilitating the development of Tregs, upregulation of MHC II expression, and shifting macrophages towards a repair M2-like phenotype48.

Further, we found that mirtazapine treatment resulted in a profound ~120-fold increase in hepatic levels of the IFNγ-inducible chemokine CXCL10 and a ~7-fold increase in CXCL9 levels. In contrast, we found no significant changes in hepatic levels of a number of other chemokines, including CCL2/MCP-1, CCL4/MIP-1β, CCL5/RANTES, CCL11/eotaxin-1, or CCL3/MIP-1a after mirtazapine treatment. Immunohistochemistry demonstrated clearly increased CXCL10 and CXCL9 expression in both hepatocytes and immune cells within the liver after mirtazapine treatment, as well as along sinusoids. In addition, we identified dendritic cells (CD11b+CD11c+) and monocytes (CD11b+LY6C+) as the major hepatic immune cell types producing CXCL10 post-mirtazapine treatment. Increased hepatic levels of CXCL10/CXCL9, as well as numbers of immune cells within the liver expressing CXCR3 (chemokine receptor for CXCL9/CXCL10), have been reported in PBC patients[49], with the highest levels observed in more advanced disease. This association led to the assumption that these two chemokines were pathogenic in PBC. However, more recent findings suggest that CXCL9 (via its receptor CXCR3) is anti-fibrotic in experimental and human liver diseases[50], suggesting that enhanced hepatic expression of CXCR3 ligands may be beneficial in preventing progressive liver disease; a finding with important potential implications for using mirtazapine to treat PBC.

In addition to chemokines, adhesion molecule expression critically regulates immune cell homing to the liver[19, 51-53].

We found that vehicle treated mice showed limited, patchy sinusoidal, portal vein and central vein expression of the adhesion molecule VCAM-1, coupled with weak expression on Kupffer cells located within hepatic sinusoids[20, 32, 51]. However, after mirtazapine treatment there was a striking increase in the intensity of VCAM-1 staining on sinusoidal Kupffer cells, with a less pronounced increase in endothelial VCAM-1 expression. In contrast, in vehicle treated mouse liver we found patchy ICAM-1 expression on both sinusoidal and central vein endothelium, which was unchanged by mirtazapine treatment. Despite this evidence of mirtazapine-induced alterations in hepatic chemokine and adhesion molecule expression, we did not identify mirtazapine-induced changes in total hepatic leukocyte numbers. Therefore, we speculated that given the clinical evidence supporting a beneficial effect of mirtazapine treatment in PBC patients, these mirtazapine-induced changes in hepatic chemokine and adhesion molecule expression patterns might lead to a shift in the composition of hepatic immune cell populations towards phenotypes that could potentially suppress inflammatory responses and enhance tissue repair.

We found that mirtazapine treatment significantly increased the proportion and hepatic numbers of FOXP3+ CD4+ CD25+ Tregs. In addition, mirtazapine treatment enhanced per cell expression intensity of FOXP3 (as MFI); a finding linked by others to enhanced immune regulatory capacity of these cells[54]. B cells are common within normal liver, and their numbers increase dramatically during most liver diseases, including PBC[55, 56]. However, the role of B cells in regulating liver immunity remains poorly understood. B cells possess both effector and regulatory properties, the balance of which can significantly impact immune responses. Murine B cells can be divided into a number of subtypes, including B2 B cells (the most common subtype and important in autoimmunity), B1 B cells (exhibit innate-like properties), and regulatory B cells (suppress inflammatory responses through a variety of mechanisms)[26, 57]. B1 B cells can be subdivided into B1a and B1b B cells, and can express the adenosine-generating ectoenzyme CD73, which is anti-inflammatory within the liver[28, 57, 58]. Moreover, B1 B cells express CXCR3[18]. We now report that mirtazapine treatment significantly alters hepatic B cell composition within the liver, leading to decreased B2 B cells and increased B1a B cells, without altering hepatic B1b B cells. In addition, the proportion of hepatic CXCR3+CD73+B1a B cells were also significantly increased after mirtazapine treatment. Given the well-documented immune regulatory roles of B1 B cells in animal models of autoimmunity[26, 28, 57-59], a mirtazapine-induced enrichment of B1a over B2 B cells within the liver (especially those expressing CD73) could contribute to a shift in the hepatic immunological milieu towards a more immunosuppressive phenotype that, in turn, could suppress tissue injury and prevent PBC disease progression. Interestingly, B cell depletion therapy in PBC has limited impact on disease severity, which is an observation consistent with possible therapy-induced B cell depletion of both pro- and anti-inflammatory hepatic B cell populations in these patients[60].

Monocytes exhibit diverse roles in the regulation of inflammatory responses[25, 30, 43, 53]. In mice, monocytes are classically divided into 2 main populations: LY6Chi pro-inflammatory monocytes (circulate in blood, recruited into tissues during inflammatory responses) and LY6Clo monocytes (important in tissue repair)[25, 30]. Although LY6Clo monocytes patrol the extrahepatic vasculature, recent evidence suggests that within the liver LY6Chi, and not LY6Clo, monocytes patrol hepatic sinusoids[25]. We found that mirtazapine treatment strikingly altered the balance of LY6Chi vs. LY6Clo monocytes within the liver. Specifically, mirtazapine treatment profoundly reduced hepatic numbers of LY6Chi monocytes, whereas mirtazapine induced a less dramatic reduction in numbers of LY6Clo monocytes within the liver. This shift in hepatic monocyte populations induced by mirtazapine treatment, similar to shifts in hepatic T and B cells populations outlined above, would likely contribute to the generation of a more anti-inflammatory/pro-repair hepatic environment, which could in turn be of potential clinical benefit if similar changes occur within the liver of mirtazapine treated PBC patients.

Our findings of a striking effect of mirtazapine-treatment upon multiple pathways linked to the regulation of hepatic immunity in normal liver led us to investigate the potential impact of mirtazapine treatment on the susceptibility of mice to T cell-driven immune-mediated liver damage induced by Con A. Con A treatment is a widely used murine model of immune-mediated liver injury that is driven mainly by CD4 T cells and the Th1 cytokines IFNγ and TNFα[16, 17]; mediators also implicated in the pathogenesis of PBC[1, 44, 45, 61]. Previous work has also shown that CXCR3 expression critically suppresses the development of Con A hepatitis, in part by promoting regulatory T cell recruitment to the liver16. We found that mirtazapine treatment strikingly attenuated Con A-mediated liver injury. Moreover, the beneficial effect of mirtazapine was associated with reductions in Con A-induced elevations in hepatic levels of numerous pro-inflammatory cytokines and chemokines. As outlined above, immune cell recruitment to inflamed tissues is regulated by both hepatic chemokine and adhesion molecule expression[43, 51-53]. In Con A hepatitis, hepatic expression of the adhesion molecules ICAM-1 and VCAM-1 are markedly increased and are critical for hepatic CD4 T cell recruitment and subsequent development of liver damage[62, 63]. Similarly, ICAM-1 and VCAM-1 expression are upregulated in the livers of PBC patients[51, 64] and lymphocytes recruited into the liver in PBC patients express corresponding ligands to these adhesion molecules: namely, LFA-1 and VLA-4, respectively[65]. We have confirmed previous observations that Con A strikingly increases hepatic expression of both ICAM-1 and VCAM-1[32]. However, we now show that mirtazapine treatment markedly attenuates Con A-induced increases in hepatic expression of ICAM-1, but not VCAM-1 expression, within the liver. Inhibition of immune-driven upregulation of important lymphocyte relevant adhesion molecules within the liver could potentially contribute significantly to mirtazapine related hepatoprotective effects in PBC patients.

In summary, we discovered that mirtazapine improves mortality, reduces the need for liver transplantation, and inhibits the development of decompensated cirrhosis in PBC patients. The protective effect of mirtazapine was independent of the role of depression, prescription of other antidepressants, and the use of UDCA. Furthermore, we have defined a possible mechanism whereby mirtazapine could be hepatoprotective by showing that mirtazapine alters the hepatic cytokine/chemokine milieu and shifts immune cell populations within the liver towards more regulatory phenotypes. These mirtazapine related alterations in hepatic immunity in turn led to a profound anti-inflammatory effect in a mouse model of T cell-mediated hepatitis. The novel anti-inflammatory effect of mirtazapine has tremendous clinical potential, as effective treatment for halting the progression of liver disease in many patients with PBC remains an unmet medical need. Moreover, if these immune-modulatory effects of mirtazapine are more generalizable, the beneficial effects of mirtazapine may also be applicable in other autoimmune liver diseases, including autoimmune hepatitis and primary sclerosing cholangitis.

Example 2

(A) Mirtazapine-Induced Enhancement of Regulatory Immune Cell Recruitment into Tissues as Beneficial for Treating Inflammatory and Autoimmune Disease.

The balance of pro- and anti-inflammatory processes are tightly regulated within the immune system. Moreover, immune system-mediated inflammatory responses are critically important for the control and resolution of pathogenic challenges to the host. However, immune responses must be transient in dealing with acute insults (e.g. infections) as prolonged activation of the immune system, in the context of inflammatory responses, can lead to tissue damage and may contribute to autoimmunity (Buckley C D et al. Nature Rev Immunol 2013; Tabas I and Glass C K. Science 2013). Immune cell populations contain inhibitory populations that are critical for restraining pro-inflammatory immune responses, and play key roles in the resolution of inflammation and tissue repair. These populations include (i) regulatory T cells (Tregs), (ii) regulatory B cells and (iii) regulatory myeloid cells (repair/M2/LY6C$^{lo}$ macrophages).

(i) Tregs: Regulatory T cells play a key role in the regulation and suppression of immune-mediated inflammation and disease. They accomplish this through the release of soluble anti-inflammatory factors including cytokines (e.g. IL-10, TGFbeta) and other soluble mediators (e.g. adenosine), through local consumption of IL-2, and via the high expression of surface molecules including CTLA-4 which suppress antigen presenting cells (APCs). Tregs have been shown to be critically important in suppressing inflammation and tissue injury in numerous diseases, including the autoimmune diseases Type 1 diabetes [T1DM], inflammatory bowel disease [IBD], rheumatoid arthritis [RA], psoriasis, and multiple sclerosis, and have also been shown to beneficially suppress inflammation and tissue damage in solid organ transplantation, graft vs host disease and allergic responses (reviewed in Plitas G and Rudensky A Y. Cancer Immunol Res 2016). As a result of this a number of strategies are currently being developed to therapeutically enhance Treg numbers and/or function in tissues of patients with inflammatory, allergic or autoimmune diseases, and in the context of transplantation.

Therefore, our finding suggest that mirtazapine administration increases Treg numbers within the liver have therapeutic implications for increasing Treg numbers in the setting of chronic inflammatory, allergic and autoimmune diseases, and for patients post-transplantation.

(ii) Regulatory B cells: B1a B cells have both pro- and anti-inflammatory properties. They are long-liver, non-circulating and self-renewing immune cells that reside mainly in the peritoneal and pleural cavities (minor population in the spleen). B1a B cells produce most circulating IgM (natural antibodies) and have enhanced antigen presenting capacities. However, B1a B cells are also major producers of the anti-inflammatory cytokine IL-10 (O'Garra A et al. Eur J Immunol 1992), and facilitate the production of the anti-inflammatory molecule adenosine, and have therefore been implicated in the suppression of inflammatory responses and autoimmunity. Specifically, increases in B1a B cells have been shown to decrease anti-ds DNA antibody production and decrease the incidence of lupus nephritis in a mouse model (Wen X S et al. Eur J Immunol 2004). Moreover, B1a B cells can induce Tregs via an IL-10 independent mechanism (Hsu L-H et al. Cellular Mol Immunol 2015). In a mouse model of multiple sclerosis (EAE) B cell depletion decreases regulatory B cell properties, and increases proinflammatory antigen presenting cell capacity exacerbating disease (Lehmann-Horn K et al. J Neuroinflamm 2011). These findings are consistent with an important role for regulatory B cell populations in suppressing these autoimmune disorders, and would in turn suggest that augmentation of regulatory B cell populations may be of clinical benefit as a therapeutic strategy in these autoimmune diseases.

Roughly 50% of B1a B cells express the ectoenzyme CD73 on their cell surface (whereas B2 cells do not), and CD73 plays a critical role in the local tissue generation of the anti-inflammatory molecule adenosine (Kaku H et al. J Immunol 2014). Adoptive transfer of CD73+B cells in mice ameliorates DSS-induced colitis (a widely used pre-clinical model of IBD) via adenosine production (Kaku H et al. J Immunol 2014). In addition, genetic defects in the adenosine producing pathway increases the susceptibility of patients to Crohn's disease (Friedman D J et al. PNAS 2009), and B cell depletion increases disease severity in patients with ulcerative colitis (Goetz M et al. Inflam Bowel Dis 2007) and in patients with psoriasis (Dass S et al. Arth Rheum 2007). These data are consistent with an important role of B cells with regulatory properties, and for B cell driven adenosine production, in the clinical expression of IBD.

Regulatory B cells, and CD73, have gained increasing recognition as being important in transplantation (especially in the context of chronic rejection). This has in turn led to a growing interest in developing therapeutic strategies that could enhance tissue numbers of regulatory B cells, or adenosine production, as a way to treat chronic rejection in the setting of transplantation (Nouel A et al. Frontier Immunol 2014; Roberts V et al. Frontiers Immunol 2014).

Adenosine also plays a role in the development of lung fibrosis in preclinical models, and in turn therefore has been linked to the clinical manifestation in patients called idiopathic interstitial pneumonias (IIPs) which include: interstitial pulmonary fibrosis (IPF), NSPI (non-specific interstitial pneumonia), COP (cryptogenic organizing pneumonia), DIP (desquamitive interstitial pneumonia), RB-ILD (respiratory bronchiolitis-associated interstitial lung disease), and LIP (lymphocytic interstitial pneumonia). These conditions remain without effective therapy and therefore constitute areas of significant unmet medical need (Della Latta V et al. Pharmacol Res 2013).

Therefore, these data indicate that in a number of important medical diseases and conditions in which medial therapy is lacking (or is suboptimal), enhanced regulatory B cell numbers and/or enhanced adenosine production are potential desirable therapeutic goals. We have shown that mirtazapine can enhance B1a regulatory B cell infiltration into tissues, and that these B1a B cells express the adenosine producing enzyme CD73. In addition, mirtazapine treatment also increases hepatic numbers of CD73 expressing T cells, which are also known to suppress inflammation in tissues via adenosine production.

Figure 11:
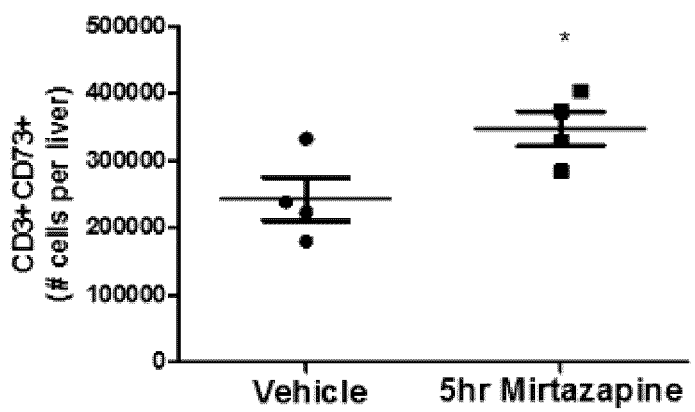
FIG. 11 (A) depicts CD3+CD73+(# cells per liver) for vehicle and 5 hr mirtazapine, (B) depicts CD3+CD73+(%) vehicle and 5 hr mirtazapine.
Figure 11:
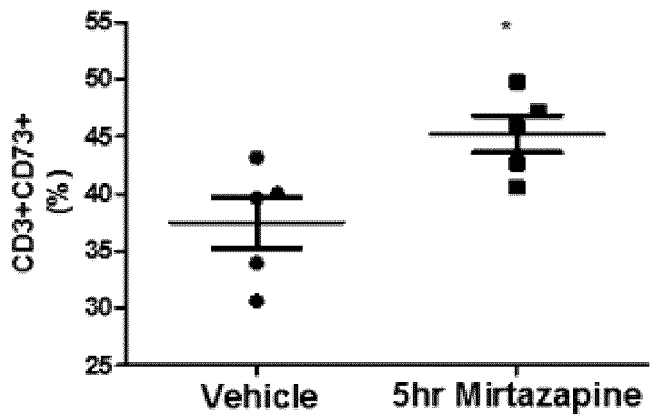

FIG. 11 (A) depicts CD3+CD73+ (# cells per liver) for vehicle and 5 hr mirtazapine, (B) depicts CD3+CD73+ (%) vehicle and 5 hr mirtazapine.

(iii) Regulatory myeloid cells: The tissue balance of pro-inflammatory (M1) and anti-inflammatory/repair (M2) macrophages contributes significantly to the regulation of tissue injury and repair. CCR2+ LY6Chi monocytes are recruited to inflamed tissues where they produce numerous inflammatory mediators and cytokines, and can turn in to classically activated (M1) macrophages (Palframan R et al. J Exp Med 2001; Geissman F et al. Immunity 2003; Sunderkotter C et al. J Immunol 2004; Varga T et al. J Immunol; Hilgendorf I et al Circ Res 2014). In contrast, $LY6C^{lo}$ monocytes patrol the endothelium and are recruited into tissues where they suppress inflammation and are reparative, and may become alternatively activated macrophages (M2) (Arnolod L et al. J Exp Med 2007; Auffray C et al. Science 2007).

We found that mirtazapine decreased hepatic numbers of LY6Chi and enhanced the relative numbers of LY6Clo monocytes. Therefore, mirtazapine treatment may represent a novel strategy to enhance tissue numbers of anti-inflammatory and reparative monocytes/macrophages, that could in turn be beneficial for treating chronic inflammatory and autoimmune disorders. Also, given that $LY6C^{lo}$ monocytes patrol the endothelium of the vasculature, and have been termed "the housekeepers of the vasculature", enhancing LY6Clo numbers may also be beneficial for atherosclerosis and myocardial infarction Carlin L M et al. Cell 2013; Nahrendorf M et al. J Exp Med 2007; Hanna R N et al. Circ Res 2012).

Summary of Part A

Increasing regulatory immune cell recruitment into inflamed or diseased tissues is a desired goal for therapeutically attenuating tissue damage. We have identified a novel effect of the atypical anti-depressant mirtazapine in increasing the recruitment of regulatory T cells, regulatory B cells and repair monocytes into the liver. Enhanced hepatic recruitment of these regulatory immune cells was in turn associated with decreased immune-mediated liver injury. Therefore, if mirtazapine also enhances regulatory immune ecell recruitment into other tissues, use of this well characterized and widely used medication could represent a novel and safe therapeutic approach to diseases characterized by chronic inflammation and/or autoimmunity, as well as in the setting of transplantation.

(B) Mirtazapine-Induced Enhancement of Tissue Expression of the Chemokines CXCL9 and CXCL10 as being Potentially Beneficial for Treating Disease.

The chemokines CXCL9 and CXCL10 can regulate tissue inflammation and damage through regulating the balance of CXCR3 expressing effector T cell recruitment (e.g. Th1), and CXCR3 expressing regulatory T and B cell recruitment into tissues. The effects of these two chemokines on immune cell recruitment are mediated through actions on their cognate receptor CXCR3. CXCR3 is expressed on T lymphocytes, Tregs, regulatory B cells, dendritic cells (DCs) and NK cells.

However, CXCR3 is also expressed on non-immune cells within tissues, including fibroblasts, smooth muscle cells, epithelial cells and endothelial cells (van Raemdonck K et al. Cytokine Growth Factor Rev 2015). Therefore, CXCL9 and CXCL10 can also exhibit effects in tissues that are independent of immune cell recruitment. In preclinical models using mice with genetic deletion of CXCR3 (ie. CXCR3 KO), these CXCR3 KO mice have been shown to develop enhanced lung fibrosis and mortality in a model of pulmonary fibrosis (ie IPF), and mice develop enhanced liver fibrosis induced by carbon tetrachloride (Liu L et al. Cuurrent Topics in Devel Biol 2005; Jian D et al. J Clin Invest 2004)—findings that were independent of changes in immune cell recruitment into these tissues. These observations implicate CXCR3 driven activation in biological benefit in these disease models, an effect likely driven through enhanced effects induced by the biological ligands for this receptor; namely, CXCL9 and CXCL10.

We have found that mirtazapine treatment robustly increases hepatic levels of both CXCL9 and CXCL10 in mice, and that increased hepatic expression of these two chemokines was in turn associated with attenuated immune-mediated hepatic injury. These findings are in keeping with a number of pre-clinical and clinical observations that suggest a potential beneficial role for CXCL9 and/or CXCL10 in the regulation of tissue damage and fibrosis in a number of diseases, as outlined below:

(i) Multiple Sclerosis (MS):

CXCL9 and CXCL10 expression in tissues is driven by a number of cytokines, however IFNγ plays a key role in this process. In a mouse model of MS (ie EAE) brain levels of both CXCL9 and CXCL01 are robustly increased. However, IFNγ KO mice do not demonstrate increased brain levels of these chemokines and in turn demonstrate markedly worse disease severity. This finding was subsequently linked to a critical role of these chemokines in recruiting Tregs into the brain via CXCR3 (Muller M et al. J Immunol 2007). Similarly, observations in beta interferon treated MS patients are consistent with a protective role of CXCL10 and CXCR3 in MS patients (Cepok S et al. Arch Neurol 2009). In addition, genetic studies have suggested that gene alterations that are linked to decreased CXCL10 production in patients, enhances disease progression in MS (Galimbert D et al. Eur J Neurol 2007).

(ii) Heart:

Decreased numbers of Tregs have been identified in patients with cardiac inflammation. Moreover, CXCL10 levels in the blood are increased in patients with coronary artery disease and acute MI, and serum CXCL10 levels negatively correlate with infarct size in acute MI patients (reviewed in Altara R et al. J Immunol Res 2016).

(iii) Liver Fibrosis:

CXCL9 has been shown to have anti-fibrotic effects in the liver, and can decrease collagen production in human hepatic stellate cells (Wasmuth H et al. Gastroenterology 2009; Liang Y-J et al. PLOSone 2012). In addition, a genetic mutation in humans that is associated with decreased CXCL9 production is associated with increased liver fibrosis in chronic liver disease patients (Wasmuth H et al. Gastro 2009).

(iv) Hepatocellular Cancer (HCC):

CXCL10 is angiostatic, and HCC is a highly vascular tumor. Moreover, CXCL10 can inhibit hepatocyte proliferation (Yoneyama H et al. Med Mol Morphol 2007). These effects could be therapeutically beneficial in patients with HCC—a disease with significant unmet medical need.

(v) Kidney Fibrosis (Chronic Kidney Disease):

Chronic liver disease, characterized by increasing renal fibrosis, is a significant health care burden and is without effective therapy. In preclinical research, CXCR3 KO mice, and mice in which CXCL10 has been neutralized using an antibody, exhibited enhanced renal fibrosis after unilateral ureteral obstruction (a widely used model of kidney fibrosis) (Nakaya I et al. Nephron Exp Nephrol 2007). These observations suggest that increased CXCL10 levels may beneficial in attenuating renal fibrosis. We have found that mirtazapine increases plasma levels of CXCL10, and increases tissue (ie liver) CXCL10 levels.

(vi) Pulmonary Fibrosis (IPF):

As outlined above, Jiang et al (Jiang D et al. J Clin Invest 2004) showed that CXCR3 KO mice have attenuated fibrosis and mortality in a model of IPF. Consistent with this observation, in a study by Tager et al mice with a CXCL10 gene deletion (ie. CXCL10 KO) exhibit decreased fibroblast accumulation in the lung and decreased fibrosis in a model of IPF (Tager A M et al. Am J Resp Cell Mol Biol 2004). Moreover, increasing lung CXCL10 levels decreased mortality in this model of IPF (Tager et al).

Summary of Part B

As outlined in part A above, mirtazapine can enhance the recruitment of regulatory immune cells into the liver. These recruited regulatory immune cells are enriched in CXCR3 expression—the cognate receptor for the chemokines CXCL9 and CXCL10. However, a number of preclinical and clinical observations suggest that CXCL9 and/or CXCL10 can also have both anti-inflammatory and anti-fibrotic effects, including in the lung, kidney and liver. Given that fibrosis is a hallmark of many chronic kidney, lung and liver diseases, and that there are no effective treatments for fibrosis, a mirtazapine-induced increase in tissue CXCL9 and/or CXCL10 levels may have significant clinical benefit.

REFERENCES

1. Hohenester S, Oude-Elferink R P, Beuers U. Primary biliary cirrhosis. Semin Immunopathol 2009; 31:283-307.
2. Pares A, Caballeria L, Rodes J. Excellent long-term survival in patients with primary biliary cirrhosis and biochemical response to ursodeoxycholic Acid. Gastroenterology 2006; 130:715-20.
3. Mells G F, Pells G, Newton J L, et al. Impact of primary biliary cirrhosis on perceived quality of life: the UK-PBC national study. Hepatology 2013; 58:273-83.
4. Al-Harthy N, Kumagi T, Coltescu C, et al. The specificity of fatigue in primary biliary cirrhosis: evaluation of a large clinic practice. Hepatology 2010; 52:562-70.
5. Eyre H A, Lavretsky H, Kartika J, et al. Modulatory Effects of Antidepressant Classes on the Innate and Adaptive Immune System in Depression. Pharmacopsychiatry 2016; 49:85-96.
6. O'Connell P J, Wang X, Leon-Ponte M, et al. A novel form of immune signaling revealed by transmission of the inflammatory mediator serotonin between dendritic cells and T cells. Blood 2006; 107:1010-7.
7. Frick L R, Rapanelli M. Antidepressants: influence on cancer and immunity? Life Sci 2013; 92:525-32.
8. THIN Data Guide for Researchers version 2. pp 106-108, 2010.
9. Bhayat F, Das-Gupta E, Smith C, et al. The incidence of and mortality from leukaemias in the UK: a general population-based study. BMC Cancer 2009; 9:252.
10. Wallace H, Shorvon S, Tallis R. Age-specific incidence and prevalence rates of treated epilepsy in an unselected population of 2,052,922 and age-specific fertility rates of women with epilepsy. Lancet 1998; 352:1970-3.
11. Lawrance I C, Wu F, Leite A Z, et al. A murine model of chronic inflammation-induced intestinal fibrosis downregulated by antisense NF-kappa B. Gastroenterology 2003; 125:1750-61.
12. Kronman M P, Zaoutis T E, Haynes K, et al. Antibiotic exposure and IBD development among children: a population-based cohort study. Pediatrics 2012; 130:e794-803.
13. Fang C K, Chen H W, Chiang I T, et al. Mirtazapine inhibits tumor growth via immune response and serotonergic system. PLoS One 2012; 7:e38886.
14. Bittolo T, Raminelli C A, Deiana C, et al. Pharmacological treatment with mirtazapine rescues cortical atrophy and respiratory deficits in MeCP2 null mice. Sci Rep 2016; 6:19796.
15. Nakayama K, Sakurai T, Katsu H. Mirtazapine increases dopamine release in prefrontal cortex by 5-HT1A receptor activation. Brain Res Bull 2004; 63:237-41.

16. Erhardt A, Wegscheid C, Claass B, et al. CXCR3 deficiency exacerbates liver disease and abrogates tolerance in a mouse model of immune-mediated hepatitis. J Immunol 2011; 186:5284-93.
17. Ajuebor M N, Aspinall A I, Zhou F, et al. Lack of chemokine receptor CCR5 promotes murine fulminant liver failure by preventing the apoptosis of activated CD1d-restricted NKT cells. J Immunol 2005; 174:8027-37.
18. Almishri W, Deans J, Swain M G. Rapid activation and hepatic recruitment of innate-like regulatory B cells after invariant NKT cell stimulation in mice. J Hepatol 2015; 63:943-51.
19. Lalor P F, Shields P, Grant A, et al. Recruitment of lymphocytes to the human liver. Immunol Cell Biol 2002; 80:52-64.
20. Okada T, Kimura A, Kanki K, et al. Liver Resident Macrophages (Kupffer Cells) Share Several Functional Antigens in Common with Endothelial Cells. Scand J Immunol 2016; 83:139-50.
21. Mehal W Z, Juedes A E, Crispe I N. Selective retention of activated CD8+ T cells by the normal liver. J Immunol 1999; 163:3202-10.
22. Oo Y H, Sakaguchi S. Regulatory T-cell directed therapies in liver diseases. J Hepatol 2013; 59:1127-34.
23. Benezech C, Luu N T, Walker J A, et al. Inflammation-induced formation of fat-associated lymphoid clusters. Nat Immunol 2015; 16:819-28.
24. Samuelson E M, Laird R M, Maue A C, et al. Blk haploinsufficiency impairs the development, but enhances the functional responses, of MZ B cells. Immunol Cell Biol 2012; 90:620-9.
25. Dal-Secco D, Wang J, Zeng Z, et al. A dynamic spectrum of monocytes arising from the in situ reprogramming of CCR2+ monocytes at a site of sterile injury. J Exp Med 2015; 212:447-56.
26. Yanaba K, Bouaziz J D, Matsushita T, et al. B-lymphocyte contributions to human autoimmune disease. Immunol Rev 2008; 223:284-99.
27. O'Garra A, Chang R, Go N, et al. Ly-1 B (B-1) cells are the main source of B cell-derived interleukin 10. Eur J Immunol 1992; 22:711-7.
28. Kaku H, Cheng K F, Al-Abed Y, et al. A novel mechanism of B cell-mediated immune suppression through CD73 expression and adenosine production. J Immunol 2014; 193:5904-13.
29. Saze Z, Schuler P J, Hong C S, et al. Adenosine production by human B cells and B cell-mediated suppression of activated T cells. Blood 2013; 122:9-18.
30. Geissmann F, Jung S, Littman D R. Blood monocytes consist of two principal subsets with distinct migratory properties. Immunity 2003; 19:71-82.
31. Auffray C, Fogg D, Garfa M, et al. Monitoring of blood vessels and tissues by a population of monocytes with patrolling behavior. Science 2007; 317:666-70.
32. Wolf D, Hallmann R, Sass G, et al. TNF-alpha-induced expression of adhesion molecules in the liver is under the control of TNFR1—relevance for concanavalin A-induced hepatitis. J Immunol 2001; 166:1300-7.
33. Lammers W J, van Buuren H R, Hirschfield G M, et al. Levels of alkaline phosphatase and bilirubin are surrogate end points of outcomes of patients with primary biliary cirrhosis: an international follow-up study. Gastroenterology 2014; 147:1338-49 e5; quiz e15.
34. Croom K F, Perry C M, Plosker G L. Mirtazapine: a review of its use in major depression and other psychiatric disorders. CNS Drugs 2009; 23:427-52.
35. Alam A, Voronovich Z, Carley J A. A review of therapeutic uses of mirtazapine in psychiatric and medical conditions. Prim Care Companion CNS Disord 2013; 15.
36. Myers R P, Shaheen A A, Fong A, et al. Epidemiology and natural history of primary biliary cirrhosis in a Canadian health region: a population-based study. Hepatology 2009; 50:1884-92.
37. Mossner R, Lesch K P. Role of serotonin in the immune system and in neuroimmune interactions. Brain Behav Immun 1998; 12:249-71.
38. Ruddell R G, Mann D A, Ramm G A. The function of serotonin within the liver. J Hepatol 2008; 48:666-75.
39. Jones H, Hargrove L, Kennedy L, et al. Inhibition of mast cell-secreted histamine decreases biliary proliferation and fibrosis in primary sclerosing cholangitis Mdr2 (−/−) mice. Hepatology 2016; 64:1202-16.
40. Gittlen S D, Schulman E S, Maddrey W C. Raised histamine concentrations in chronic cholestatic liver disease. Gut 1990; 31:96-9.
41. Lalor P F, Herbert J, Bicknell R, et al. Hepatic sinusoidal endothelium avidly binds platelets in an integrin-dependent manner, leading to platelet and endothelial activation and leukocyte recruitment. Am J Physiol Gastrointest Liver Physiol 2013; 304:G469-78.
42. Kraus T, Haack M, Schuld A, et al. Body weight, the tumor necrosis factor system, and leptin production during treatment with mirtazapine or venlafaxine. Pharmacopsychiatry 2002; 35:220-5.
43. Heymann F, Tacke F. Immunology in the liver—from homeostasis to disease. Nat Rev Gastroenterol Hepatol 2016; 13:88-110.
44. Harada K, Van de Water J, Leung P S, et al. In situ nucleic acid hybridization of cytokines in primary biliary cirrhosis: predominance of the Th1 subset. Hepatology 1997; 25:791-6.
45. Yang C Y, Ma X, Tsuneyama K, et al. IL-12/Th1 and IL-23/Th17 biliary microenvironment in primary biliary cirrhosis: implications for therapy. Hepatology 2014; 59:1944-53.
46. Harrington L E, Hatton R D, Mangan P R, et al. Interleukin 17-producing CD4+ effector T cells develop via a lineage distinct from the T helper type 1 and 2 lineages. Nat Immunol 2005; 6:1123-32.
47. Tato C M, Laurence A, O'Shea J J. Helper T cell differentiation enters a new era: le roi est mort; vive le roi! J Exp Med 2006; 203:809-12.
48. Njoku D B. Suppressive and pro-inflammatory roles for IL-4 in the pathogenesis of experimental drug-induced liver injury: a review. Expert Opin Drug Metab Toxicol 2010; 6:519-31.
49. Chuang Y H, Lian Z X, Cheng C M, et al. Increased levels of chemokine receptor CXCR3 and chemokines IP-10 and MIG in patients with primary biliary cirrhosis and their first degree relatives. J Autoimmun 2005; 25:126-32.
50. Wasmuth H E, Lammert F, Zaldivar M M, et al. Antifibrotic effects of CXCL9 and its receptor CXCR3 in livers of mice and humans. Gastroenterology 2009; 137:309-19, 319 e1-3.
51. Borchers A T, Shimoda S, Bowlus C, et al. Lymphocyte recruitment and homing to the liver in primary biliary cirrhosis and primary sclerosing cholangitis. Semin Immunopathol 2009; 31:309-22.
52. Crispe I N. Migration of lymphocytes into hepatic sinusoids. J Hepatol 2012; 57:218-20.
53. Jenne C N, Kubes P. Immune surveillance by the liver. Nat Immunol 2013; 14:996-1006.

54. Chauhan S K, Saban D R, Lee H K, et al. Levels of Foxp3 in regulatory T cells reflect their functional status in transplantation. J Immunol 2009; 182:148-53.
55. Jin Q, Moritoki Y, Lleo A, et al. Comparative analysis of portal cell infiltrates in antimitochondrial autoantibody-positive versus antimitochondrial autoantibody-negative primary biliary cirrhosis. Hepatology 2012; 55:1495-506.
56. Shetty S, Bruns T, Weston C J, et al. Recruitment mechanisms of primary and malignant B cells to the human liver. Hepatology 2012; 56:1521-31.
57. Rosser E C, Mauri C. Regulatory B cells: origin, phenotype, and function. Immunity 2015; 42:607-12.
58. Wang H, Lin J X, Li P, et al. New insights into heterogeneity of peritoneal B-1a cells. Ann N Y Acad Sci 2015; 1362:68-76.
59. Hsu L H, Li K P, Chu K H, et al. A B-1a cell subset induces Foxp3(−) T cells with regulatory activity through an IL-10-independent pathway. Cell Mol Immunol 2015; 12:354-65.
60. Myers R P, Swain M G, Lee S S, et al. B-cell depletion with rituximab in patients with primary biliary cirrhosis refractory to ursodeoxycholic acid. Am J Gastroenterol 2013; 108:933-41.
61. Kouroumalis E, Notas G. Primary biliary cirrhosis: From bench to bedside. World J Gastrointest Pharmacol Ther 2015; 6:32-58.
62. Kawasuji A, Hasegawa M, Horikawa M, et al. L-selectin and intercellular adhesion molecule-1 regulate the development of Concanavalin A-induced liver injury. J Leukoc Biol 2006; 79:696-705.
63. Morikawa H, Hachiya K, Mizuhara H, et al. Sublobular veins as the main site of lymphocyte adhesion/transmigration and adhesion molecule expression in the porto-sinusoidal-hepatic venous system during concanavalin A-induced hepatitis in mice. Hepatology 2000; 31:83-94.
64. Adams D H, Hubscher S G, Shaw J, et al. Increased expression of intercellular adhesion molecule 1 on bile ducts in primary biliary cirrhosis and primary sclerosing cholangitis. Hepatology 1991; 14:426-31.
65. Yasoshima M, Nakanuma Y, Tsuneyama K, et al. Immunohistochemical analysis of adhesion molecules in the micro-environment of portal tracts in relation to aberrant expression of PDC-E2 and HLA-DR on the bile ducts in primary biliary cirrhosis. J Pathol 1995; 175:319-25.
66. Santodomingo-Garzon T, Han J, Le T, Yang Y, Swain M G. Natural killer T cells regulate the homing of chemokine CXC receptor 3-positive regulatory T cells to the liver in mice. Hepatology 2009; 49:1267-1276.
67. D'Mello C, Le T, Swain M G. Cerebral microglia recruit monocytes into the brain in response to tumor necrosis factoralpha signaling during peripheral organ inflammation. The Journal of neuroscience: the official journal of the Society for Neuroscience 2009; 29:2089-2102.

Example 3

Figure 12:
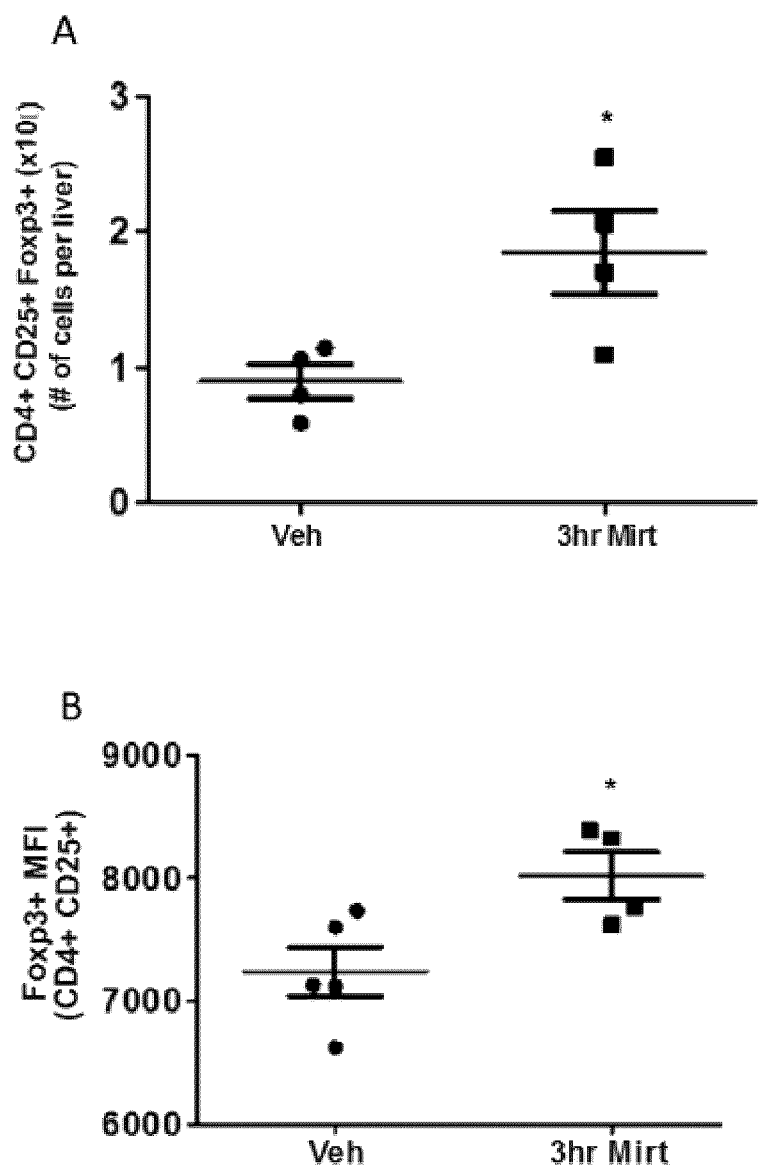
FIG. 12 depicts mirtazapine treatment significantly increases the number of Tregs within the liver (A), and per cell levels of FOXP3 expression in hepatic Tregs (B), 3 hrs post-treatment. n=4 and 5 mice per group. *p<0.03 vs respective vehicle treated.

We determined the impact of mirtazapine treatment (20 mg/kg ip) on hepatic numbers of Tregs, and on the per cell expression (as MFI) of FOXP3 for Tregs within the liver (FIGS. 12A and 12B). We found that mirtazapine treatment (3 hrs post-treatment) significantly increased numbers of Tregs (as CD4+CD25+FOXP3+ cells) within the liver (A), and enhanced cellular expression levels of FOXP3 in hepatic Tregs (as MFI) (B), compared to vehicle treated mice.

Example 4

Mirtazapine treatment shifts hepatic macrophages/monocytes from a pro-inflammatory to an anti-inflammatory/repair phenotype, which in turn results in attenuated inflammatory responses and enhanced repair processes in response to liver injury.

The aim here was to define the impact of mirtazapine on the phenotype of resident hepatic macrophage and monocyte populations, and delineate the mechanism(s) whereby mirtazapine directs the in situ reprogramming of these cells to shift them towards a more anti-inflammatory/repair phenotype.

Animal Models:

C57BL/6 male and female mice, and relevant transgenic mice strains (bred in house with breeding pairs purchased from Jackson labs), will be used. Mirtazapine (Tocris) will be administered by ip injection as an acute single dose (based on pilot as well as published data, we will use 20 mg/kg for acute dosing; but doses ranging from 1 to 20 mg/kg will be assessed) and experiments performed at 2, 4, 24, 48 and 72 hrs later. Mirtazapine effects will also be assessed after repeated daily dosing (10 mg/kg/day) for 7 days. Animals will be sacrificed under isoflurane anesthesia. We will investigate the impact of mirtazapine treatment on hepatic macrophages/monocytes in non-inflamed homeostatic conditions.

Statistical Analyses:

For experiments, 6-8 mice will typically be used per group to obtain statistical validity. Statistical significance will be assessed using appropriate statistical tests with GraphPad Instat 3 software (GraphPad Software Inc., La Jolla, Calif.).

Experimental Protocols

Part A: Define the Impact of Mirtazapine on Hepatic Macrophage (Kupffer Cell; KC) Activation and/or Polarization.

Figure 13:
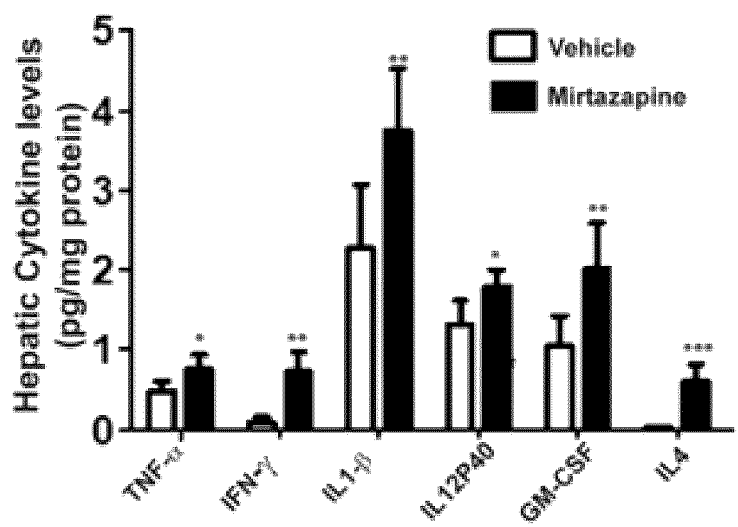
FIG. 13 depicts hepatic cytokine levels measured 4 hrs post-mirtazapine (20 mg/kg) or vehicle treatment. Bars represent data from 6 mice/grp. *p≤0.05, ≤0.01 and *≤0.001 vs corresponding vehicle group.
Figure 14:
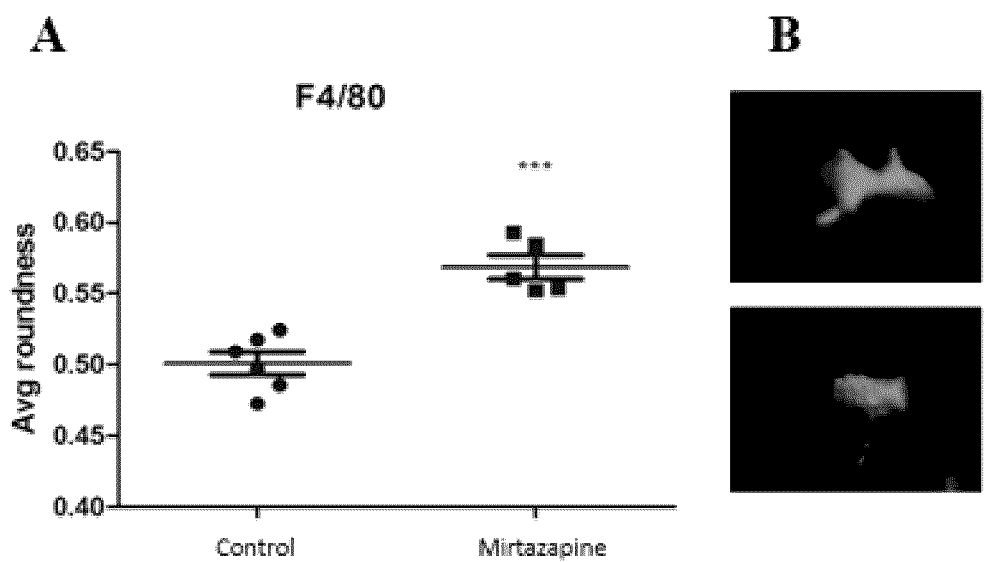
FIG. 14 depicts (A) average roundness score for hepatic F4/80+ cells in untreated vs mirtazapine treated mice. Analysis performed using LasX software where roundness score ranges from 0 (least circular) to 1 (most circular). B) representative 3D images of individual F4/80+ cells from control (top) and 1 hr after mirtazapine treatment (bottom), **p≤0.01 vs control.

Rationale and Relevant Preliminary Data: The normal liver macrophage pool consists of a large self-renewing, non-migratory population of KCs that are important for maintaining tissue homeostasis[1-3]. KCs are situated within the sinusoidal blood flow and are an essential component of hepatic innate immunity, playing key roles in inflammation and defense[2, 4]. In addition, KCs fulfill homeostatic functions important for normal liver physiology5. KCs are capable of considerable phenotypic plasticity and are highly sensitive to changes within the hepatic environment, including cytokines[2, 4, 6, 7]. In response to environmental cues, KCs are activated and can be polarized along a spectrum between M1-like (induced by IFNγ, TNFα, IL-1β, IL-12, TLR4 agonists) and M2-like (induced by IL-4, IL-13, IL-10) phenotypes[2, 4, 6, 7], and can dynamically shift between these phenotypic extremes in response to changes in their microenvironment[1, 2, 4, 8]. This shift is critical for regulating inflammatory and repair processes in the liver[1, 8, 9]. In pilot data we show that mirtazapine treatment strikingly alters the liver cytokine milieu within hours, increasing hepatic levels of both Th1- and Th2-like cytokines (FIG. 13). These cytokines have the capacity to polarize macrophages towards activated or repair phenotypes, depending on the mix and amount of cytokines and time of These observations suggest mirtazapine treatment rapidly alters hepatic cytokine levels and activates KCs; however, the impact of these changes on KC polarization/function remain unknown and will be delineated in the following series of experiments. exposure,[6, 7]. Moreover, these changes in the hepatic microenvironment are associated with activation of KCs (F4/80+), as reflected by a retraction of their cellular processes that extend along hepatic sinusoids, and a rounding of cell shape, as shown by intravital microscopy (IVM)(FIG. 14).

(i) Mirtazapine-Induced Changes in the Hepatic Cytokine Milieu and Delineation of Cellular Sources.

Macrophages can be classically (eg. IFNγ+LPS) or alternatively activated (eg. IL-4) by cytokines in the hepatic milieu[7, 10, 11]. Therefore, we will determine time-dependent (2-72 hrs post-mirtazapine/vehicle) dynamic mirtazapine-induced changes in hepatic expression of cytokines important for macrophage polarization (by Luminex® and qRT-PCR). Informed by the results of these studies of changes in hepatic cytokine levels, we will identify the important cell types producing key cytokines implicated in macrophage polarization shifts by FACS analyses of isolated hepatic immune cells (using our published protocols)[12-16]. The main hepatic cell types producing IFNγ include Th1 cells ($CD4^+$ $CD3^+$), type 1 innate lymphoid cells (ILC1; $CD3^-NK1.1^+$ $CD49a^+DX5^-$), classical NK cells ($NK1.1^+CD3^-CD49^-DX5^+$) and iNKT cells ($NK1.1^+CD3^+$), and those producing IL-4 mainly include Th2 cells, iNKT cells and ILC2's ($ICOS^+ST2^+CD127^+$ $KLRG1^+$)(but also potentially mast cells, neutrophils and eosinophils), all of which will be assayed in this aim[12, 16-19].

(ii) Impact of Mirtazapine-Induced Changes in Hepatic Milieu on Hepatic KC Activation and Phenotype.

Mirtazapine treatment rapidly activates KCs as reflected by shape changes (FIG. 14). However, it is unknown whether these changes are driven by specific alterations in the cytokine milieu induced by mirtazapine, and/or whether these changes are associated with alterations in KC phenotypic polarization. Therefore, at various times post-mirtazapine treatment (2-72 hrs) hepatic KCs ($F4/80^{hi}CD11b^{lo}$)[20] will be isolated[21, 22] and analyzed by FACS for: (a) changes in phenotypic markers reflecting classically activated ($NOS2^+CD80^+CD38^+$)[11] or alternatively activated/repair ($Arg1^+Fizz1^+CD206^+$) macrophages[11, 12, 23]. (b) changes in shape/size (forward vs side scatter) and cytokine production (eg. TNFα, IL-10) (by FACS)[14-16, 19, 24]. Based on our findings of mirtazapine-induced changes in hepatic levels of key cytokines identified in (Part A)(i) above, we will employ specific cytokine neutralization strategies using individual/combinations of neutralizing antibodies (using our published methods)[12, 14, 15, 19]. Neutralization experiments identifying cytokines of importance in driving mirtazapine related changes in KC activation and/or polarization will be further confirmed using specific gene KO mice[12, 16, 25]. If we identify a specific hepatic cell type that produces a cytokine identified by us as being potentially important in polarization of KCs after mirtazapine treatment, we will use cell-specific deletion strategies to confirm that the cell of interest is in fact responsible (using our published methods)[26, 27].

(iii) Potential Impact of Mirtazapine on KC Functional Capacity.

KCs are strategically positioned and reside as stationary macrophages within the liver sinusoids. A key role for KCs are to trap, phagocytose and remove pathogens in transit through the circulation[26, 28]. It is possible that mirtazapine-induced alterations in KC activation and/or phenotype polarization may alter KC function. To examine this we will determine whether mirtazapine treatment alters the phagocytic capacity of KCs, using fluorescent polychromatic microsphere (Polysciences, Inc.) capture in vivo using IVM (using our published methods)[26].

(iv) Defining Local Hepatic Vs Systemic Effects of Mirtazapine in Driving Changes in the Hepatic Microenvironment and KC Activation/Polarization.

To delineate local liver vs systemic effects of mirtazapine in inducing changes in the hepatic cytokine milieu and/or KC activation (as outlined above), we will use methods described by Menezes et al[29]. Briefly, for examining systemic effects, mirtazapine/vehicle will be administered ip as above. For local mirtazapine effects, a 1-$mm^2$ filter paper (grade 410; VRW Scientific) will be impregnated with mirtazapine (vehicle impregnated discs will be used as controls) and gently placed on the liver surface. At various times after treatment, liver punch biopsies will be obtained at filter paper sites (mirtazapine and vehicle) and analyzed for differences in cytokine expression (Luminex)12, 18. Additionally, KCs will be isolated from liver samples obtained from underneath the mirtazapine and vehicle impregnated filter paper sites and analyzed by FACS for changes in KC activation and polarization induced by local mirtazapine effects (markers as above in Part A(ii); our published methods)[12, 18, 20].

(v) Direct Mirtazapine-Induced Effects on Basal/Cytokine-Induced Macrophage Activation/Polarization.

It is possible that mirtazapine may have a direct effect on macrophage activation and polarization. To address this we will harvest and culture bone marrow-derived macrophages from mouse femurs and tibias, using standard techniques as we have described30. Initially, we will delineate whether mirtazapine at physiologically relevant concentrations (5-100 μg/L)[31] directly alters macrophage phenotype in vitro (determined by FACS, as in Part A(ii) above). In addition, we will determine the impact of mirtazapine vs vehicle treatment on macrophage phenotypic polarization after activation with IFNγ+LPS (20 ng/ml+100 ng/ml; induces classical activation) or IL-4 (20 ng/ml; induces alternative activation)[11,23] for 24 hrs. Culture supernatants will be harvested and mirtazapine-related changes in cytokine production measured (Luminex), and changes in macrophage phenotype polarization determined (by FACS).

Part B: Delineate the Impact of Mirtazapine in Regulating Dynamic Time-Dependent Changes in Hepatic Monocyte Populations.

Figure 15:
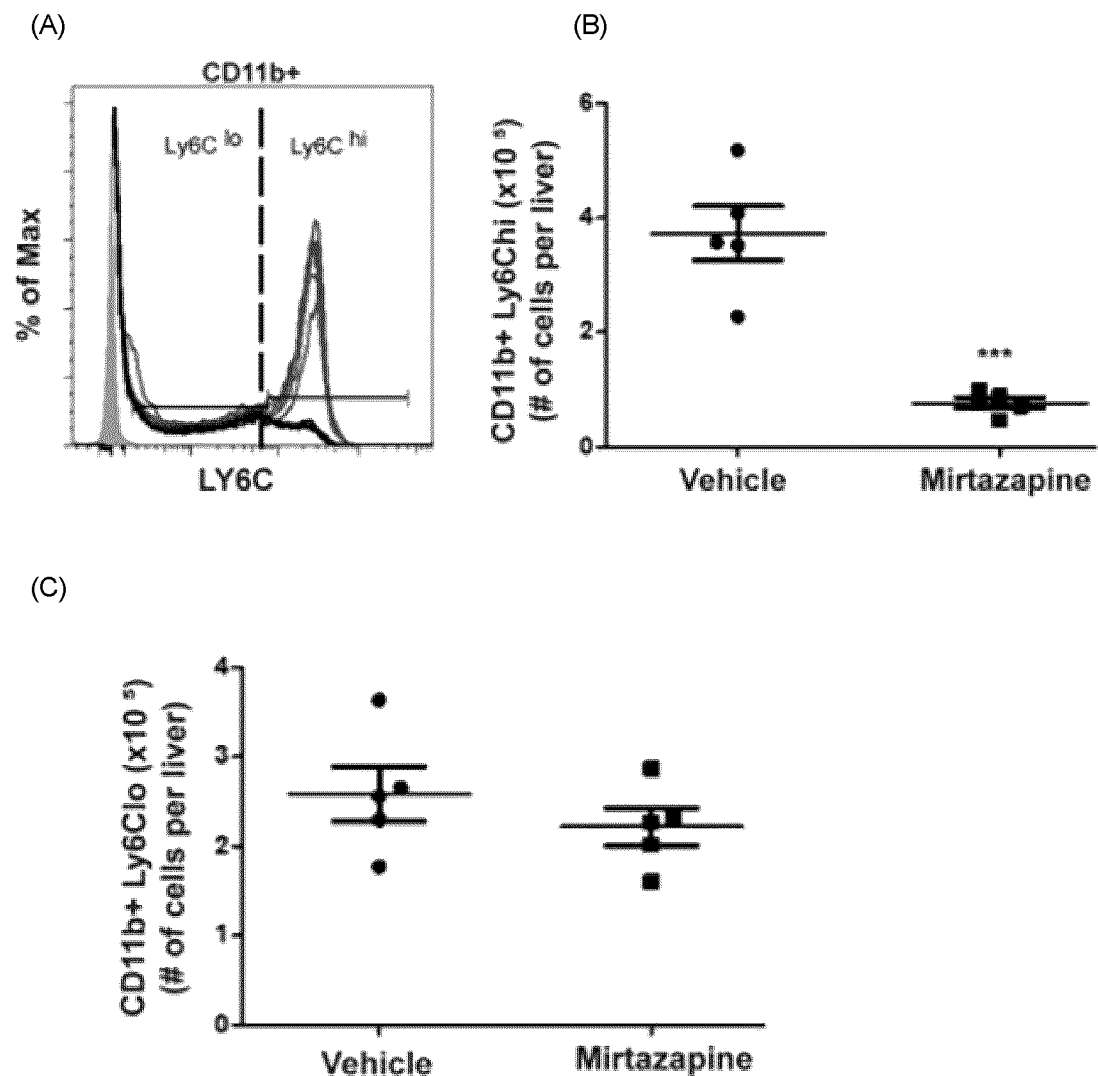
FIG. 15 depicts hepatic CD11b+Ly6C$^{hi}$ and CD11b+Ly6C$^{lo}$ monocyte populations 4 hrs after mirtazapine (20 mg/kg; black histograms) or vehicle (red histograms) treatment. (A) Left Panel: Flow cytometry histograms showing Ly6C$^{hi}$ inflammatory monocytes and Ly6C$^{lo}$ repair monocytes. Shaded histogram shows FMO. Mirtazapine treatment markedly reduced % hepatic inflammatory (LY6hi) monocytes vs vehicle; n=5 mice/grp (p≤0.001). (B) Middle Panel: CD11b+Ly6C$^{hi}$ monocytes (total # cells/liver) are significantly reduced in mirtazapine mice (***p≤0.003 vs vehicle; N=5/grp). (C) Right Panel: CD11b+Ly6C$^{lo}$ monocytes (total # cells/liver) are similar in mirtazapine treated vs vehicle. N=5/grp; NS.

Rationale and Relevant Preliminary Data:

In addition to KCs, the normal liver contains 2 main populations of tissue resident monocytes, a classical pro-inflammatory $CCR2^{hi}Ly6C^{hi}$ subset that patrols the liver sinusoids, and a non-patrolling $CX3CR1^{hi}Ly6C^{lo}$ subset important for tissue repair[12]. Moreover, liver injury leads to the rapid hepatic recruitment of inflammatory monocytes, giving rise over time to large numbers of monocyte-derived macrophages[1, 2, 12, 32-35]. Liver monocyte populations, like KCs, are very plastic and adapt their phenotype and function according to signals derived from the hepatic microenvironment[1, 2, 7, 8]. For example, during sterile liver injury, the cytokine IL-4 can induce a shift in hepatic monocytes from a pro-inflammatory to a pro-repair phenotype important for wound healing[12, 18]. In pilot studies we demonstrate that mirtazapine treatment causes a rapid striking reduction in hepatic $CD11b^+Ly6C^{hi}$ monocytes (inflammatory) within 4 hrs (FIG. 15), with no change in hepatic $CD11b^+Ly6C^{lo}$ (anti-inflammatory/repair) monocyte numbers (by FACS) (FIG. 15). This data suggests that $CD11b^+Ly6C^{hi}$ monocytes rapidly leave the liver after mirtazapine treatment (or less likely, given the timeframe, are dying). Furthermore, it is unlikely that CD11b+$Ly6C^{hi}$ monocytes are rapidly switching to become $CD11b^+Ly6C^{lo}$ monocytes as hepatic numbers of $CD11b^+Ly6C^{lo}$ monocytes are similar in vehicle and mirtazapine treated mice at 4 hrs post-treatment (FIG. 15). Therefore, in the following series of experiments we will determine how the rapid decline in hepatic $CD11b^+Ly6C^{hi}$ monocytes occurs after mirtazapine treatment.

(i) Mechanism(s) Driving Rapid Mirtazapine-Induced Reduction in Hepatic CD11b+Ly6C$^{hi}$ Monocytes:

(a) Mirtazapine-Induced Emigration of CD11b$^+$Ly6C$^{hi}$ Inflammatory Monocytes Out of the Liver:

Ly6Chi inflammatory monocytes express the adhesion molecules VLA-4 (binds to endothelial VCAM-1)36 and LFA-1 (binds to endothelial ICAM-1/2)36. In the context of liver inflammation a number of adhesion molecules appear to be important for Ly6Chi monocyte retention, including CD11 b, CD44, and ICAM-137. However, the relative importance of different monocyte adhesion mechanisms in the un-inflamed liver remains unknown. Moreover, endothelial expressed chemokines may also regulate hepatic monocyte retention via chemokine ligand: receptor interactions, including CCL2:CCR2, CCL3/CCL5: CCR1/CCR5, and CX3CL1:CX3CR1 respectively[33-35, 38]. Our pilot data suggests that mirtazapine may induce the rapid departure of Ly6Chi monocytes from the liver, possibly by altering adhesion molecule and chemokine/chemokine receptor expression. Therefore, we will use CCR2RFP/+ mice to determine the impact of mirtazapine treatment (vs vehicle) on CCR2$^+$ monocyte departure from the liver by simultaneously isolating RFP+ cells from the liver and blood and determining expression of the adhesion molecules LFA-1 and VLA-4 and chemokine receptor expression on CCR2$^{hi}$Ly6C$^{hi}$ (by FACS) monocytes at various times post-mirtazapine (or vehicle). It is important to supplement RFP positivity with FACS assessment to confirm that RFP+ cells are monocytes, as not all CCR2$^+$ cells are monocytes[12]. If differential cell departure from the liver occurs in response to mirtazapine, this will be identified by the observation of increased RFP+ CCR2$^{hi}$Ly6C$^{hi}$ monocytes in the peripheral blood, compared to the liver, for mirtazapine vs vehicle treated mice. In addition, we will delineate mirtazapine (vs vehicle) effects on hepatic endothelial expression of VCAM-1, ICAM-1/2, CD44 and chemokine expression by IVM and immunofluorescence microscopy (IFM), using our published methods[13-16, 19, 27, 39, 40]. Adhesion molecule expression can be regulated by cytokines within the hepatic milieu (eg. TNFα, IL-1β, IFNγ) and our pilot studies have indicated that hepatic levels of these cytokines are increased after mirtazapine treatment. Therefore, we will employ specific cytokine neutralization strategies (as previously described by us) to determine the relative importance in these cytokine changes in the liver in driving any changes in adhesion molecule expression, and ultimately the egress of CCR2hiLy6Chi monocytes out of the liver, after mirtazapine treatment[12, 14, 19, 26, 41].

(b) Reduced Survival of CCR2$^{hi}$Ly6C$^{hi}$ Monocytes in Response to Mirtazapine:

Mirtazapine may reduce CCR2$^{hi}$Ly6C$^{hi}$ monocyte survival by enhancing apoptosis. Therefore, we will determine time-dependent Annexin V and activated caspase-3 expression in CCR2$^{hi}$Ly6C$^{hi}$ cells after mirtazapine vs vehicle treatment (by FACS)[16]. Apoptosis of monocytes is regulated in part by Fas receptor (CD95) and TRAIL-R2 (DR5) expression[42]. Therefore, if we document enhanced apoptosis of CCR2$^{hi}$Ly6C$^{hi}$ monocytes after mirtazapine treatment, we will determine mirtazapine impact on CCR2$^{hi}$Ly6C$^{hi}$ monocyte expression of TRAIL-R2 and CD95 (by FACS)[42-44]. In addition, if we find that hepatic CCR2hiLy6Chi monocyte apoptosis is increased by mirtazapine, we will try to block this effect using specific blocking antibody treatments for TRAIL-R2 and CD95[43, 44].

Figure 16:
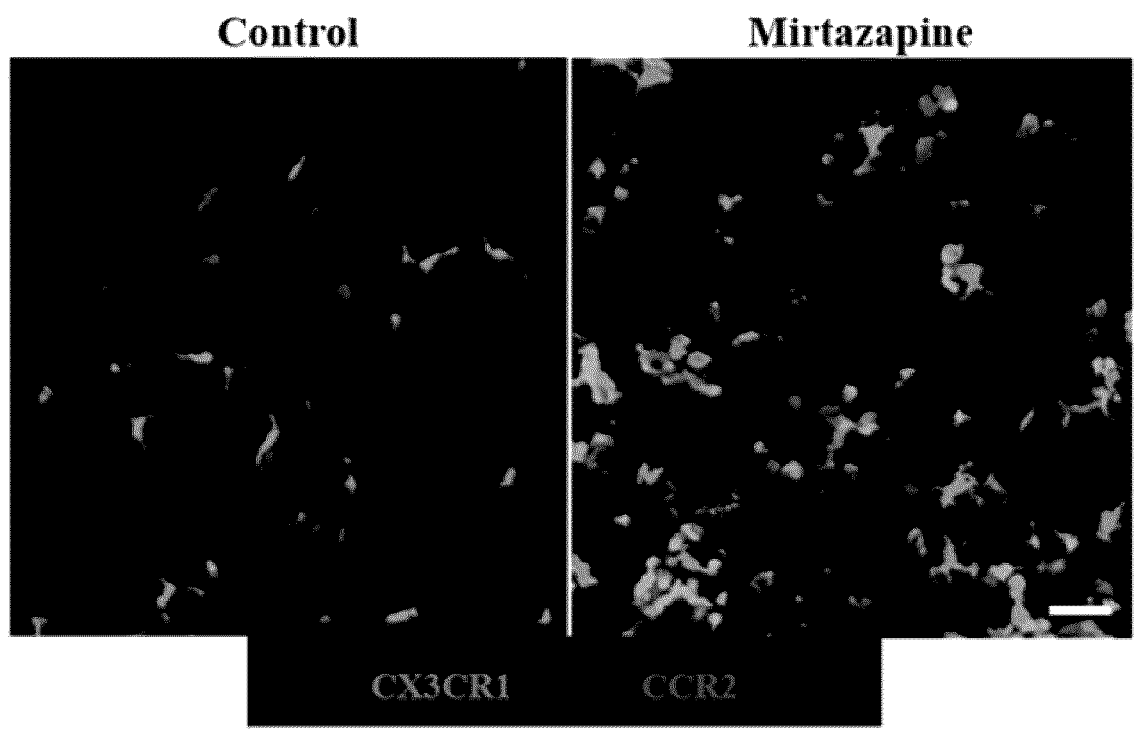
FIG. 16 depicts IVM images of liver from control or 20 h mirtazapine treated mice. CX3CR1+ (green) and CCR2+ (red). Cells double positive for CX3CR1 and CCR2 appear as yellow. Scale bar represents 100 uM.
Figure 17:
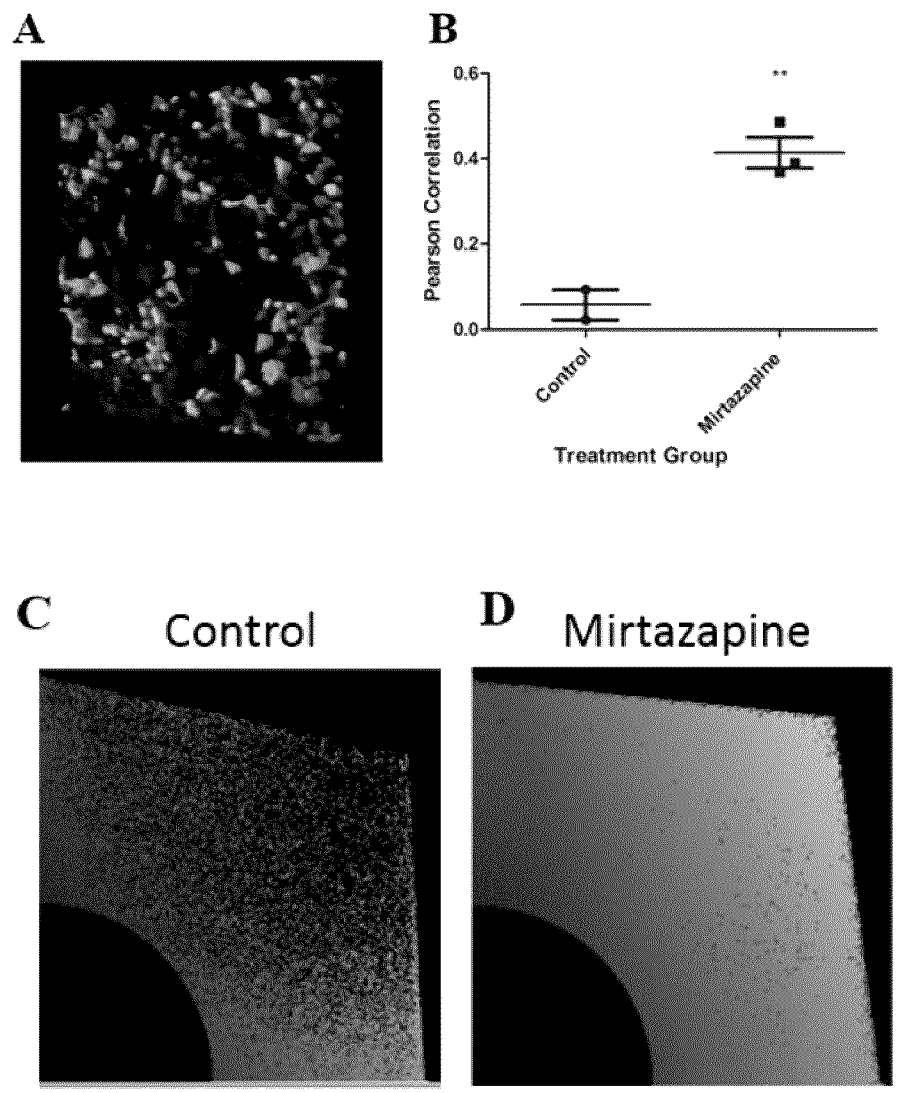
FIG. 17 depicts co-localization measurement of CCR2 and CX3CR1+ signals. A) 3D image reconstruction of mirtazapine-treated (20 hours) liver showing single positive CCR2 (red) and CX3CR1 (green) cells, and cells double positive for both markers (yellow). B) Graph showing the Pearson correlation coefficient image of livers from mice treated with mirtazapine for 20 hours compared to control (calculated using LasX software). The Pearson coefficient measures the linear strength of co-localization of red and green pixels within an image. C) Image analysis of control animals demonstrates pixels that are predominantly either red or green, as indicated by accumulation of pixels along the x and y ax3es. This indicates cells in the field of view are mainly CCR2+ (red_ or (CX3CR1 (green). D) Image analysis of mirtazapine treated mice demonstrate a full spectrum of pixel colors from red through yellow to green, representing the presence of both single positive (red or green) and double positive, CCR2+CX3CR1+ "yellow" cells within the field of view (FOV). Average of 36 FOV's per treatment group. Data shown as mean±SEM; **p<0.01.

(ii) Delayed mirtazapine-induced hepatic monocyte phenotypic shifts: In pilot studies we used CCR2$^{RFP/+}$ CX3CR1$^{GFP/+}$ transgenic reporter ("Christmas") mice, in which LY6C$^{hi}$ monocytes (ie CCR2$^{hi}$CX3CR1$^{lo}$) express RFP (red) and LY6C$^{lo}$ monocytes (ie. CX3CR1$^{hi}$CCR2$^{lo}$) express GFP (green) and CCR2$^{int}$CX3CR1$^{int}$ monocytes express both RFP and GFP (yellow), to examine potential delayed changes in monocyte populations within the liver after mirtazapine treatment. We found at ~20 hrs post-mirtazapine treatment, changes in hepatic monocyte populations in mirtazapine vs control mice. Specifically, control mice exhibited two relatively distinct populations, CCR2RFP expressing (red) inflammatory monocytes and CX3CR1GFP expressing (green) repair monocytes (FIG. 16, 17), whereas mirtazapine-treated mice exhibited an apparent increase in overall hepatic monocyte numbers coupled with the appearance of CCR2+CX3CR1+ double positive monocytes (yellow), by IVM (FIG. 16,17)[12, 18]. These observations are similar to those reported by dal-Secco et al after liver sterile burn injury (yellow monocytes were important for repair)[12], and suggest that at later time points (ie ~20 hrs) mirtazapine treatment leads to recruitment and phenotypic changes of hepatic monocyte populations; from a pro-inflammatory to repair phenotype.

(a) Defining the Time Course of Mirtazapine-Induced Shifts in the Hepatic Cytokine Microenvironment in Parallel to Changes in Hepatic Monocyte Populations:

Mirtazapine alters the hepatic cytokine milieu (FIG. 13), which over time may induce changes in resident hepatic monocyte phenotypes, and/or induce the recruitment of CCR2$^{hi}$ or CX3CR1$^{hi}$ monocytes to the liver, which subsequently are reprogrammed to phenotypically shift. To examine this we will employ CCR2RFP/+CX3CR1GFP/+ double reporter mice[12]. At various time points after mirtazapine or vehicle administration we will determine changes in predominant hepatic cytokine profiles (by Luminex; as in Part A (i)), and at the same time points isolate hepatic monocytes based on RFP and GFP expression in addition to LY6C and CD11 b markers (by FACS). In a model of sterile liver injury, hepatic monocyte reprogramming occurs between 24-72 hrs post-injury, from early CCR2$^{hi}$ to later CX3CR1$^{hi}$ monocyte phenotypes[12, 18]. Moreover, this monocyte phenotypic shift was driven by IL-4 and IL-10[12]. In pilot studies, we show that 4 hrs post-mirtazapine, hepatic IL-4 levels were 50-fold increased, but IL-10 levels were unchanged (FIG. 13). Therefore, we will determine the impact of neutralizing specific cytokines found to be altered by mirtazapine, either singly or in combination, using specific neutralizing antibodies (our published methods)[12, 14, 15, 19] to determine the impact on mirtazapine-induced hepatic monocyte phenotypic changes (by FACS).

(b) Role of Delayed Monocyte Recruitment to the Liver Post-Mirtazapine Treatment in Driving Hepatic Repair Monocyte Expansion:

It is possible that after early mirtazapine-induced egress of inflammatory monocytes from the liver, hepatic monocytes are repopulated through recruitment of CCR2$^{hi}$ monocytes from the bone marrow to the liver where they are converted to CCR2$^{int}$CX3CR1int monocytes, or alternatively CX3CR1$^{hi}$ monocytes may be recruited and then switched in situ to CCR2$^{int}$CX3CR1int monocytes. To examine this we will treat CCR2RFP/+ CX3CR1GFP/+ mice with mirtazapine or vehicle and at various times afterwards mice will be sacrificed and blood and hepatic monocytes isolated for FACS analysis to determine dynamic time-dependent changes in monocyte GFP, RFP and GFP/RFP co-expression (analyses will also include LY6C, CCR2 and CX3CR1 expression). CX3CR1hi monocytes are mainly recruited to the liver from the spleen, whereas CCR2$^{hi}$ cells are recruited from bone marrow[8, 34]. Therefore, we will define time-dependent mirtazapine-induced changes in splenic, blood, bone marrow and hepatic CX3CR1$^{hi}$Ly6C$^{lo}$ and CCR2$^{hi}$Ly6C$^{hi}$ monocytes (by FACS). If we document enhanced recruitment of CX3CR1hi monocytes from the spleen to the liver, we will repeat this experiment in splenectomized mice to document prevention of recruitment (using our published methods)[41]. To determine possible mirtazapine-induced preferential hepatic recruitment of CX3CR1$^{hi}$ vs CCR2$^{hi}$ monocytes, we will perform adoptive transfer experiments in wildtype mice immediately after mirtazapine and vehicle treatment by transferring a 50:50 mix of CCR2RFP/+ and CX3CR1GFP/GFP monocytes in one recipient (ie. receiving cells deficient for CX3CR1 but not CCR2) and in a different recipient transferring a 50:50 mix of CCR2RFP/RFP and CX3CR1GFP/+ (ie. receiving cells deficient for CCR2 but not CX3CR1), followed by cell isolation from the blood and liver for FACS analysis 4 and 24 hrs later, using our previously published methods[12].

(c) Delineating the Role of Kupffer Cell Activation in Driving Monocyte Population and Phenotype Shifts after Mirtazapine Treatment:

Kupffer cell activation occurs rapidly after mirtazapine treatment (FIG. 14. However, the impact of mirtazapine-induced activation of Kupffer cells upon subsequent hepatic monocyte changes is unknown. Therefore, we will treat mice with clodronate liposome (or PBS liposome)(purchased from clodronatelipisomes.org [Vrije Universiteit, Netherlands]) intravenously 200 μL/mouse 48 hrs prior to treatment with mirtazapine (Kupffer cells are depleted for up to 4 days whereas circulating monocytes repopulate by 24-48 hrs post-treatment)[20, 45] Experiments in (i) and (ii) above will then be repeated to determine the impact of Kupffer cell depletion on the measured parameters.

1. Krenkel O, Tacke F. Liver macrophages in tissue homeostasis and disease. Nat Rev Immunol 2017; 17:306-321.
2. Tacke F, Zimmermann H W. Macrophage heterogeneity in liver injury and fibrosis. J Hepatol 2014; 60:1090-6.
3. Eckert C, Klein N, Kornek M, et al. The complex myeloid network of the liver with diverse functional capacity at steady state and in inflammation. Front Immunol 2015; 6:179.
4. Sica A, Mantovani A. Macrophage plasticity and polarization: in vivo veritas. J Clin Invest 2012; 122:787-95.
5. Heymann F, Tacke F. Immunology in the liver—from homeostasis to disease. Nat Rev Gastroenterol Hepatol 2016; 13:88-110.
6. Porcheray F, Viaud S, Rimaniol A C, et al. Macrophage activation switching: an asset for the resolution of inflammation. Clin Exp Immunol 2005; 142:481-9.
7. Murray P J. Macrophage Polarization. Annu Rev Physiol 2017; 79:541-566.
8. Tacke F. Targeting hepatic macrophages to treat liver diseases. J Hepatol 2017; 66:1300-1312.
9. Dong Z, Wei H, Sun R, et al. The roles of innate immune cells in liver injury and regeneration. Cell Mol Immunol 2007; 4:241-52.
10. Murray P J, Allen J E, Biswas S K, et al. Macrophage activation and polarization: nomenclature and experimental guidelines. Immunity 2014; 41:14-20.
11. Jablonski K A, Amici S A, Webb L M, et al. Novel Markers to Delineate Murine M1 and M2 Macrophages. PLoS One 2015; 10:e0145342.
12. Dal-Secco D, Wang J, Zeng Z, et al. A dynamic spectrum of monocytes arising from the in situ reprogramming of CCR2+ monocytes at a site of sterile injury. J Exp Med 2015; 212:447-56.
13. Almishri W, Santodomingo-Garzon T, Le T, et al. TNFalpha Augments Cytokine-Induced NK Cell IFN-gamma Production through TNFR2. J Innate Immun 2016; 8:617-629.
14. Wondimu Z, Santodomingo-Garzon T, Le T, et al. Protective role of interleukin-17 in murine NKT cell-driven acute experimental hepatitis. Am J Pathol 2010; 177:2334-46.
15. Santodomingo-Garzon T, Han J, Le T, et al. Natural killer T cells regulate the homing of chemokine CXC receptor 3-positive regulatory T cells to the liver in mice. Hepatology 2009; 49:1267-76.
16. Ajuebor M N, Aspinall Al, Zhou F, et al. Lack of chemokine receptor CCR5 promotes murine fulminant liver failure by preventing the apoptosis of activated CD1d-restricted NKT cells. J Immunol 2005; 174:8027-37.
17. Liu M, Zhang C. The Role of Innate Lymphoid Cells in Immune-Mediated Liver Diseases. Front Immunol 2017; 8:695.
18. Liew P X, Lee W Y, Kubes P. iNKT Cells Orchestrate a Switch from Inflammation to Resolution of Sterile Liver Injury. Immunity 2017; 47:752-765 e5.
19. Ajuebor M N, Hogaboam C M, Le T, et al. CCL3/MIP-1alpha is pro-inflammatory in murine T cell-mediated hepatitis by recruiting CCR1-expressing CD4(+) T cells to the liver. Eur J Immunol 2004; 34:2907-18.
20. Wang J, Kubes P. A Reservoir of Mature Cavity Macrophages that Can Rapidly Invade Visceral Organs to Affect Tissue Repair. Cell 2016; 165:668-78.
21. Kinoshita M, Uchida T, Sato A, et al. Characterization of two F4/80-positive Kupffer cell subsets by their function and phenotype in mice. J Hepatol 2010; 53:903-10.
22. Li P Z, Li J Z, Li M, et al. An efficient method to isolate and culture mouse Kupffer cells. Immunol Lett 2014; 158:52-6.
23. Misharin A V, Morales-Nebreda L, Mutlu G M, et al. Flow cytometric analysis of macrophages and dendritic cell subsets in the mouse lung. Am J Respir Cell Mol Biol 2013; 49:503-10.
24. Daigneault M, Preston J A, Marriott H M, et al. The identification of markers of macrophage differentiation in PMA-stimulated THP-1 cells and monocyte-derived macrophages. PLoS One 2010; 5:e8668.
25. Nguyen K, D'Mello C, Le T, et al. Regulatory T cells suppress sickness behaviour development without altering liver injury in cholestatic mice. J Hepatol 2012; 56:626-31.
26. Wong C H, Jenne C N, Petri B, et al. Nucleation of platelets with blood-borne pathogens on Kupffer cells precedes other innate immunity and contributes to bacterial clearance. Nat Immunol 2013; 14:785-92.
27. McDonald B, Jenne C N, Zhuo L, et al. Kupffer cells and activation of endothelial TLR4 coordinate neutrophil adhesion within liver sinusoids during endotoxemia. Am J Physiol Gastrointest Liver Physiol 2013; 305:G797-806.
28. Lee W Y, Moriarty T J, Wong C H, et al. An intravascular immune response to Borrelia burgdorferi involves Kupffer cells and iNKT cells. Nat Immunol 2010; 11:295-302.
29. Menezes G B, Lee W Y, Zhou H, et al. Selective down-regulation of neutrophil Mac-1 in endotoxemic hepatic microcirculation via IL-10. J Immunol 2009; 183:7557-68.

30. Komada T, Chung H, Lau A, et al. Macrophage Uptake of Necrotic Cell DNA Activates the AIM2 Inflammasome to Regulate a Proinflammatory Phenotype in CKD. J Am Soc Nephrol 2018.
31. Anttila S A, Leinonen E V. A review of the pharmacological and clinical profile of mirtazapine. CNS Drug Rev 2001; 7:249-64.
32. Ramachandran P, Pellicoro A, Vernon M A, et al. Differential Ly-6C expression identifies the recruited macrophage phenotype, which orchestrates the regression of murine liver fibrosis. Proc Natl Acad Sci USA 2012; 109:E3186-95.
33. Brempelis K J, Crispe I N. Infiltrating monocytes in liver injury and repair. Clin Transl Immunology 2016; 5:e113.
34. Murray P J. Immune regulation by monocytes. Semin Immunol 2017.
35. Shi C, Pamer E G. Monocyte recruitment during infection and inflammation. Nat Rev Immunol 2011; 11:762-74.
36. Gerhardt T, Ley K. Monocyte trafficking across the vessel wall. Cardiovasc Res 2015; 107:321-30.
37. Shi C, Velazquez P, Hohl T M, et al. Monocyte trafficking to hepatic sites of bacterial infection is chemokine independent and directed by focal intercellular adhesion molecule-1 expression. J Immunol 2010; 184:6266-74.
38. Sahin H, Trautwein C, Wasmuth H E. Functional role of chemokines in liver disease models. Nat Rev Gastroenterol Hepatol 2010; 7:682-90.
39. Jenne C N, Wong C H, Zemp F J, et al. Neutrophils recruited to sites of infection protect from virus challenge by releasing neutrophil extracellular traps. Cell Host Microbe 2013; 13:169-80.
40. Bonder C S, Norman M U, Swain M G, et al. Rules of recruitment for Th1 and Th2 lymphocytes in inflamed liver: a role for alpha-4 integrin and vascular adhesion protein-1. Immunity 2005; 23:153-63.
41. Almishri W, Deans J, Swain M G. Rapid activation and hepatic recruitment of innate-like regulatory B cells after invariant NKT cell stimulation in mice. J Hepatol 2015; 63:943-51.
42. Parihar A, Eubank T D, Doseff A I. Monocytes and macrophages regulate immunity through dynamic networks of survival and cell death. J Innate Immun 2010; 2:204-15.
43. Janssen W J, Barthel L, Muldrow A, et al. Fas determines differential fates of resident and recruited macrophages during resolution of acute lung injury. Am J Respir Crit Care Med 2011; 184:547-60.
44. Liguori M, Buracchi C, Pasqualini F, et al. Functional TRAIL receptors in monocytes and tumor-associated macrophages: A possible targeting pathway in the tumor microenvironment. Oncotarget 2016; 7:41662-41676.
45. Yamamoto T, Naito M, Moriyama H, et al. Repopulation of murine Kupffer cells after intravenous administration of liposome-encapsulated dichloromethylene diphosphonate. Am J Pathol 1996; 149:1271-86.
46. Wang J, Hossain M, Thanabalasuriar A, et al. Visualizing the function and fate of neutrophils in sterile injury and repair. Science 2017; 358:111-116.
47. Patterson G H, Lippincott-Schwartz J. A photoactivatable GFP for selective photolabeling of proteins and cells. Science 2002; 297:1873-7.

Example 5

Dendritic cells (DCs) control immune responses and are central to the development of immune memory and tolerance (Chen K et al. Int Immunopharmacol. 2016). Dendritic cells have a pivotal role in sensing pathogens and initiating adaptive immune responses by activation and regulation of T-lymphocyte responses (Szabo G et al. Semin Liver Dis. 2007). They represent the most potent antigen-presenting cells of the immune system (Adema G J. Immunol Lett. 2009), and are responsible for initiating the phase of immunity dominated by the action of pathogen-specific T and B cells (Joffre O et al. Immunol Rev. 2009). Under steady-state conditions, monocyte-derived cells can develop into liver dendritic cells. DCs are commonly located in portal tracts in healthy liver. During inflammation, they form periportal lymphoid structures, which serve as a priming site for liver-infiltrating T cells; a process which critically regulates subsequent hepatic immune responses (Heymann F, Tacke F. Nat Rev Gastroenterol Hepatol. 2016; Strauss O et al. J Hepatol. 2015).

Therefore, in the studies outlined below we determined the impact of mirtazapine treatment (20 mg/kg ip) on hepatic dendritic cells using flow cytometry.

Results

Figure 18:
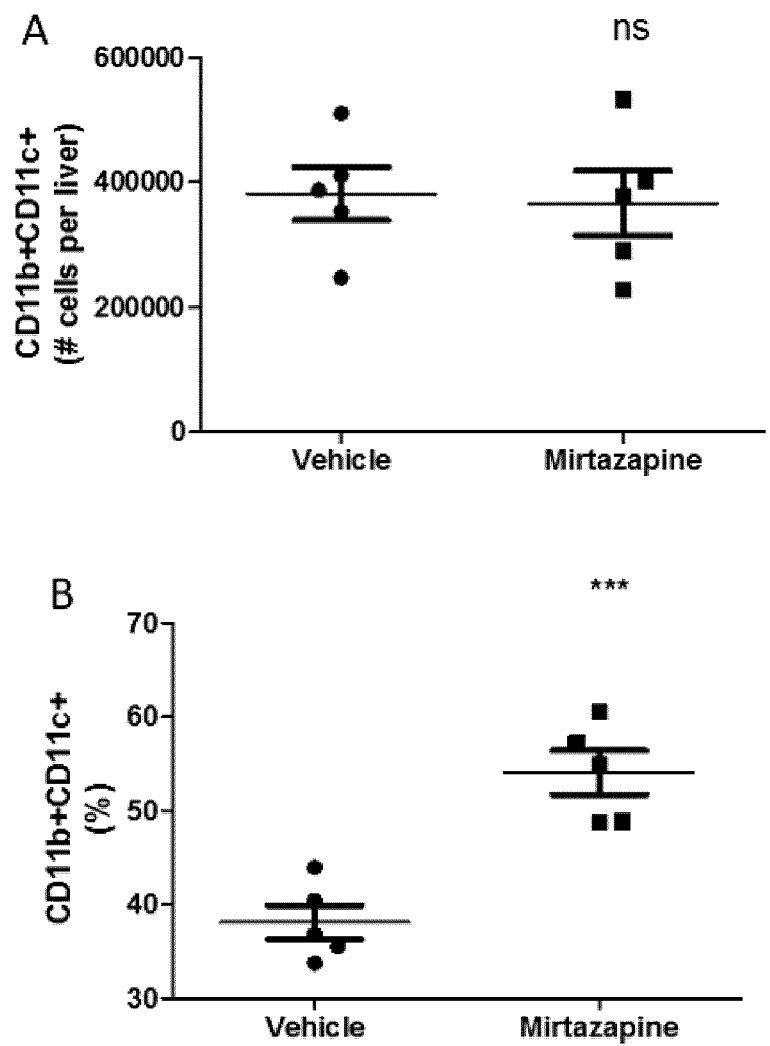
FIG. 18 depicts Total numbers of CD11b+CD11c+(ie. conventional; Dress R J et al. Immunol Cell Biol. 2018; Macri C et al. Semin Cell Dev Biol. 2017) dendritic cells within the liver were similar in vehicle treated and mirtazapine treated mice (3 hrs post-treatment)(A). However, hepatic CD11b+CD11c+ dendritic cells were relatively enriched as a % of total CD11 b+ cells post-mirtazapine treatment (B; ***p<0.0007; n=5 mice/grp).

Total numbers of $CD11b^+CD11c^+$ (ie. conventional; Dress R J et al. Immunol Cell Biol. 2018; Macri C et al. Semin Cell Dev Biol. 2017) dendritic cells within the liver were similar in vehicle treated and mirtazapine treated mice (3 hrs post-treatment)(FIG. 18 A). However, hepatic $CD11b^+CD11c^+$ dendritic cells were relatively enriched as a % of total $CD11 b^+$ cells post-mirtazapine treatment (FIG. 18B; ***$p<0.0007$; n=5 mice/grp).

Our findings that Mirtazapine treatment enriches conventional dendritic cells within the liver, is highly novel and represents a safe and potentially effective way of targeted enhancement of hepatic dendritic cell effects within the liver.

The unique liver immune microenvironment favors resistance to inflammation that promotes normal physiological function (reviewed in Dou L et al. Semin Liver Dis. 2018). Hepatic dendritic cells (HDCs) initiate and orchestrate immune responses depending on signals they receive from the local environment and are thought to contribute to liver tolerance. Thus, HDCs facilitate impaired T cell responses that are observed in persistent viral infections and liver allograft transplantation. HDCs also participate in anti-inflammatory responses in liver ischemia-reperfusion injury (IRI). Moreover, they promote the regression of fibrosis from various fibrogenic liver injuries. These findings suggest that HDCs regulate intrahepatic immune responses, allowing the liver to maintain homeostasis and integrity even under pathological conditions (reviewed in Dou L et al. Semin Liver Dis. 2018).

Our findings may represent a method whereby mirtazapine can enrich hepatic DC's. DC's can regulate both innate and adaptive immunity (Banchereau J and Steinman R M. Nature 1998; Steinman R M et al. Ann Rev Immunol. 2003). Multiple subsets of rodent and human DC (Liu Y J. Cell 2001; H. Ueno et al. Immunol Rev. 2007) with the ability to regulate immune responses has potential wide applicability, including (in rodents) in the treatment of organ transplant rejection, graft-versus-host disease (GVHD) following hematopoietic (HSC) transplantation and various autoimmune disorders (Morelli A E and Thomson A W. Nat Rev Immunol. 2007; Stenger E O et al. Blood. 2012; Rogers N M et al. Am J Transplant 2013; Hilkens C M et al. Int Rev Immunol. 2010; Thomson A W et al. Human Immunol. 2018).

Example 6

B cells play a central role in inflammatory and autoimmune processes (Theofilopoulos A N et al. Nat Immunol.

2017; Salinas G F et al. Clin Immunol. 2013). Moreover, B cells are the major lymphocyte population within the liver and critically regulate hepatic immune-mediated liver injury (and autoimmunity; Moritoki Y. et al. Autoimmunity Rev. 2006; Almishri W. et al. J Hepatol. 2015) and liver fibrotic processes (Novobrantseva T I et al. JCI. 2005). Antidepressants are frequently prescribed to liver disease patients, but their impact on liver immunity is poorly understood. Mirtazapine (mirt) is a widely used safe atypical antidepressant, which we have recently shown prevents adverse liver outcomes in mouse and human immune-mediated liver injury. Therefore, we examined the impact of mirt treatment on hepatic B cells Shaheen A et al. PLOSone 2018).

Methods

Male C57BL/6 mice (age 8-10 wks) were treated with mirt (20 mg/kg ip) or vehicle and livers removed 3-5 hrs later for B cell isolation and characterization by flow cytometry (FACS). Similarly peripheral blood and splenic B cells numbers were determined by FACS. Liver cytokine and chemokine levels were measured by Luminex®.

Results (A) Mirtazapine Effects on Hepatic B Cells:

Mirt treatment resulted in a rapid (within 3-5 hours), profound ~48% decrease in total hepatic B cell (as IgM+ cells) numbers (veh 10.2 ($\times 10^5$)+0.8 [SEM] vs mirt 5.3 ($\times 10^5$)+0.4 cells/liver; p<0.0005; n=5 mice/grp).

(i) The population that decreased within the liver post-mirtazapine treatment were composed of mainly B2 B cells (ie. classical B cells, vs B1 B cells which are innate/regulatory B cells). B2 B cells are the main B cell population that has been implicated in the regulation of numerous autoimmune diseases, mainly through antibody production and antigen presentation (% B2 cells of IgM+B cells in liver: veh 41.4%+1.5% vs 5 hr post-mirtazapine treatment 29.6%+2.3%; n=5 mice/grp; p<0.002). In contrast, B1a B cells were enriched within the liver post-mirtazapine treatment (vehicle 23.1%_1.1% vs 5 hrs post-mirtazapine 32.4%+1.5%; p<0.001; n=5/mice/grp) whereas hepatic B1b B cells remained unchanged post-mirtazpaine treatment (veh 22.3%+1.3% vs 5 hrs post-mirtazapine 23.5%+1.4%; NS; n=5 mice/grp). Experiment was repeated 3 times with similar results.

(ii) We next characterized the B cell population remaining within the liver post-mirt treatment. This population was enriched in B1 B cells (ie. innate B cells)(. The adhesion molecule VLA-4 and chemokine receptor CXCR3 are important for hepatic B cell recruitment and retention. The frequency of VLA-4+ hepatic B cells was significantly reduced after mirt treatment (veh 67.1+1.3% vs mirt 61.9+1.8%; p<0.05; n=5/grp), despite clear upregulation of hepatic VCAM-1 expression post-mirt (by immunohistochemistry). In contrast, hepatic CXCR3+B cells were enriched after mirt treatment (veh 36.9+0.3% vs mirt 47.5+1.4%; p<0.0001), and B cell CXCR3 expression levels were increased (as MFI; veh 9118±392.2 vs mirt 12180±315.9; p<0.0003)(n=5 mice/grp). Closer analysis of hepatic CXCR3+ B cells indicated clear $CXCR3^{hi}$ and $CXCR3^{lo}$ populations (by MFI). Mirt treatment did not significantly alter hepatic CXCR3lo B cells, but markedly enriched $CXCR3^{hi}$ B cells (veh 17.8±1.3% vs mirt 30.7±1.5%; p<0.0002; n=5/grp). In addition, VLA-4+B cells were enriched amongst hepatic CXCR3hi B cells post-mirt (VLA-4+CXCR3hi B cells: veh 8.3+0.4% vs mirt 16.1±1.7%; p<0.002; n=5/grp). Mirt treatment strikingly elevated hepatic CXCL10 levels as measured by Luminex® (CXCL10 is an important CXCR3 ligand; ~120-fold; p<0.004; n=6 mice/grp); being produced mainly by hepatic macrophages (determined by immunohistochemistry. Confirmed using flow cytometry which identified CD11b+ $Ly6C^{hi}$ monocytes as the main cell producing CXCL10: veh 2.4%+0.3% vs 3 hrs post-mirtazapine 12.2%±3.8%; p<0.03; n=5 mice/grp). In parallel to changes in hepatic CXCL109 levels, mirtazapine treatment resulted in a significant increase in plasma levels of CXCL10 at 5 hrs post-treatment (ELISA: veh 25.4±1.3 pg/ml vs 5 hrs post-mirtazapine 138.4±24.4 pg/ml; p<0.002; n=5 mice/grp).

IFNγ is a key driver of CXCL10 production, and mirt treatment resulted in a significant ~8-fold increase in hepatic IFNγ levels (measured by Luminex®) compared to veh treated controls (p≤0.0001; n=6 mice/grp).

Figure 19:
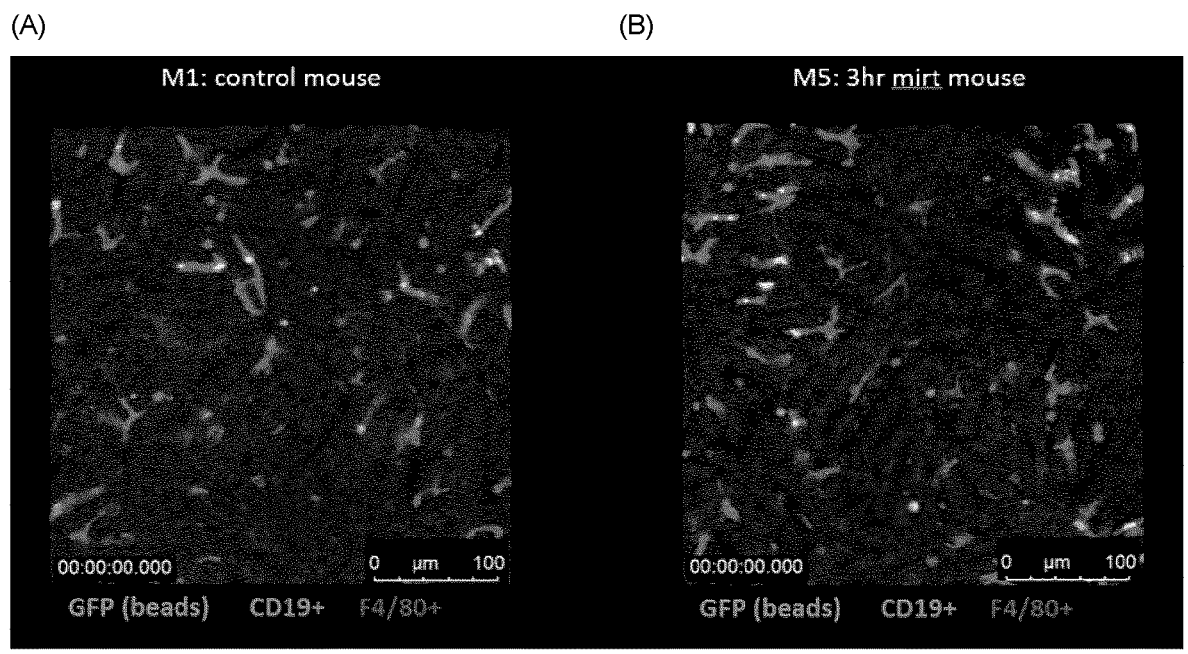
FIG. 19 depicts intravital microscopy (IVM) studies suggest that B cells (ie. CD19+ cells) remaining in the liver post-mirtazpaine treatment are more likely to be in close contact with hepatic F4/80+ macrophages (representative IVM image shown; *note: GFP beads (green) were used to examine bead capture by liver macrophages), panel (A) depicts M1: control mouse, Panel (B) depicts M5: 3 hr mirt mouse.

Intravital microscopy (IVM) studies (FIG. 19A&B) suggest that B cells (ie. $CD19^+$ cells) remaining in the liver post-mirtazpaine treatment are more likely to be in close contact with hepatic $F4/80^+$ macrophages (representative IVM image shown; *note: GFP beads (green) were used to examine bead capture by liver macrophages).

Figure 20:
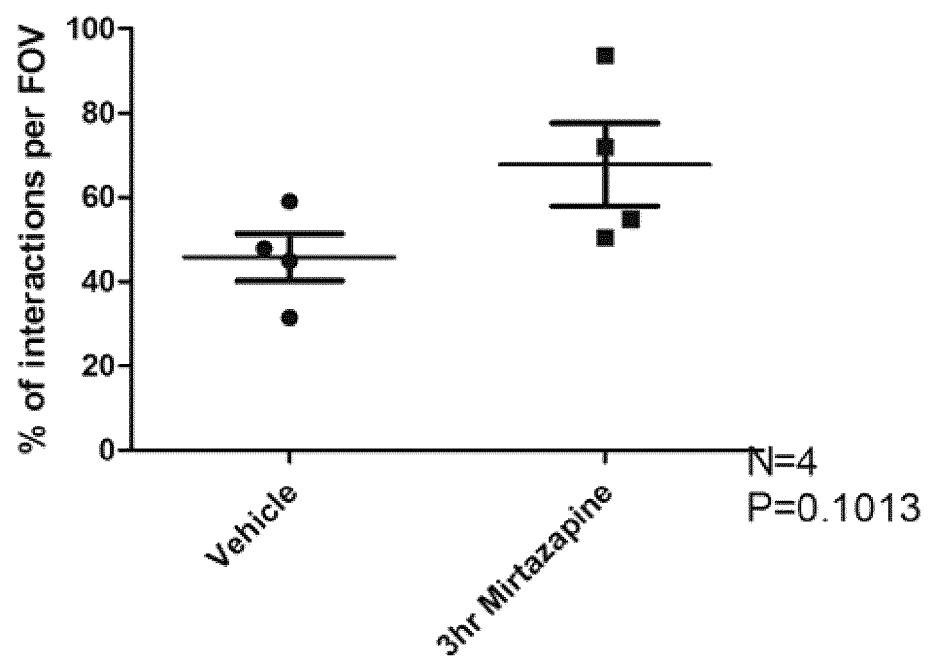
FIG. 20 depicts a summary of from IVM experiments showing trend towards increased interactions between hepatic B cells (CD19+ cells) and hepatic macrophages (F4/80+ cells) in mice 3 hrs post-mirtazapine (20 mg/kg) treatment vs vehicle treated controls.

FIG. 20 depicts a summary of preliminary data from IVM experiments showing trend towards increased interactions between hepatic B cells ($CD19^+$ cells) and hepatic macrophages ($F4/80^+$ cells) in mice 3 hrs post-mirtazapine (20 mg/kg) treatment vs vehicle treated controls.

(B) Mirtazapine Effects on Peripheral Blood and Splenic B Cells:

We found that the mirtazapine-induced reduction in hepatic B cell numbers was associated with changes in peripheral blood and splenic B cell populations in mice.

Specifically, at 5 hrs post-mirtazapine treatment (20 mg/kg ip) a highly significant drop in peripheral blood B cells (as % of total CD45+ leukocytes) was noted by flow cytometry, compared to vehicle treated mice (FIG. 21A); a drop that was paralleled by similar changes in splenic B cell numbers (FIG. 21B).

(A) Mirtazapine for Treatment of Liver Disease:

Mirtazapine treatment rapidly (within hours) profoundly reduces hepatic B cell numbers, and alters the predominant phenotype composition of B cells within the liver; a highly novel observation. Given the important role played by B cells in hepatic inflammatory and autoimmune processes, and in liver fibrosis, our findings have significant implications for a potential beneficial role for mirtazapine treatment in numerous liver diseases.

We also have identified that mirtazapine treatment strikingly reduces peripheral blood circulating B cells (and splenic B cells)(FIG. 20). Interestingly, a similar pattern of changes in tissue and blood B cell numbers has been reported previously with the drug FTY720, which has been approved for treatment of multiple sclerosis (Chun J and Hartung H P. Clin Neuropharmacol. 2010). Adaptive immune responses depend on T and B lymphocytes travelling between secondary lymphoid organs to survey for antigens. After activation in lymphoid organs, lymphocytes must again return to the circulation to reach sites of infection or immune-mediated injury. This process is critically dependent on lymphocyte cell surface expression of the receptor S1P1. The immunosuppressant drug, FTY720, inhibits lymphocyte emigration from lymphoid organs by inducing downregulation of expression of the receptor S1P1 on both T and B lymphocytes (Matloubian M et al. Nature. 2004) and leading to lymphocyte sequestration within lymph nodes. This FYT720-mediated lymphocyte sequestration has been directly linked to improvement in autoimmune diseases such as MS. The identification of a similar mode of action for mirtazapine, as has been reported for FTY720, would be a very novel and highly clinically relevant mechanism of action for mirtazapine for the potential treatment of AID's.

To further address this, we will determine whether mirtazapine treatment downregulates B lymphocyte cell surface expression of 51P1 in mice treated with mirtazapine (20 mg/kg) in vivo and in murine and human B cells in vitro (by flow cytometry) (Matloubian M et al. Nature. 2004). In additional experiments we will determine whether the reduction in tissue and peripheral blood B cell numbers after mirtazapine treatment is associated with an accumulation of B (and T) lymphocytes in peripheral lymph nodes, as has been reported with FTY720 (Morris M A et al. Eur J Inmmunol. 2005).

Our findings that Mirtazapine induces decreased numbers of B cells within the liver, is highly novel and represents a safe and potentially effective way of potentially targeting a reduction in hepatic B cell effects in the context of liver disease.

Mirtazapine may have similar effects in other tissues that are targets for inflammatory and/or autoimmune disease (Hofmann K et al. Front Immunol. 2018; Dorner T et al. Pharmacol Ther. 2010), including: (i) inflammatory skin diseases such as autoimmune blistering disorders, collagen vascular diseases, and atopic dermatitis (Nagel A et al. J Invest Dermatol. 2009), multiple sclerosis (Li R et al. Nat Immunol 2018), rheumatic diseases (eg. rheumatoid arthritis, systemic sclerosis, Sjögren's syndrome and systemic lupus erythematosus; Schioppo T and Ingegnoli F. Drug Des Devel Ther. 2017; Cohen M D and Keystone E. Rheumatol Ther. 2015; Sakkas L I and Bogdanos D P. Autoimmun Rev. 2016).

In addition, mirtazapine may have a beneficial impact on solid organ transplant, including liver, renal, and heart transplantation (Chesneau M et al. Human Immunol. 2018; Peng B et al. Cell Death Dis. 2018; Chu Z et al. Exp Rev Clin Immunol. 2018; Karahan G E et al. Front Immunol. 2017; Alsughayyir J et al. Front Immunol. 2017), as well as in hematopoietic stem cell transplantation (chronic GVHD; Kharfan-Dabaja M A et al. Biol Blood Marrow Transplant. 2009).

Example 7

Table 3 depicts the results of a retrospective cohort study using patient (median follow-up éindividual 7.4 yrs; interquartile 10.3) in the UK THIN database. Patients who were prescribed mirtazapine. 90 day (a=186,411) identified and compared to a matched patient cohort (2:1) not exposed to mirtazapine (n=372,822). Out models were adjusted for depression, use of other antidepressants, comorbidity status, smoking and alcohol consumption. Mirtazapine was protective against developing all three AID's are reflected by the adjusted IRR.

TABLE 3

|  | Rheumatoid Arthritis | Multiple Sclerosis | Psoriasis |
|---|---|---|---|
| Adjusted Incidence Rate Ratio (adjusted IRR) | 0.55 | 0.80 | 0.93 |
| 95% Confidence Interval (CI) | 0.51-0.60 | 0.71-0.88 | 0.88-0.98 |

Example 8

The antigen-induced arthritis (AIA) mouse model is a well-characterized model that is extensively used to provide insights into the pathogenesis of RA.

AIA is critically dependent on an early innate immune response (within 24 hrs post-induction) mediated by synovial TM's and neutrophils which drive subsequent adaptive immune responses and chronic joint inflammation. Proinflammatory cytokines (eg. TNFα, IL-17A and IL-1) and chemokines (eg. CXCL1, CXCL2) recruit neutrophils to the joint in this model.

AIA is induced by the intradermal (tail base) injection of 500 µg methylated BSA (mBSA; Sigma) in 50 µl saline+ complete Freund's adjuvant (CFA; Sigma) on day 0. 14 days later mice receive an antigen challenge with mBSA (10 µg/10 µl saline) injection into the left knee joint. At various time points after antigen challenge knee swelling is assessed using calipers, and the knee cavity exposed and inflammatory response and tissue injury assessed by immune cell analyses (cell phenotyping by FACS, using our published protocols), cytokine/chemokine expression (by Luminex® and qRT-PCR), and scoring of histological joint damage. Assessment of joint innate immune responses will occur at 24 and 48 hrs post-antigen challenge42. Mice with AIA exhibit hypernociception related to joint inflammation, mediated by neutrophil recruitment and increased joint TNFα and IL-1 expression; a finding commonly observed in RA patients. Hypernociception was measured before and 24 hrs post-antigen challenge using an automatic dynamic plantar algesiometer (Hugo Basile Inc).

Figure 21:
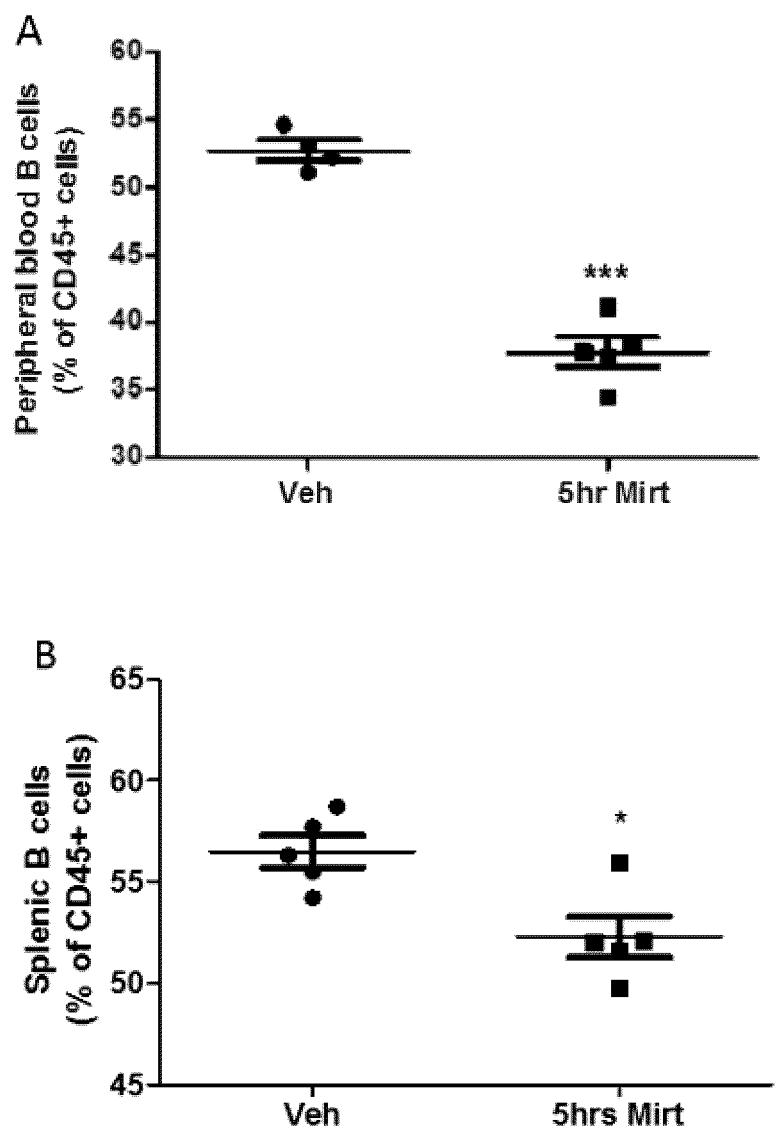
FIG. 21 depicts that the mirtazapine-induced reduction in hepatic B cell numbers was associated with changes in peripheral blood and splenic B cell populations in mice (A) at 5 hrs post-mirtazapine treatment (20 mg/kg ip) a highly significant drop in peripheral blood B cells (as % of total $CD45^+$ leukocytes) was noted by flow cytometry, compared to vehicle treated mice; (B) a drop that was paralleled by similar changes in splenic B cell numbers.

Our data shows that mirtazapine (20 mg/kg) reduces joint total neutrophil recruitment, synovial fluid TNFα and IL-1α (but not CXCL1) levels, and attenuates AIA-induced hypernociception 24 hrs post-antigen challenge FIG. 21 depicts (A) recruitment of neutrophils into arthritic knee synovial space 24 hrs port-antigen (mBSA) challenged is prevented by mirtazapine treatment (mBSA+ mirt). **p≤0.01 vs vehicle treated groups; *p≤0.01 vs vehicle treated group; *≤0.05 vs mBSA+mirt group. (B) antigen-induced arthritis induces hypernociception in affected joint (i.e., decreased withdrawal threshold in mBSA+vej group) that is attenuated by mirtazapine treatment. **≤0.01 vs mBSA+mirt group, and 0.001 vs control vehicle groups; *p≤0.001 vs control vehicle groups N=4-5 mice/grp.

Figure 22:
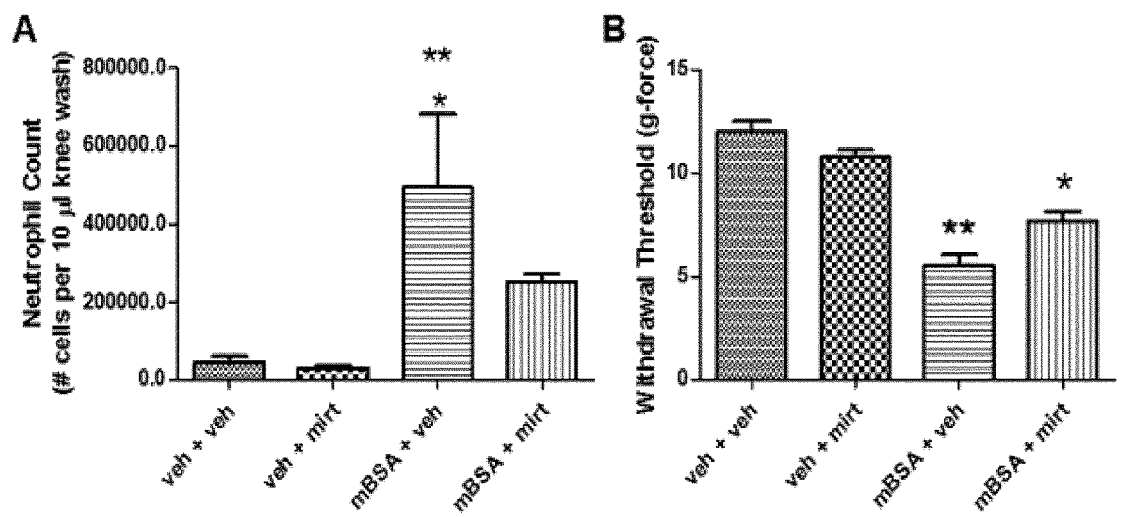
FIG. 22 depicts (A) recruitment of neutrophils into arthritic knee synovial space 24 hrs port-antigen (mBSA) challenged is prevented by mirtazapine treatment (mBSA+mirt). **$p \leq 0.01$ vs vehicle treated groups; *$p \leq 0.01$ vs vehicle treated group; *$\leq 0.05$ vs mBSA+mirt group. (B) antigen-induced arthritis induces hypernociception in affected joint (i.e., decreased withdrawal threshold in mBSA+vej group) that is attenuated by mirtazapine treatment. **$\leq 0.01$ vs mBSA+mirt group, and 0.001 vs control vehicle groups; *$p \leq 0.001$ vs control vehicle groups N=4-5 mice/grp.
Figure 23:
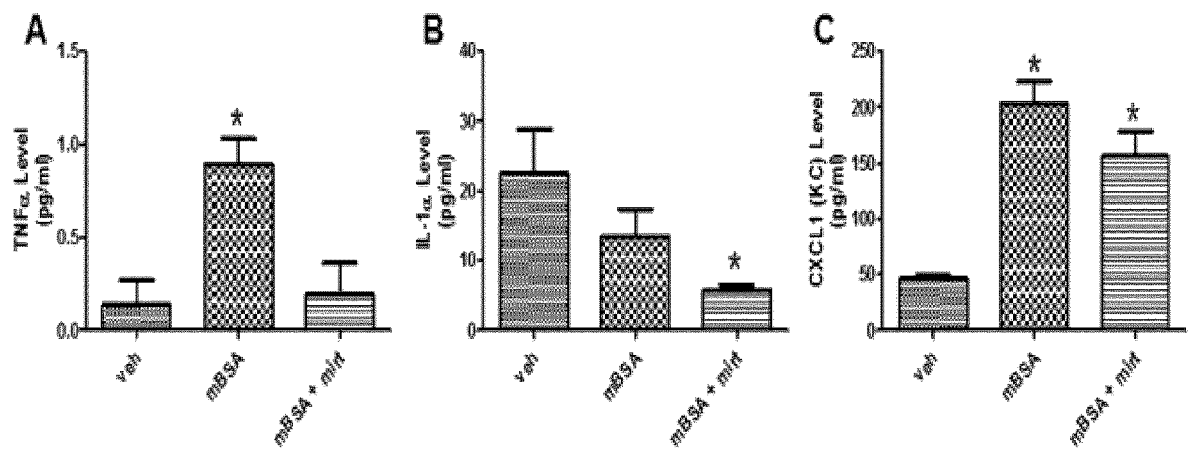
FIG. 23 depicts joint synovial cytokine (TNFα, IL-1α) and chemokine (CXCL1) levels (pg/ml) 24 hrs post-antigen challenge (A) increased joint TNFα levels in mice with antigen-induced arthritis (mBSA) are prevented by mirtazapine treatment (mBSA+mirt). *$p \leq 0.01$ vs other groups (B) Mirtazapine suppresses IL-1α levels (mBSA+mirt) in arthritic joints, compared to vehicle and mBSA treated groups. *$\leq 0.05$ vs other groups (C) joint synovial CXCL1 levels are increased in mBSA and mBRA+mirt treated groups vs vehicle grp. N=4-6 mice/grp.

FIG. 22 depicts joint synovial cytokine (TNFα, IL-1α) and chemokine (CXCL1) levels (pg/ml) 24 hrs post-antigen challenge (A) increased joint TNFα levels in mice with antigen-induced arthritis (mBSA) are prevented by mirtazapine treatment (mBSA+mirt). *p≤0.01 vs other groups (B) Mirtazapine suppresses IL-1a levels (mBSA+mirt) in arthritic joints, compared to vehicle and mBSA treated groups. *≤0.05 vs other groups (C) joint synovial CXCL1 levels are increased in mBSA and mBRA+mirt treated groups vs vehicle grp. N=4-6 mice/grp.

Example 9

Data source: THIN is a primary care patient oriented electronic medical record (EMR) database. It is one of the largest medical databases in the UK, consisting of prospectively gathered electronic medical records from over 11.1 million patients (~3.7 million active patients), the equivalent to 75.6 million patient years, from more than 560 general practices in the UK, covering 6.2% of the UK population. All data elements are fully anonymised and validated by Cegedim Strategic Data (CSD)-Medical Research UK. Patients registered in THIN have demographic, medical conditions, and mortality distribution comparable to the general UK population. Data from participant general practitioners across the UK are exported to THIN administrators and the database is updated every 3 months.

The unique nature of the UK's National Health Services (NHS) allows the lifelong health record of a UK citizen to be held by one practice. Each EMR include comprehensive data on patient diagnoses, pseudonymized commentary written by the health physician, symptoms, prescriptions issued, tests and results, measurements and readings taken in the practice, demographic information, and dates of entry in and out of the database. These dates include information on mortality, conditions outcomes, and treatments. The recording system (Read coding system, Clinical Terms Version 3) is used to code all information with Read Codes. The validity of the THIN database coding system (Read codes) has been assessed in previous studies.

Our objective was to estimate the incidence rates of developing specific IMIDs based on exposure to mirtazapine.

Study cohort: All adult patients (18 years) registered in THIN database starting from Jan. 1, 1995. Since mirtazapine was approved and available in the UK, Europe, and US markets by 1996, all patients who were prescribed mirtazapine with a prescription duration longer than 30 days, were defined as incident cases. We assessed the hazard of developing each studied IMID (CD, UC, psoriasis, MS or RA) separately. For example, to assess the hazard of developing MS in our study cohort, if a patient develops another IMID of interest such as CD and not MS, this patient will be considered as a patient who did not have the outcome of interest. Similarly, in the same MS cohort, if a patient develops another IMID of interest prior to a diagnosis of MS, the index date of outcome will be the date of MS diagnosis. In all of our cohorts, we will follow patients from study start date until an incident diagnosis of IMID of interest, death, loss to follow-up or end of follow-up.

Inclusion and exclusion criteria: Patients should not have any interruption of registration or leave of practice. Cases with mirtazapine prescription duration of less than 30 days or unknown duration were excluded from the study.

Exposure variable of interest: Our primary exposure variable was mirtazapine. We used Read codes to identify mirtazapine usage, duration, dose, and start date. Our primary outcome was the incident diagnosis of one of the following conditions: Crohn's disease, multiple sclerosis, psoriasis, rheumatoid arthritis, and ulcerative colitis during study follow-up period (1995-2017).

Covariates of interest:

a) Demographic covariates: Pre-specified covariates include age at diagnosis; sex; and cigarette smoking status is defined either (1) current smoker, coded for smoking within 12 months of the index date (condition diagnosis date); (2) ex-smoker, coded for smoking before but not within 12 months of the index date; or (3) never smoked, coded either as a lifetime non-smoker or not recorded as a smoker; alcohol consumption classified as current, former, never consumed alcohol, or unknown status at diagnosis; body mass index (weight in kg and height in m2); and socioeconomic status measured by the Mosaic scale which is a consumer classification scale that captures demographics, lifestyles, and behaviours (10 classes).

b) Depression: Read codes were used to identify patients with major depressive disorder (MDD). Read codes associated with only symptoms of depression, bipolar disorder, mania or hypomania were excluded. MDD was defined as (1) never diagnosed with MDD; (2) past MDD diagnosis prior to 90 days from index date; or (3) current MDD diagnosis if a diagnosis was made within 90 days before or after the index date.

c) Comorbidities: We used the Quality and Outcomes Framework (QOF) Read codes to assess for the following comorbidities: asthma, atrial fibrillation, cancer, chronic kidney disease (stages 3-5), chronic obstructive pulmonary disease, coronary heart disease, dementia, diabetes, epilepsy, heart failure, hypertension, and hypothyroid.

d) Exposure to antidepressants: To confirm the mirtazapine effect is specific to its unique properties rather than properties shared with other antidepressants, we adjusted for other antidepressant medications. Exposure was defined as (1) never exposed to the medication, (2) past exposure defined as a previous code for medication use prior to 90 days of index date, or (3) current medication exposure if the medication code was identified within 90 days before or after the index date. We assessed the following atypical and typical antidepressants as follows: Atypical antidepressants include agomelatine and bupropion; Typical antidepressants include the following groups: (a) Selective Serotonin Reuptake Inhibitors (SSRI): citalopram, escitalopram, fluoxetine, fluvoxamine, paroxetine and sertraline; (b) Selective-Norepinephrine Reuptake Inhibitors (SNRI): desvenlafaxine, duloxetine, milnacipran and venlafaxine; (c) serotonin modulators: nefazodone, trazodone and vilazodone; (d) tricyclics and tetracyclics: amitriptyline, amoxapine, clomipramine, desipramine, doxepin, imipramine, maprotiline, nortriptyline and protriptyline, trimipramine; (e) monamine oxidase inhibitors: isocarboxazid, phenelzine, selegiline and tranylcypromine.

We used Incidence rate (IR) and incidence rate ratios (IRRs) Poisson regression to evaluate the incidence of each condition according to mirtazapine exposure.

TABLE 4

Adjusted incidence rate ratio of mirtazapine exposure on developing various IMID among patients registered in THIN database from 1995-2017.

| Variable | Crohn's Disease N = 490 | Ulcerative Colitis N = 1375 | Multiple sclerosis N = 371 | R. arthritis N = 1792 | Psoriasis N = 5181 |
|---|---|---|---|---|---|
| Mirtazapine exposure | 1.00 (0.93-1.07) P = 0.89 | 0.84 (0.81-0.88) P = 0.002 | 0.80 (0.71-0.88) P = 0.006 | 0.55 (0.51-0.60) P < 0.001 | 0.93 (0.88-0.98) P = 0.002 |

Based on these findings, we conclude that mirtazapine has a protective effect on developing ulcerative colitis, multiple sclerosis, rheumatoid arthritis and psoriasis

TABLE 5

| Cohorts Characteristics | | |
|---|---|---|
| Variable | Non-Mirtazapine (n = 382,722) | Mirtazapine (n = 191,361) |
| Sex (% Male) | 41.84 | 41.84 |
| Age (Mean (SD)) | 51.936 (19.891) | 51.936 (19.891) |
| BMI (Mean (SD)) | 26.673 (5.785) | 26.917 (6.522) |
| Height (Mean (SD)) | 1.67 (0.124) | 1.668 (0.119) |
| Weight (Mean (SD)) | 74.481 (18.377) | 74.789 (19.769) |
| Charlson (Median (IQR)) | 0 (1) | 0 (1) |
| (Mean (SD)) | 0.627 (1.285) | 0.842 (1.436) |
| Urban Rural | | |
| 0 | 20.66 (79079) | 29.92 (57264) |
| 1 | 0.15 (570) | 0.14 (275) |
| 2 | 0.54 (2064) | 0.46 (876) |
| 3 | 0.67 (2564) | 0.46 (880) |
| 4 | 63.37 (242540) | 57.19 (109444) |
| 5 | 8.91 (34091) | 7.56 (14467) |
| 6 | 4.65 (17809) | 3.23 (6189) |
| Townsend Score | | |
| 0 | 4.8 (18379) | 4.26 (8157) |
| 1 | 23.23 (88908) | 14.93 (28568) |
| 2 | 20.72 (79308) | 16 (30611) |
| 3 | 20.18 (77230) | 19.33 (36990) |
| 4 | 17.67 (67627) | 22.46 (42980) |
| 5 | 12.06 (46168) | 21.28 (40714) |
| X | 0.29 (1097) | 0.72 (1375) |
| Depression | | |
| Never | 92.7 (354800) | 64.06 (122590) |
| Previous | 4.54 (17375) | 12.36 (23659) |
| Current | 2.76 (10547) | 23.57 (45112) |
| Death (6 Months) | 1.55 (5937) | 2.13 (4075) |
| Death (1 Year) | 2.37 (9062) | 3.52 (6732) |
| Death (2 Year) | 3.57 (13668) | 5.43 (10388) |
| Death (3 Year) | 4.44 (17011) | 6.74 (12894) |
| Cyclics | | |
| Never | 85.01 (325347) | 65.35 (125055) |
| Previous | 5.84 (22367) | 11.65 (22294) |
| Current | 9.15 (35008) | 23 (44012) |
| Atypical | | |
| Never | 99.09 (379231) | 97.87 (187281) |
| Previous | 0.67 (2581) | 1.36 (2601) |
| Current | 0.24 (910) | 0.77 (1479) |
| Monoamine | | |
| Never | 99.97 (382604) | 99.52 (190433) |
| Previous | 0.02 (59) | 0.14 (270) |
| Current | 0.02 (59) | 0.34 (658) |
| Seratonin Modifier | | |
| Never | 98.81 (378182) | 89.38 (171037) |
| Previous | 0.56 (2140) | 2.9 (5544) |
| Current | 0.63 (2400) | 7.72 (14780) |
| SNRI | | |
| Never | 97.45 (372980) | 77.56 (148429) |
| Previous | 1.1 (4228) | 5.2 (9957) |
| Current | 1.44 (5514) | 17.23 (32975) |
| SSRI | | |
| Never | 78.25 (299478) | 29.55 (56552) |
| Previous | 7.54 (28855) | 13.18 (25224) |
| Current | 14.21 (54389) | 57.27 (109585) |
| Smoking Status | | |
| Current | 17.54 (67128) | 36.36 (69572) |
| X (Ex) | 28.66 (109688) | 29.18 (55830) |
| N (Non) | 48.59 (185952) | 32.28 (61775) |
| U (Unknown) | 5.21 (19954) | 2.19 (4184) |

TABLE 5-continued

| Cohorts Characteristics | | |
|---|---|---|
| Variable | Non-Mirtazapine (n = 382,722) | Mirtazapine (n = 191,361) |
| Alcohol Status | | |
| Current | 60.15 (230196) | 54.87 (104994) |
| X (Ex) | 13.01 (49789) | 22.13 (42339) |
| T (Teetoaler) | 6.97 (26680) | 7.19 (13758) |
| U (Unknown) | 19.87 (76057) | 15.82 (30270) |

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The invention claimed is:

1. A method of treating a subject having primary biliary cirrhosis, suspected of having primary biliary cirrhosis, or at risk of developing biliary cirrhosis, comprising:
   administering a therapeutically effective amount of mirtazapine or a functional derivative thereof; and
   administering ursodeoxycholic acid (UDCA).

2. The method of claim 1, further comprising administering one or more of obeticholic acid (INT-747), or other farnesoid X receptor agonists, NGM282, methotrexate, Fibrates (bezafibrate), Fibrates (Fenofibrate), MXB-8025, Budesonide, LUM001 (SHP625), Moexipril, Abatacept, Ustekinumab, rituximab, Mesenchymal Stem Cells, Truvada and Kaletra, Combivir (lamivudine and zidovudine), Pentoxifylline, or tetrathiomolybdate.

3. The method of claim 1, wherein the subject is a human.

* * * * *